United States Patent
Faghih et al.

(10) Patent No.: US 9,828,381 B2
(45) Date of Patent: Nov. 28, 2017

(54) SUBSTITUTED PYRAZOLOPYRIMIDINES AND METHOD OF USE

(71) Applicants: AbbVie Deutschland GmbH & Co. KG, Wiesbaden (DE); AbbVie Inc., North Chicago, IL (US)

(72) Inventors: Ramin Faghih, North Chicago, IL (US); Achim Moeller, Ludwigshafen (DE); Michael Ochse, Ludwigshafen (DE); Frauke Pohlki, Ludwigshafen (DE); Martin Schmidt, Ludwigshafen (DE); Kevin Sippy, North Chicago, IL (US); Sean Turner, Ludwigshafen (DE); Elizabeth Louise Van Der Kam, Ludwigshafen (DE)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 15/133,851

(22) Filed: Apr. 20, 2016

(65) Prior Publication Data

US 2016/0304527 A1    Oct. 20, 2016

(30) Foreign Application Priority Data

Apr. 20, 2015  (WO) ................ PCT/CN2015/076978
May 22, 2015  (EP) .................................... 15168924

(51) Int. Cl.
C07D 487/04    (2006.01)
C07D 519/00    (2006.01)

(52) U.S. Cl.
CPC ......... *C07D 487/04* (2013.01); *C07D 519/00* (2013.01)

(58) Field of Classification Search
CPC .................................................. C07D 487/04
See application file for complete search history.

(56) References Cited

FOREIGN PATENT DOCUMENTS

WO    2008130314 A1    10/2008

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*
Franco et al. (Eur J Med Chem (1996) 31, p. 575-587).*
Kerr et al. (Pharmac. Ther., v. 67, No. 2, p. 187-246 (1995)).*
Marcinkowska et al (European Journal of Medicinal Chemistry 124 (2016), p. 456-467).*
Wermuth, The Practice of Medicinal Chemsitry, 2d ed. (2003), 768 pages. Chs. 9-10 provided.*
Bettler, B., et al., Molecular Structure and Physiological Functions of GABA-B Receptors, Physiol Rev, 2004; 84: 835-867.
Pin, J. P., et al., Activation Mechanism of the Heterodimeric GABA-B Receptor, Biochem Pharmacol, 2004; 68: 1565-1572.
Fritschy, J. M., et al., GABA-B Receptor Splice Variants GB1a and GB1b in Rat Brain: Developmental Regulation, Cellular Distribution and Extrasynamptic Localization; Eur J Neurosci 1999; 11: 761-768.
Bowery, N. G., Historical Perspective and Emergence of the GABA-B Receptor, Adv Pharmacol 2010; 58: 1-182.
Slonimski, M., et al., Intrathecal Baclofen in Pain Management, Reg Anesth Pain Med 2004; 29: 269-276.
Bowery, N. G., et al., Mammalian-Aminobutyric AcidB Receptors: Structure and Function, Pharmacol Rev. 2002; 54: 247-264.
Sands, S. A., et al., Differential Regulation of GABA-B Receptor Subunit Expression and Function, J Pharmacol Exp Ther 2003; 305:191-196.
Schuler, V., et al., Epilepsy, Hyperalgesia, Impaired Memory, and Loss of Pre- and Postsynaptic GABA-B Responses in Mice Lacking GABA-B(1), Neuron 2001; 31: 47-58.
Ross, J. C., et al., Acute Intrathecal Baclofen Withdrawal: A Brief Review of Treatment Options, Neurocrit Care 2011; 14: 103-108.
Wang, L., et al., Allosteric Modulators of G Protein-Coupled Receptors: Future Therapeutics for Complex Physiological Disorders, J Pharmacol Exp Ther 2009; 331: 340-348.
Anghinah, R, et al., Effect of Baclofen on Pain in Diabetic Neuropathy, Muscle Nerve 1994; 17(8): 958-959.
Fromm G.H., et al., Baclofen in the Treatment of Trigeminal Neuralgia: Double-Blind Study and Long-Term Follow-up, Ann. Neuro. 1984; 15: 240-244.
Bowery, N. G., GABA-B Receptor: A Site of Therapeutic Benefit, Curr Opin Pharmacol 2006; 6; 37-433.
Froestl, W., Novel GABA-B Receptor Positive Modulators: a Patent Survey, Expert Opin Ther Pat 2010; 20: 1007-1017.
Ong, J., et al., Clinical Potential of GABA-B Receptor Modulators, CNS Drug Rev 2005; 11: 317-334.
Lozano, R, et al., Modulation of the GABAergic Pathway for the Treatment of Fragile X Syndrome, Neuropsychiatric Disease and Treatment 2014; 10: 1769-1779.

(Continued)

*Primary Examiner* — Robert Havlin
(74) *Attorney, Agent, or Firm* — Neal, Gerber & Eisenberg LLP

(57) ABSTRACT

Compounds of formula (I)

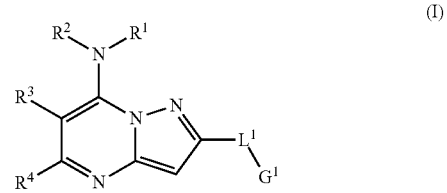

and pharmaceutically acceptable salts thereof, wherein $R^1$, $R^2$, $R^3$, $R^4$, $L^1$ and $G^1$ are as defined in the specification, are useful in treating conditions or disorders prevented by or ameliorated by positive allosteric modulation of the γ-aminobutyric acid B (GABA-B) receptor. Methods for making the compounds are described. Also described are pharmaceutical compositions of compounds of formula (I), and methods for using such compounds and compositions.

14 Claims, No Drawings

(56) References Cited

OTHER PUBLICATIONS

Kleschevnikov, AM., et al., Deficits in Cognition and Synaptic Plasticity in a Mouse Model of Down Syndrome Ameliorated by GABA-B Receptor Antagonists, Journal of Neuroscience 2012; 32(27): 9217-9227.
Oblak, AL, et al., Decreased GABA-B Receptors in the Cingulate Cortex and Fusiform Gyrus in Autism, Journal of Neurochemistry 2010; 114(5): 1414-23.
Hirano, AA, et al., Cellular Distribution and Subcellular Localization of Molecular Components of Vesicular Transmitter Release in Horizontal Cells of Rabbit Retina, Journal of Comparative Neurology 2005; 488(1): 70-81.
Lacy, B.E., et al., GABA-B Receptor Agonist Treatment of Gastroesophageal Reflux Disease, Drugs of the Future 2010; 35(12): 987-992.
Boeckxstaens, C.E. et al., Reflux Inhibitors: A New Approach for GERD, Current Opinion in Pharmacology 2008; 8(6): 585-689.
Lehmann, A, et al., GABA-B Receptor Agonism as a novel Therapeutic Modality in the Treatment of Gastroesophageal Reflux Disease, Advances in Pharmacology 2010; 58: 287-313.
Vlachou, S., et al., Repeated Administration of the Gaba-B Receptor Positive Modulator BHF177 Decreased Nicotine Self-Administration, and Acute Administration Decreased Cue-Induced Reinstatement of Nicotine Seeking in Rats, Psychopharmacology 2011; 215(1): 117-128.
Spano, M.S., et al., The GABA-B Receptor Agonist Baclofen Prevents Heroin-Induced Reinstatement of Heroin-Seeking Behavior in Rats, Neuropharmacology 2007; 52(7): 1555-62.
Sanger, G.J., et al., Treatment of Nausea and Vomiting: Gaps in Our Knowledge, Autonomic Neuroscience 2006; 129 (1-2): 3-16.
Bolser, D.C., et al., Antitussive Effects of GABA-B British Journal of Pharmacology 1993; 110(1): 491-495.
Taylor, M.C., et al., A Double-Blind Crossover Trial of Baclofen—A New Treatment for the Unstable Bladder Syndrome, British J Urology 1979; 51: 504-505.
Krupitsky, E.M., et al., Baclofen Administration for the Treatment of Affective Disorders in Alcoholic Patients, Drug and Alcohol Dependence 1993; 33: 157-163.
Cryan, J.F., et al., Behavioral Characterization of the Novel GABA-B Receptor-Positive Modulator GS39783 (N,N'-Dicyclopentyl-2-methylsulfanyl-5-nitro-pyrimidine-4,6-diamine): Anxiolytic-Like Activity without Side Effects Associated with Baclofen or Benzodiazepines, J Pharmacol Exp Ther 2004; 310: 952-963.
Mombereau, C., et al., Genetic and Pharmacological Evidence of a Role for GABA-B Receptors in the Modulation of Anxiety- and Antidepressant-Like Behavior, Neuropsychopharmacology 2004; 29: 1050-1062.
HeringHanit, R,, Baclofen for Prefentionof Migraine, Cephalalgia 1999; 19(6): 589-91.
Hering-Hanit, R, et al., Baclofen in Cluster Headache, Headache 2000; 40(1): 48-51.
Smith, P.F., et al., Revisiting Baclofen for the Treatment of Severe Chronic Tinnitus, Frontiers in Neurology 2012; 3: 34.
Gjoni, T., et al., Receptor Activation Involving Positive Allosteric Modulation, Unlike Full Agonism, Does not Result in GABA-B Receptor Decensitication, Neuropharmacology 2008; 55: 1293-1299.
Brusberg, M., et al., The GABA-B Receptor Agonist, Baclofen, and the Positive Allosteric Modulator, CGP7930, Inhibit Visceral Pain-Related Responses to Colorectal Distension in Rats, Neuropharmacology 2009; 56: 362-367.
Koek, W., et al., GABA-B Receptor-Positive Modulators: Enhancement of GABA-B Receptor Agonist Effects In Vivo, J Pharmacol Exp Ther 2010; 335: 163-17.
Pin, J.P., et al., Allosteric Modulators of GABA-B Receptors: Mechanism of Action and Therapeutic Perspective, Curr Neuropharmaco12007; 5, 195-201.
Perdona E., et al., "In Vitro and In Vivo Characterization of the Novel Gabab Receptor Positive Allosteric Modulator, 2-{1-[2-(4-Chlorophenyl)-5-Methylpyrazolo[1,5-A]Pyrimidin-7-Yl]-2-Piperidinyl}Ethanol (CMPPE)," Neuropharmacology, 2011, vol. 61 (5-6), pp. 957-966.

\* cited by examiner

SUBSTITUTED PYRAZOLOPYRIMIDINES AND METHOD OF USE

CROSS-REFERENCE TO RELATED PATENT APPLICATIONS

This patent application claims priority to International Patent Application No. PCT/CN2015/076978 filed on Apr. 20, 2015, and European Patent Application No. 15168924.7 filed May 22, 2015. The entire contents of these applications are incorporated by reference into this patent application.

BACKGROUND OF THE INVENTION

Technical Field

The invention relates to substituted pyrazolopyrimidines that are positive allosteric modulators of the γ-aminobutyric acid receptor (e.g., GABA-B PAM), useful in treating diseases and conditions mediated and modulated by the γ-aminobutyric acid receptor B. Additionally, the invention relates to compositions containing compounds of the invention and processes of their preparation.

Description of Related Technology

The inhibitory neurotransmitter, γ-aminobutyric acid (GABA) exerts its actions through three distinct receptors— the ionotropic GABA-A and GABA-C receptors, and the metabotropic GABA-B receptor. The GABA-B receptor is a member of the class C family of GPCRs. The GABA-B receptor is an obligate heterodimer composed of a GABA-B1 and a GABA-B2 subunit (Bettler, B., et al. *Physiol Rev* 2004; 84: 835-867). Notably, heterodimerization of the B1 and B2 subunits is required for proper GABA-B receptor expression and function (Pin, J. P., et al. *Biochem Pharmacol* 2004; 68: 1565-1572). Agonist binding to the B1 subunit of the GABA-B heterodimer results in transactivation of the B2 subunit and subsequent stimulation of $G_{i/o}$ proteins. This, in turn, activates $K^+$ currents, inhibits $Ca^{2+}$ currents, and decreases cAMP via negative regulation of adenylyl cyclase.

GABA-B receptor subunits are found both pre- and post-synaptically throughout the CNS and the periphery, with highest expression in the thalamus, cortex, cerebellum and dorsal horn (Fritschy, J. M., et al. *Eur J Neurosci* 1999; 11: 761-768). Functional receptor expression appears to be limited by the presence of the GABA-B2 subunit, which is often detected at lower levels than the B1 subunits (Bowery, N. G. *Adv Pharmacol* 2010; 58: 1-182). Therapeutically, the beneficial effects of GABA-B receptor stimulation include muscle relaxation, substance abuse treatment (especially in alcohol dependence), antinociception, spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus. The in vivo consequence of GABA-B activation has been confirmed experimentally with knockout mouse models, which are hyperalgesic, and clinically with the GABA-B orthosteric agonist, baclofen (Slonimski, M., et al. *Reg Anesth Pain Med* 2004; 29: 269-276. Bowery, N. G., et al. *Pharmacol Rev* 2002; 54: 247-264). Unfortunately, the utility of baclofen is limited by drug tolerance and severe side effects, including hypothermia, seizures, sedation and cognitive deficits. Baclofen has poor brain penetrance and requires high doses for engagement of CNS GABA-B receptors, resulting in elevated plasma concentrations. Peripheral GABA-B receptors on smooth and skeletal muscle are activated by these high plasma concentrations and appear to mediate a subset of baclofen side effects, including hypothermia and seizures that are hypothesized to arise from erratic muscle contractions. Drug tolerance requiring dose escalation has been reported three to seven days after initiation of baclofen and most likely arises from receptor desensitization (Sands, S. A., et al. *J Pharmacol Exp Ther* 2003; 305: 191-196). This reduction in GABA-B receptor signaling mimics the genotype of GABA-B knockout mice, which also exhibit severe cognitive and learning deficits (Schuler, V., et al. *Neuron* 2001; 31: 47-58). Tolerance and receptor desensitization following repeated baclofen administration may therefore underlie the cognitive deficits and learning impairments associated with baclofen treatment. Finally, abrupt discontinuation of intrathecal baclofen results in severe withdrawal symptoms, including seizures (Ross, J. C., et al. *Neurocrit Care* 2011; 14: 103-108). This indicates an underlying change in the physiological balance of GABA neurotransmitter and GABA-B receptor after continued exogenous agonist stimulation. Similarly, the GABA-B knockout mouse exhibits epileptiform seizures, further underscoring the importance of maintaining the normal, physiological GABA-B tone within the CNS. While the GABA-B receptor remains a valid drug target, the side effects and tolerance associated with baclofen emphasize the need to pursue alternatives to classic orthosteric activation of the receptor.

To exploit the beneficial aspects of GABA-B stimulation, the disclosure describes positive allosteric receptor ligands for modulation of the GABA-B receptor. Positive allosteric modulators alter the receptor conformation and enhance the activity of the endogenous orthosteric agonist, either by increasing the affinity or the efficacy of the orthosteric ligand at the receptor (Wang, L., et al. *J Pharmacol Exp Ther* 2009; 331: 340-348). Because allosteric modulators rely on local levels of endogenous ligand and have little or no activity of their own, they are thought to represent a safer and more subtle means of receptor regulation. The hypothesis is that GABA-B receptor allosteric modulators, and possibly allosteric agonists, will be effective therapeutic agents while minimizing the side effects caused by agonist activation of the orthosteric GABA-B site. In addition to pain indications (Anghinah, R., et al. *Muscle Nerve* 1994; 17(8): 958-959. Fromm G. H., et al. *Ann. Neuro.* 1984; 15: 240-244.), GABA-B modulators could also be used in the treatment of depression, spasticity (Bowery, N. G. *Curr Opin Pharmacol* 2006; 6; 37-433. Froestl, W. *Expert Opin Ther Pat* 2010; 20: 1007-1017. Ong, J., et al. *CNS Drug Rev* 2005; 11: 317-334.)), fragile X syndrome (Lozano, R., et al. *Neuropsychiatric Disease and Treatment* 2014; 10: 1769-1779), Down's syndrome (Kleschevnikov, A. M., et al. *Journal of* Neuroscience 2012; 32(27): 9217-9227), autism (Oblak, A. L., et al. *Journal of Neurochemistry* 2010; 114(5): 1414-23), retinal ganglion cell degeneration (Hirano, A. A., et al. *Journal of Comparative Neurology* 2005; 488(1): 70-81), gastroesophageal reflux disease (GERD) (Lacy, B. E., et al. *Drugs of the Future* 2010; 35(12): 987-992. Boeckxstaens, C. E. et al. *Current Opinion in Pharmacology* 2008; 8(6): 685-689. Lehmann, A., et al. *Advances in Pharmacology* 2010; 58: 287-313) smoking cessation (Vlachou, S., et al. *Psychopharmacology* 2011; 215(1): 117-128), addiction of narcotic agents (Spano, M. S., et al. *Neuropharmacology* 2007; 52(7): 1555-62), emesis (Sanger, G. J., et al. *Autonomic Neuroscience* 2006; 129(1-2): 3-16), cough (Bolser, D. C., et al. *British Journal of Pharmacology* 1993; 110(1): 491-495), overactive bladder (Taylor, M. C., et al. *British J. Urology* 1979; 51: 504-505), anxiety (Krupitsky, E. M., et al. *Drug and Alcohol Dependence* 1993; 33: 157 163. Cryan, J. F., et al. *J Pharmacol Exp Ther* 2004; 310: 952-963. Mombereau, C., et al. *Neuropsychopharmacology* 2004; 29: 1050-1062), migraine (Hering-Hanit, R., *Cephalalgia* 1999; 19(6): 589-91. Hering-Hanit, R., et al. *Headache* 2000; 40(1): 48-51.), and tinnitus (Smith, P. F., et al. *Frontiers in Neurology* 2012; 3: 34). Positive allosteric modulators (PAMs) bind to functionally and topographically distinct allosteric sites on the receptor and act at a distance from the orthosteric site to enhance the efficacy of the endogenous ligand. A single receptor may possess multiple, discrete allosteric sites, each with a unique subset of ligands. Pure PAMs are devoid of activity on their own they will only enhance the potency and/or efficacy of the endogenous agonist thus their pharmacological profile is spatially and temporally controlled by the normal physiological interaction between the endogenous ligand and its receptor. This highlights a critical difference between PAMs and orthosteric agonists PAMs avoid the maximum on/off at all receptors that occurs with classic orthosteric agonist stimulation. Because PAMs rely on endogenous agonist concentrations for activity, they promote fine-tuning of the GABA signal in a physiologically-relevant manner. Importantly, GABA-B PAMs do not cause receptor desensitization (Gjoni, T., et al. *Neuropharmacology* 2008; 55: 1293-1299), so the clinical tolerance and side effects related to receptor desensitization that are observed with baclofen are unlikely to occur. Finally, the majority of GABA-B PAMs tested in the literature (Brusberg, M., et al. *Neuropharmacology* 2009; 56: 362-367. Froestl, W. *Expert Opin Ther Pat* 2010; 20: 1007-1017. Koek, W., et al. *J Pharmacol Exp Ther* 2010; 335: 163-17. Pin, J. P., et al. *Curr Neuropharmacol* 2007; 5, 195-201.) show greatly enhanced brain penetrance as compared to baclofen and excellent efficacies in preliminary studies with minimum or no side effects. These collective data emphasize the need for alternative therapeutics at the GABA-B receptor, and highlight the unique ability of PAMs to stimulate the receptor without baclofen-like side effects.

SUMMARY

The invention is directed to substituted pyazolopyrimidines having a structure of formula (I)

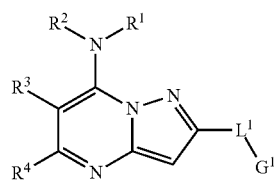

or a pharmaceutically acceptable salt thereof, wherein:
R$^1$ is selected from the group consisting of $C_1$-$C_6$alkyl, $C_2$-$C_6$alkenyl, $C_2$-$C_6$alkynyl, $C_3$-$C_6$cycloalkyl, $C_3$-$C_6$cycloalkyl$C_1$-$C_6$alkyl, 4-7-membered heterocycle and 4-7-membered heterocycle$C_1$-$C_6$alkyl, wherein each of the 4-7-membered heterocycles in the two last mentioned radicals are saturated or have one endocyclic double bond;
   a) the $C_1$-$C_6$alkyl, the $C_2$-$C_6$alkenyl, the $C_2$-$C_6$alkynyl, the $C_1$-$C_6$alkyl of $C_3$-$C_6$cycloalkyl$C_1$-$C_6$alkyl, and the $C_1$-$C_6$alkyl of 4-7-membered heterocycle$C_1$-$C_6$alkyl are unsubstituted or substituted with one or more, e.g. 1, 2, 3, 4 or 5, substituents R$^{1a}$ independently selected from the group consisting of $C_1$-$C_6$alkoxy, $C_1$-$C_6$alkylcarbonylamino, $C_1$-$C_6$alkylsulfonylamino, amido, carboxy, cyano, halogen, hydroxy, and oxo;
   b) the $C_3$-$C_6$cycloalkyl, the $C_3$-$C_6$cycloalkyl of $C_3$-$C_6$cycloalkyl$C_1$-$C_6$alkyl, 4-7-membered heterocycle, and the 4-7-membered heterocycle of 4-7-membered heterocycle$C_1$-$C_6$alkyl are unsubstituted or substituted with one or more, e.g. 1, 2, 3, 4, 5 or 6, substituents R$^{1b}$ independently selected from the group consisting of $C_1$-$C_6$alkoxy, $C_1$-$C_6$alkyl, amido, $C_1$-$C_6$alkylcarbonylamino, $C_1$-$C_6$alkylsulfonylamino, carboxy, cyano, halogen, halo$C_1$-$C_6$alkyl, hydroxy, hydroxy$C_1$-$C_6$alkyl, and oxo;
R$^2$ is selected from the group consisting of hydrogen, $C_1$-$C_6$alkyl, and halo$C_1$-$C_6$alkyl; or
R$^1$, R$^2$ and the nitrogen to which they are attached form a saturated 4-7-membered N-bound heterocycle, which in addition to the nitrogen atom may have one further heteroatom selected from O, S and N as a ring member, wherein:
   each such 4-7-membered heterocycle is unsubstituted or substituted with one or more, e.g. 1, 2, 3, 4, 5 or 6, identical or different substituents R$^{1c}$, where R$^{1c}$ is selected from the group consisting of $C_1$-$C_6$alkoxy, $C_1$-$C_6$alkyl, $C_1$-$C_6$alkylcarbonylamino, $C_1$-$C_6$alkylsulfonylamino, amido, carboxy, cyano, halogen, halo$C_1$-$C_6$alkyl, amino, hydroxy, hydroxy$C_1$-$C_6$alkyl, oxo, spirocyclic bound $C_3$-$C_6$cycloalkyl; and spirocyclic bound saturated 4-6-membered heterocycle; wherein
   each spirocyclic bound $C_3$-$C_6$cycloalkyl and spirocyclic bound 4-6-membered heterocycle is unsubstituted or substituted with one or more substituents independently selected from the group consisting of $C_1$-$C_6$alkyl, cyano, halogen, halo$C_1$-$C_6$alkyl, hydroxy, and hydroxy$C_1$-$C_6$alkyl;
R$^3$ is hydrogen, $C_1$-$C_6$alkyl, or halo$C_1$-$C_6$alkyl;
R$^4$ is hydrogen, $C_1$-$C_6$alkyl, or halo$C_1$-$C_6$alkyl; or
R$^3$ and R$^4$ are joined to form a $C_3$-$C_7$alkylene;
L$^1$ is selected from the group consisting of —(CR$^5$R$^6$)$_m$—, —(CH$_2$)$_n$CR$^{5a}$=CR$^{6a}$(CH$_2$)$_p$—, and

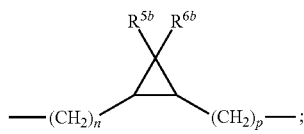

wherein
   c) R$^5$, R$^{5a}$, R$^{5b}$, R$^6$, R$^{6a}$ and R$^{6b}$ are, at each occurrence, independently selected from the group consisting of hydrogen, $C_1$-$C_6$alkyl, fluorine, halo$C_1$-$C_6$alkyl and phenyl, wherein;
   phenyl is unsubstituted or substituted with one or more, e.g. 1, 2, 3, 4 or 5, substituents selected from the group consisting of $C_1$-$C_6$alkyl, halogen, and halo$C_1$-$C_6$alkyl; or
   d) R$^5$ or R$^6$ is a $C_2$-$C_4$alkylene attached to G';
   e) m is 1, 2, 3 or 4;
   f) n is, at each occurrence, independently 0, 1, or 2;
   g) p is, at each occurrence, independently 0, 1, or 2; and
G$^1$ is selected from the group consisting of $C_5$-$C_{10}$cycloalkyl, 5-6-membered heteroaryl, 5-6-membered heterocycle, which is saturated or has one endocyclic double bond, and phenyl; wherein
   each $C_5$-$C_{10}$cycloalkyl, 5-6-membered heteroaryl, 5-6-membered heterocycle, and phenyl is unsubstituted or substituted with one or more, e.g. 1, 2, 3, 4 or 5, identical or different substituents R$^G$, where R$^G$ is selected from the group consisting of $C_1$-$C_6$alkyl, cyano, halo$C_1$-$C_6$alkyl, halogen, $C_1$-$C_6$alkoxy and halo$C_1$-$C_6$alkoxy.

Another aspect of the invention relates to pharmaceutical compositions comprising compounds of the invention. Such compositions can be administered in accordance with a method of the invention, typically as part of a therapeutic regimen for treatment or prevention of conditions and disorders related to γ-aminobutyric acid receptor B (GABA-B) activity.

Yet another aspect of the invention relates to a method of enhancing the activity of the endogenous orthosteric agonist by altering the GABA-B receptor conformation by treatment at an allosteric binding site with a positive allosteric modulator. The method is useful for treating, or preventing conditions and disorders related to pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine and tinnitus in mammals. Accordingly, the compounds and compositions of the invention are useful as a medicament for treating or preventing γ-aminobutyric acid receptor B modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of pain, substance abuse (especially in alcohol dependence), and spasticity.

In an alternative embodiment, certain of the compounds of the invention have a positive allosteric modulator activity.

These and other objects of the invention are described in the following paragraphs. These objects should not be deemed to narrow the scope of the invention.

DETAILED DESCRIPTION OF THE INVENTION

Described herein are compounds of formula (I)

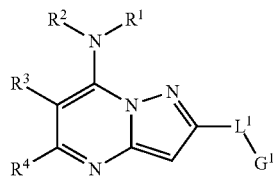

(I)

wherein $R^1$, $R^2$, $R^3$, $R^4$, $L^1$ and $G^1$ are defined above in the Summary and below in the Detailed Description. Further, compositions comprising such compounds and methods for treating conditions and disorders using such compounds and compositions are also described.

Compounds described herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions Of Terms

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, and likewise the term "alkyl" in alkylcarbonyl, alkylcarbonylamino, alkylsulfonyl and alkylsulfonylamino, means a straight or branched, saturated hydrocarbon chain containing from 1 to 10 carbon atoms. The term "lower alkyl" or "$C_1$-$C_6$alkyl" means a straight or branched chain hydrocarbon containing from 1 to 6 carbon atoms. The term "$C_1$-$C_3$alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl (acetyl), ethylcarbonyl, isopropylcarbonyl, n-propylcarbonyl, and the like.

The term "alkylcarbonylamino" as used herein means an alkylcarbonyl group, as defined herein, appended to the parent molecular moiety through an amino group, as defined herein. Representative examples of alkylcarbonylamino include, but are not limited to, methylcarbonylamino, ethylcarbonylamino, isopropylcarbonylamino, n-propylcarbonylamino, and the like.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylamino" as used herein means an alkylsulfonyl group, as defined herein, appended to the parent molecular moiety through an amino group, as defined herein. Representative examples of alkylsulfonylamino include, but are not limited to, methylsulfonylamino, ethylsulfonylamino, and the like.

The term "alkylene" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means a —C(O)NH$_2$ group.

The term "amino" as used herein means an —NH$_2$ group.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "carbonyl" as used herein means a —C(=O)— group.

The term "carboxy" as used herein means a —CO$_2$H group.

The term "cyano" as used herein, means a —CN group.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the present invention can be appended to the parent molecular moiety through any substitutable carbon atom of the groups.

The term "cycloalkylalkyl" as used herein, means a cycloalkyl group appended to the parent molecular moiety through an alkyl group, as defined herein.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl. A subgroup of "haloalkyl" is fluoroalkyl, which means an alkyl group, as defined herein, in which one, two, three, four, five, six, seven or eight hydrogen atoms are replaced by fluorine.

The term "heteroaryl" as used herein, means a heterocyclic aromatic radical and includes monocyclic heteroaryl and a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heterocycle" or "heterocyclic" as used herein, means a non-aromatic heterocyclic radical and includes a monocyclic heterocycle, a bicyclic heterocycle, a tricyclic heterocycle, or a spirocyclic heterocycle. If not stated otherwise, the heterocyclic radical is saturated or has one or two non-conjugated endocyclic double bounds, e.g. a C=N or C=C double bond. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "heterocyclealkyl", as used herein, refers to refers to a heterocycle group attached to the parent molecular moiety through an alkyl group.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "oxo" as used herein means (=O).

The term "sulfonyl," as used herein, refers to a —S(O)$_2$— group.

In some instances, the number of carbon atoms in a hydrocarbyl substituent (e.g., alkyl, haloalkyl, alkenyl, alkynyl, alkylene, alkoxy, haloalkoxy or cycloalkyl) is indicated by the prefix "$C_x$-$C_y$", wherein x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human.

Compounds of the Invention

Compounds of the invention can have the formula (I) as described in the Summary.

Particular values of variable groups in compounds of formula (I) are as follows. Such values can be used where appropriate with any of the other values, definitions, claims or embodiments defined hereinbefore or hereinafter.

Irrespectively of its occurrence, $R^1$ is as defined above or selected from the group consisting of $C_1$-$C_6$alkyl, $C_2$-$C_6$alkenyl, $C_2$-$C_6$alkynyl, $C_3$-$C_6$cycloalkyl, $C_3$-$C_6$cycloalkyl$C_1$-$C_6$alkyl, 4-7-membered heterocycle and 4-7-membered heterocycle$C_1$-$C_6$alkyl; where
  a) the $C_1$-$C_6$alkyl, the $C_2$-$C_6$alkenyl, the $C_2$-$C_6$alkynyl, the $C_1$-$C_6$alkyl of $C_3$-$C_6$cycloalkyl$C_1$-$C_6$alkyl, and the $C_1$-$C_6$alkyl of 4-7-membered heterocycle$C_1$-$C_6$alkyl are unsubstituted or substituted with one or more, e.g. 1, 2, 3, 4 or 5 substituents $R^{1a}$;
  b) the $C_3$-$C_6$cycloalkyl, the $C_3$-$C_6$cycloalkyl of $C_3$-$C_6$cycloalkyl$C_1$-$C_6$alkyl, 4-7-membered heterocycle, and the 4-7-membered heterocycle of 4-7-membered heterocycle$C_1$-$C_6$alkyl are unsubstituted or substituted with one or more, e.g. 1, 2, 3 or 4 substituents $R^{1b}$.

Irrespectively of its occurrence, $R^1$ is more particularly selected from the group consisting of
  $C_1$-$C_6$alkyl, which is unsubstituted or substituted by 1, 2, 3 or 4 radicals $R^{1a}$,
  $C_3$-$C_6$cycloalkyl and $C_3$-$C_6$cycloalkyl$C_1$-$C_6$alkyl; where $C_3$-$C_6$cycloalkyl and the $C_3$-$C_6$cycloalkyl of $C_3$-$C_6$cycloalkyl$C_1$-$C_6$alkyl, are unsubstituted or substituted with one or more, e.g. 1, 2, 3 or 4, substituents $R^{1b}$.

In this context, $R^{1a}$ is in particular selected from the group of halogen, in particular fluorine, CN, $C_1$-$C_4$alkoxy and hydroxyl. Especially $R^{1a}$ is fluorine.

In this context, $R^{1b}$ is in particular selected from the group of halogen, in particular fluorine, $C_1$-$C_4$alkyl, CN, halo$C_1$-$C_4$alkyl, hydroxy$C_1$-$C_4$alkyl, $C_1$-$C_4$alkoxy, hydroxyl and oxo. More particularly $R^{1b}$ is selected from the group of fluorine, $C_1$-$C_2$alkyl, fluoro$C_1$-$C_2$alkyl, and hydroxyl. Especially $R^{1b}$ is fluorine, methyl, or trifluoromethyl.

Irrespectively of its occurrence, $R^2$ is in particular selected from the group consisting of hydrogen, $C_1$-$C_6$alkyl, and halo$C_1$-$C_6$alkyl.

A particular group (1) of embodiments relates to compounds of the formula (I) and to their pharmaceutically acceptable salts, wherein $R^1$ is selected from the group consisting of $C_1$-$C_6$alkyl, $C_2$-$C_6$alkenyl, $C_2$-$C_6$alkynyl, $C_3$-$C_6$cycloalkyl, $C_3$-$C_6$cycloalkyl$C_1$-$C_6$alkyl, 4-7-membered heterocycle and 4-7-membered heterocycle$C_1$-$C_6$alkyl;
  a) the $C_1$-$C_6$alkyl, the $C_2$-$C_6$alkenyl, the $C_2$-$C_6$alkynyl, the $C_1$-$C_6$alkyl of $C_3$-$C_6$cycloalkyl$C_1$-$C_6$alkyl, and the $C_1$-$C_6$alkyl of 4-7-membered heterocycle$C_1$-$C_6$alkyl are unsubstituted or substituted with one or more substituents $R^{1a}$;
  b) the $C_3$-$C_6$cycloalkyl, the $C_3$-$C_6$cycloalkyl of $C_3$-$C_6$cycloalkyl$C_1$-$C_6$alkyl, 4-7-membered heterocycle, and the 4-7-membered heterocycle of 4-7-membered heterocycle$C_1$-$C_6$alkyl are unsubstituted or substituted with one or more substituents $R^{1b}$; and $R^2$ is selected from the group consisting of hydrogen, $C_1$-$C_6$alkyl, and halo$C_1$-$C_6$alkyl and wherein $R^2$ is in particular selected from the group consisting hydrogen, $C_1$-$C_4$alkyl and fluoro$C_1$-$C_4$alkyl. In group (1) of embodiments, $R^2$ is especially hydrogen.

In this group (1) of embodiments, $R^1$ may be in particular selected from the group consisting of $C_1$-$C_6$alkyl, $C_2$-$C_6$alkenyl, $C_2$-$C_6$alkynyl, wherein the $C_1$-$C_6$alkyl, the $C_2$-$C_6$alkenyl and the $C_2$-$C_6$alkynyl are unsubstituted or substituted with one or more, e.g. 1, 2 or 3 halogen atoms, especially fluorine atoms. This group of embodiments is also termed group (1a) of embodiments. In this group (1a) of embodiments, $R^1$ is especially $C_1$-$C_6$alkyl, which is unsubstituted or substituted with one or more, e.g. 1, 2 or 3 halogen atoms, especially fluorine atoms.

In this group (1) of embodiments, $R^1$ may also be selected from the group consisting of $C_3$-$C_6$cycloalkyl, $C_3$-$C_6$cycloalkyl$C_1$-$C_6$alkyl, 4-7-membered heterocycle and 4-7-membered heterocycle$C_1$-$C_6$alkyl, especially from the group consisting of $C_3$-$C_6$cycloalkyl and $C_3$-$C_6$cycloalkyl$C_1$-$C_6$alkyl, where
  a) the $C_1$-$C_6$alkyl of $C_3$-$C_6$cycloalkyl$C_1$-$C_6$alkyl, and the $C_1$-$C_6$alkyl of 4-7-membered heterocycle$C_1$-$C_6$alkyl are unsubstituted or substituted with one or more, e.g. 1, 2, 3, 4 or 5 substituents $R^{1a}$; and
  b) the $C_3$-$C_6$cycloalkyl, the $C_3$-$C_6$cycloalkyl of $C_3$-$C_6$cycloalkyl$C_1$-$C_6$alkyl, the 4-7-membered heterocycle, and the 4-7-membered heterocycle of 4-7-membered heterocycle$C_1$-$C_6$alkyl are unsubstituted or substituted with one or more, e.g. 1, 2, 3 or 4, substituents $R^{1b}$.

This group of embodiments is also termed group (1b) of embodiments. In this group (1b) of embodiments, R1 is especially C3-C6cycloalkyl or C3-C6cycloalkylC1-C6alkyl, where the C3-C6cycloalkyl or the C3-C6cycloalkyl of C3-C6cycloalkylC1-C6alkyl are unsubstituted or substituted with one or more, e.g. 1, 2, 3 or 4, substituents R1b.

In groups (1a) and (1b) of embodiments, $R^2$ is as defined above and especially hydrogen.

In the context of groups (1), (1a) and (1b) of embodiments, $R^{1a}$ is as defined above or selected from the group of halogen, in particular fluorine, CN, $C_1$-$C_4$alkoxy and hydroxyl. Especially $R^{1a}$ is fluorine.

In the context of groups (1), (1a) and (1b) of embodiments, $R^{1b}$ is as defined above or selected from the group of halogen, in particular fluorine, $C_1$-$C_4$alkyl, CN, halo$C_1$-$C_4$alkyl, hydroxy$C_1$-$C_4$alkyl, $C_1$-$C_4$alkoxy, hydroxyl and oxo. In particular, $R^{1b}$ is selected from the group of fluorine, $C_1$-$C_2$alkyl, fluoro$C_1$-$C_2$alkyl, and hydroxyl. Especially $R^{1b}$ is fluorine, methyl, or trifluoromethyl.

Particular examples of the group $NR^1R^2$ of this group (1) of embodiments include 2,2,2-trifluoroethylamino, ter t-butylamino, 1-(trifluoromethyl)ethylamino, 1-methylcyclopropylamino, 1-(trifluoromethyl)cyclopropylamino, 3-fluorocyclobutylamino, 3,3-difluorocyclobutylamino, 3-hydroxycyclobutylamino, and (3,3-difluorocyclobutyl) methylamino.

Another particular group (2) of embodiments relates to compounds of the formula (I) and to their pharmaceutically acceptable salts, wherein the moiety $NR^1R^2$ forms a saturated 4-7-membered N-bound heterocycle, which in addition to the nitrogen atom may have one further heteroatom selected from O, S and N as a ring member, wherein each such 4-7-membered heterocycle is unsubstituted or substituted with one or more, e.g. 1, 2, 3, 4, 5 or 6, identical or different substituents $R^{1c}$. In this group (2) of embodiments the moiety $NR^1R^2$ is in particular selected from the group consisting of azetidinyl, pyrrolidinyl, piperidinyl, piperazinyl, morpholinyl, thiomorpholinyl, and azepanyl wherein azetidinyl, pyrrolidinyl, piperidinyl, piperazinyl, morpholinyl, thiomorpholinyl, and azepanyl are unsubstituted or carry 1, 2, 3 or 4 identical or different radicals $R^{1c}$.

In a subgroup (2a) of this group (2) of embodiments the moiety $NR^1R^2$ is a 4-5-membered heterocycle selected from the group consisting of azetidinyl and pyrrolidinyl, wherein azetidinyl and pyrrolidinyl are unsubstituted or carry 1, 2, 3 or 4 identical or different radicals $R^{1c}$.

In another subgroup (2b) of this group (2) of embodiments the moiety $NR^1R^2$ is a 6-7-membered heterocycle selected from the group consisting of piperidinyl, piperazinyl and azepanyl wherein piperidinyl, piperazinyl and azepanyl are unsubstituted or carry 1, 2, 3 or 4 identical or different radicals $R^{1c}$.

In the context of groups (2), (2a) and (2b) of embodiments, $R^{1c}$ is as defined above or selected from the group consisting of halogen, in particular fluorine, oxo, hydroxyl, $C_1$-$C_6$alkyl, such as methyl or ethyl, halo$C_1$-$C_6$alkyl, in particular fluoro$C_1$-$C_2$alkyl, such as difluoromethyl, trifluoromethyl or 2,2,2-trifluoroethyl, hydrox$C_1$-$C_6$yalkyl, such as hydroxymethyl or 2-hydroxyethyl, $C_1$-$C_6$alkylcarbonylamino, such as methylcarbonylamino, $C_1$-$C_6$alkylsulfonylamino, such as methylsulfonylamino, amido, carboxy, spiro-bound saturated $C_3$-$C_6$cycloalkyl, and spiro-bound saturated 4-6-membered heterocycle, where the spiro-bound $C_3$-$C_6$cycloalkyl and the spiro-bound 4-6-membered heterocycle are unsubstituted or carry 1 or 2 radicals as defined above, which are in particular selected from halogen, hydroxyl, $C_1$-$C_2$alkyl and fluoro$C_1$-$C_2$alkyl. Examples of spiro-bound radicals include spiro-bound cyclopropyl, spiro-bound cyclobutyl, spiro-bound cyclopentyl, spiro-bound hydroxycyclopropyl, spiro-bound hydroxycyclobutyl, spiro-bound hydroxycyclopentyl, spiro bound oxetanyl, spiro-bound oxolanyl and spiro-bound oxanyl.

In the context of groups (2), (2a) and (2b) of embodiments, $R^{1c}$ is especially selected from the group consisting of halogen, in particular fluorine, hydroxyl, methyl, ethyl, hydroxymethyl, 2-hydroxyethyl, methylcarbonylamino, methylsulfonylamino, amido, carboxy, spiro-bound cyclopropyl, spiro-bound cyclobutyl, spiro-bound cyclopentyl, spiro-bound hydroxycyclopropyl, spiro-bound hydroxycyclobutyl, spiro-bound hydroxycyclopentyl, spiro bound oxetanyl, spiro-bound oxolanyl and spiro-bound oxanyl.

Particular examples of the group $NR^1R^2$ in this group (2) of embodiments include azetidin-1-yl, 3-ethyl-2-carboxylazetidin-1-yl, pyrroldin-1-yl, 3,3-difluoropyrrolidin-1-yl, 3-(acetyl amino)pyrrolidin-1-yl, 3-(methylsulfonylamino) pyrrolidin-1-yl, 3-aminocarbonylpyrrolidin-1-yl, piperidin-1-yl, 3-fluoropiperidin-1-yl, 4-fluoropiperidin-1-yl, 2-(2-hydroxyethyl)piperidin-1-yl, 2-ethylpiperidin-1-yl, 2-(hydroxymethyl)piperidin-1-yl, 3-(hydroxymethyl)piperidin-1-yl, 2-oxopiperidin-1-yl, 3-(methylsulfonylamino)piperidin-1-yl, 2-(2-hydroxyethyl)-3-oxopiperazin-1-yl, 3-difluorpiperidin-1-yl, 3-hydroxypiperidin-1-yl, 4-hydroxy-3,3-difluoropiperidin-1-yl, 2-oxa-6-azaspiro[3.4]oct-6-yl, 2-oxa-7-azaspiro-[3.5]non-7-yl, 7-oxa-2-azaspiro[3.5]non-2-yl and 3-hydroxy-7-azaspiro[3.4]oct-7-yl.

A particular group (A) of embodiments relates to compounds of the formula (I) and to their pharmaceutically acceptable salts, wherein $L^1$ is —$(CR^5R^6)_m$—, wherein m, $R^5$ and $R^6$ are as defined herein. In particular m is 1. In particular $R^5$ and $R^6$ are, independently selected from the group consisting of hydrogen and $C_1$-$C_6$alkyl, especially from hydrogen and $C_1$-$C_4$-alkyl, such as methyl, ethyl, n-propyl, 2-propyl and n-butyl. Especially, both $R^5$ and $R^6$ are hydrogen or $R^5$ is hydrogen and $R^6$ is $C_1$-$C_6$alkyl.

Another group (B) of embodiments relates to compounds of the formula (I) and to their pharmaceutically acceptable salts, wherein $L^1$ is —$(CH_2)_6CR^{5a}$=$CR^{6a}(CH_2)_p$—. In this group (2) of embodiments, n and p are in particular 0. In particular, $R^{5a}$ and $R^{6a}$ are, independently selected from the group consisting of hydrogen and $C_1$-$C_6$alkyl, especially from the group consisting of hydrogen and methyl.

Another group (C) of embodiments relates to compounds of the formula (I) and to their pharmaceutically acceptable salts, wherein $L^1$ is

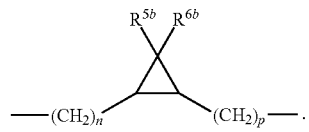

In this particular group (3) of embodiments, n and p are as defined above or in particular 0. $R^{5b}$ and $R^{6b}$ are as defined above or independently selected from the group consisting of hydrogen and $C_1$-$C_6$alkyl. Especially, $R^{5b}$ and $R^{6b}$ are hydrogen or methyl.

Further particular groups of embodiments relate to compounds of the formula (I) and to their pharmaceutically acceptable salts, in particular to the compounds of groups (1), (1a), (1b), (2), (2a), (2b), (A), (B) and (C) of embodiments, wherein $G^1$ is selected from the group consisting of 5-6-membered heteroaryl and phenyl, wherein the 5-6-membered heteroaryl and phenyl are unsubstituted or carry 1, 2, 3 or 4 radicals $R^G$. In particular $G^1$ is selected from the group consisting of 6-membered heteroaryl, such as pyridyl, pyrimidinyl, pyrazinyl or pyridazinyl, and phenyl, wherein the 6-membered heteroaryl and phenyl are unsubstituted or carry 1, 2, 3 or 4 radicals $R^G$. More particularly, $G^1$ is selected from the group consisting of pyridyl, such as 2- or 3-pyridyl, and phenyl, wherein the pyridyl and phenyl are unsubstituted or carry 1, 2 or 3 radicals $R^G$. Especially, $G^1$ is phenyl, which is unsubstituted or carries 1, 2 or 3 radicals $R^G$.

In this context $R^G$ is as defined above or selected from the group consisting of $C_1$-$C_6$alkyl, halo$C_1$-$C_6$alkyl, and halogen, in particular from the group consisting of $C_1$-$C_4$alkyl, fluoro$C_1$-$C_4$alkyl, fluorine and chlorine, and especially from the group consisting of fluoro$C_1$-$C_2$alkyl, fluorine and chlorine.

Particular examples of $G^1$ include but are not limited to phenyl, 3-chlorophenyl, 4-chlorophenyl, 4-(trifluoromethyl)phenyl, pyridine-2-yl and 5-chloropyridin-2-yl.

In formula (I) and likewise in the compounds of groups (1), (1a), (1b), (2), (2a), (2b), (A), (B) and (C) of embodiments, $R^3$ is as defined above or in particular hydrogen.

In formula (I) and likewise in the compounds of groups (1), (1a), (1b), (2), (2a), (2b), (A), (B) and (C) of embodiments, $R^4$ is as defined above or $C_1$-$C_6$alkyl, in particular $C_1$-$C_4$alkyl, and especially methyl or ethyl.

In particular, the present invention relates to compounds of the formula (I) and to their pharmaceutically acceptable salts, wherein the combination variables $L^1$, $G^1$, $R^3$ and $R^4$ are as follows:

$L^1$ is —$(CR^5R^6)_m$—, wherein m is 1 and wherein $R^5$ and $R^6$ are, independently selected from the group consisting of hydrogen and $C_1$-$C_6$alkyl, especially from hydrogen and $C_1$-$C_4$-alkyl, such as methyl, ethyl, n-propyl, 2-propyl and n-butyl. More particularly, both $R^5$ and $R^6$ are hydrogen or $R^5$ is hydrogen and $R^6$ is $C_1$-$C_4$alkyl;

$G^1$ is selected from the group consisting of 5-6-membered heteroaryl and phenyl, wherein the 5-6-membered heteroaryl and phenyl are unsubstituted or carry 1, 2, 3 or 4 radicals $R^G$. In particular $G^1$ is selected from the group consisting of 6-membered heteroaryl, such as pyridyl, pyrimidinyl, pyrazinyl or pyridazinyl, and phenyl, wherein the 6-membered heteroaryl and phenyl are unsubstituted or carry 1, 2, 3 or 4 radicals $R^G$. More particularly, $G^1$ is selected from the group consisting of pyridyl, such as 2- or 3-pyridyl, and phenyl, wherein the pyridyl and phenyl are unsubstituted or carry 1, 2 or 3 radicals $R^G$. Especially, $G^1$ is phenyl, which is unsubstituted or carries 1, 2 or 3 radicals $R^G$. In this context $R^G$ is in particular selected from the group consisting of $C_1$-$C_6$alkyl, halo$C_1$-$C_6$alkyl, and halogen, in particular from the group consisting of $C_1$-$C_4$alkyl, fluoro$C_1$-$C_4$alkyl, fluorine and chlorine, and especially from the group consisting of fluoro$C_1$-$C_2$alkyl, fluorine and chlorine;

$R^3$ is hydrogen; and $R^4$ is $C_1$-$C_4$alkyl, and especially methyl or ethyl.

More particularly, the present invention relates to compounds of the formula (I) and to their pharmaceutically acceptable salts, wherein the combination variables $L^1$, $G^1$, $R^3$ and $R^4$ are as follows:

$L^1$ is —$(CR^5R^6)_m$—, wherein m is 1 and wherein $R^5$ and $R^6$ are, independently selected from the group consisting of hydrogen and $C_1$-$C_6$alkyl, especially from hydrogen and $C_1$-$C_4$-alkyl, such as methyl, ethyl, n-propyl, 2-propyl and n-butyl. More particularly, both $R^5$ and $R^6$ are hydrogen or $R^5$ is hydrogen and $R^6$ is $C_1$-$C_4$alkyl;

$G^1$ is selected from the group consisting of phenyl, 3-chlorophenyl, 4-chlorophenyl, 4-(trifluoromethyl)phenyl, pyridine-2-yl and 5-chloropyridin-2-yl;

$R^3$ is hydrogen; and $R^4$ is $C_1$-$C_4$alkyl, and especially methyl or ethyl.

More particularly, the present invention also relates to compounds of the formula (I) and to their pharmaceutically acceptable salts, wherein the combination variables $L^1$, $G^1$, $R^1$, $R^2$, $R^3$ and $R^4$ are as follows:

$L^1$ is —$(CR^5R^6)_m$—, wherein m is 1 and wherein $R^5$ and $R^6$ are, independently selected from the group consisting of hydrogen and $C_1$-$C_6$alkyl, especially from hydrogen and $C_1$-$C_4$-alkyl, such as methyl, ethyl, n-propyl, 2-propyl and n-butyl. More particularly, both $R^5$ and $R^6$ are hydrogen and especially $R^5$ is hydrogen and $R^6$ is $C_1$-$C_4$alkyl;

$G^1$ is selected from the group consisting of 5-6-membered heteroaryl and phenyl, wherein the 5-6-membered heteroaryl and phenyl are unsubstituted or carry 1, 2, 3 or 4 radicals $R^G$. In particular $G^1$ is selected from the group consisting of 6-membered heteroaryl, such as pyridyl, pyrimidinyl, pyrazinyl or pyridazinyl, and phenyl, wherein the 6-membered heteroaryl and phenyl are unsubstituted or carry 1, 2, 3 or 4 radicals $R^G$. More particularly, $G^1$ is selected from the group consisting of pyridyl, such as 2- or 3-pyridyl, and phenyl, wherein the pyridyl and phenyl are unsubstituted or carry 1, 2 or 3 radicals $R^G$. Especially, $G^1$ is s phenyl, which is unsubstituted or carries 1, 2 or 3 radicals $R^G$. In this context $R^G$ is as defined above or selected from the group consisting of $C_1$-$C_6$alkyl, halo$C_1$-$C_6$alkyl, and halogen, in particular from the group consisting of $C_1$-$C_4$alkyl, fluoro$C_1$-$C_4$alkyl, fluorine and chlorine, and especially from the group consisting of fluoro $C_1$-$C_2$alkyl, fluorine and chlorine;

$R^3$ is hydrogen;

$R^4$ is $C_1$-$C_4$alkyl, and especially methyl or ethyl;

and $R^1$ and $R^2$ are as defined for groups (1), (1a) or (1b) of embodiments.

More particularly, the present invention also relates to compounds of the formula (I) and to their pharmaceutically acceptable salts, wherein the combination variables $L^1$, $G^1$, $NR^1R^2$, $R^3$ and $R^4$ are as follows:

$L^1$ is —$(CR^5R^6)_m$—, wherein m is 1 and wherein $R^5$ and $R^6$ are, independently selected from the group consisting of hydrogen and $C_1$-$C_6$alkyl, especially from hydrogen and $C_1$-$C_4$-alkyl, such as methyl, ethyl, n-propyl, 2-propyl and n-butyl. More particularly, both $R^5$ and $R^6$ are hydrogen or $R^5$ is hydrogen and $R^6$ is $C_1$-$C_4$alkyl;

$G^1$ is selected from the group consisting of 5-6-membered heteroaryl and phenyl, wherein the 5-6-membered heteroaryl and phenyl are unsubstituted or carry 1, 2, 3 or 4 radicals $R^G$. In particular $G^1$ is selected from the group consisting of 6-membered heteroaryl, such as pyridyl, pyrimidinyl, pyrazinyl or pyridazinyl, and phenyl, wherein the 6-membered heteroaryl and phenyl are unsubstituted or carry 1, 2, 3 or 4 radicals $R^G$. More particularly, $G^1$ is selected from the group consisting of pyridyl, such as 2- or 3-pyridyl, and phenyl, wherein the pyridyl and phenyl are unsubstituted or carry 1, 2 or 3 radicals $R^G$. Especially, $G^1$ is s phenyl, which is unsubstituted or carries 1, 2 or 3 radicals $R^G$. In this context $R^G$ is in particular selected from the group consisting of $C_1$-$C_6$alkyl, halo$C_1$-$C_6$alkyl, and halogen, in particular from the group consisting of $C_1$-$C_4$alkyl, fluoro$C_1$-$C_4$alkyl, fluorine and chlorine, and especially from the group consisting of fluoro$C_1$-$C_2$alkyl, fluorine and chlorine;

$R^3$ is hydrogen;

$R^4$ is $C_1$-$C_4$alkyl, and especially methyl or ethyl;

and NR$^1$R$^2$ is as defined for groups (2), (2a) or (2b) of embodiments.

Especially, the present invention relates to compounds of the formula (I) and to their pharmaceutically acceptable salts, wherein the combination variables L$^1$, G$^1$, R$^1$, R$^2$, R$^3$ and R$^4$ are as follows:

L$^1$ is —(CR$^5$R$^6$)$_m$—, wherein m is 1 and wherein R$^5$ and R$^6$ are, independently selected from the group consisting of hydrogen and C$_1$-C$_6$alkyl, especially from hydrogen and C$_1$-C$_4$-alkyl, such as methyl, ethyl, n-propyl, 2-propyl and n-butyl. More particularly, both R$^5$ and R$^6$ are hydrogen or R$^5$ is hydrogen and R$^6$ is C$_1$-C$_4$alkyl;

G$^1$ is selected from the group consisting of phenyl, 3-chlorophenyl, 4-chlorophenyl, 4-(trifluoromethyl)phenyl, pyridine-2-yl and 5-chloropyridin-2-yl;

R$^3$ is hydrogen;

R$^4$ is C$_1$-C$_4$alkyl, and especially methyl or ethyl;

and R$^1$ and R$^2$ are as defined for groups (1), (1a) or (1b) of embodiments and wherein the moiety NR$^1$R$^2$ is in particular selected from the group consisting of 2,2,2-trifluoroethylamino, tert-butylamino, 1-(trifluoromethyl)ethylamino, 1-methylcyclopropylamino, 1-(trifluoromethyl)cyclopropylamino, 3-fluorocyclobutylamino, 3,3-difluorocyclobutylamino, 3-hydroxycyclobutylamino, and (3,3-difluorocyclobutyl)methylamino.

Especially, the present invention relates to compounds of the formula (I) and to their pharmaceutically acceptable salts, wherein the combination variables L$^1$, G$^1$, NR$^1$R$^2$, R$^3$ and R$^4$ are as follows:

L$^1$ is —(CR$^5$R$^6$)$_m$—, wherein m is 1 and wherein R$^5$ and R$^6$ are, independently selected from the group consisting of hydrogen and C$_1$-C$_6$alkyl, especially from hydrogen and C$_1$-C$_4$-alkyl, such as methyl, ethyl, n-propyl, 2-propyl and n-butyl. More particularly, both R$^5$ and R$^6$ are hydrogen or R$^5$ is hydrogen and R$^6$ is C$_1$-C$_4$alkyl;

G$^1$ is selected from the group consisting of phenyl, 3-chlorophenyl, 4-chlorophenyl, 4-(trifluoromethyl)phenyl, pyridine-2-yl and 5-chloropyridin-2-yl;

R$^3$ is hydrogen;

R$^4$ is C$_1$-C$_4$alkyl, and especially methyl or ethyl;

and NR$^1$R$^2$ is as defined for groups (2), (2a) or (2b) of embodiments, and wherein the moiety NR$^1$R$^2$ is in particular selected from the group consisting of azetidin-1-yl, 3-ethyl-2-carboxylazetidin-1-yl, pyrroldin-1-yl, 3,3-difluoropyrrolidin-1-yl, 3-(acetylamino)pyrrolidin-1-yl, 3-(methylsulfonylamino)pyrrolidin-1-yl, 3-aminocarbonylpyrrolidin-1-yl, piperidin-1-yl, 3-fluoropiperidin-1-yl, 4-fluoropiperidin-1-yl, 2-(2-hydroxyethyl)piperidin-1-yl, 2-ethylpiperidin-1-yl, 2-(hydroxymethyl)piperidin-1-yl, 3-(hydroxymethyl)piperidin-1-yl, 2-oxopiperidin-1-yl, 3-(methylsulfonylamino)piperidin-1-yl, 2-(2-hydroxyethyl)-3-oxopiperazin-1-yl, 3,3-difluorpiperidin-1-yl, 3-hydroxypiperidin-1-yl, 4-hydroxy-3,3-difluoropiperidin-1-yl, 2-oxa-6-azaspiro[3.4]oct-6-yl, 2-oxa-7-azaspiro-[3.5]non-7-yl, 7-oxa-2-azaspiro[3.5]non-2-yl and 3-hydroxy-7-azaspiro[3.4]oct-7-yl.

Specific embodiments contemplated as part of the invention also include, but are not limited to, compounds or pharmaceutically acceptable salts thereof, as defined, for example:

2-{1-[2-(4-chlorobenzyl)-5-methylpyrazolo[1,5-a]pyrimidin-7-yl]piperidin-2-yl}ethanol;

{1-[2-(4-chlorobenzyl)-5-methylpyrazolo[1,5-a]pyrimidin-7-yl]piperidin-2-yl}methanol;

2-(4-chlorobenzyl)-5-methyl-N-(1-methylcyclopropyl)pyrazolo[1,5-a]pyrimidin-7-amine;

2-(4-chlorobenzyl)-7-(3,3-difluoropiperidin-1-yl)-5-methylpyrazolo[1,5-a]pyrimidine;

1-[2-(4-chlorobenzyl)-5-methylpyrazolo[1,5-a]pyrimidin-7-yl]-3,3-difluoropiperidin-4-ol;

(3S)-1-[2-(4-chlorobenzyl)-5-methylpyrazolo[1,5-a]pyrimidin-7-yl]piperidin-3-ol;

(3R)-1-[2-(4-chlorobenzyl)-5-methylpyrazolo[1,5-a]pyrimidin-7-yl]piperidin-3-ol;

{(3S)-1-[2-(4-chlorobenzyl)-5-methylpyrazolo[1,5-a]pyrimidin-7-yl]piperidin-3-yl}methanol;

2-(4-chlorobenzyl)-5-methyl-7-(piperidin-1-yl)pyrazolo[1,5-a]pyrimidine;

1-[2-(4-chlorobenzyl)-5-methylpyrazolo[1,5-a]pyrimidin-7-yl]piperidin-2-one;

N-{(3R)-1-[2-(4-chlorobenzyl)-5-methylpyrazolo[1,5-a]pyrimidin-7-yl]pyrrolidin-3-yl}acetamide;

2-(4-chlorobenzyl)-5-methyl-7-(pyrrolidin-1-yl)pyrazolo[1,5-a]pyrimidine;

7-(azetidin-1-yl)-2-(4-chlorobenzyl)-5-methylpyrazolo[1,5-a]pyrimidine;

N-tert-butyl-2-(4-chlorobenzyl)-5-methylpyrazolo[1,5-a]pyrimidin-7-amine;

2-(4-chlorobenzyl)-5-methyl-N-[1-(trifluoromethyl)cyclopropyl]pyrazolo[1,5-a]pyrimidin-7-amine;

2-(4-chlorobenzyl)-5-methyl-N-(2,2,2-trifluoroethyl)pyrazolo[1,5-a]pyrimidin-7-amine;

N-{(3S)-1-[2-(4-chlorobenzyl)-5-methylpyrazolo[1,5-a]pyrimidin-7-yl]pyrrolidin-3-yl}acetamide;

2-(4-chlorobenzyl)-5-methyl-N-[(2S)-1,1,1-trifluoropropan-2-yl]pyrazolo[1,5-a]pyrimidin-7-amine;

1-[2-(4-chlorobenzyl)-5-methylpyrazolo[1,5-a]pyrimidin-7-yl]piperidine-3-carboxamide;

2-(4-chlorobenzyl)-5-methyl-N-[(2R)-1,1,1-trifluoropropan-2-yl]pyrazolo[1,5-a]pyrimidin-7-amine;

{(3R)-1-[2-(4-chlorobenzyl)-5-methylpyrazolo[1,5-a]pyrimidin-7-yl]piperidin-3-yl}methanol;

2-(1-{2-[1-(4-chlorophenyl)ethyl]-5-methylpyrazolo[1,5-a]pyrimidin-7-yl}piperidin-2-yl)ethanol;

2-[1-(4-chlorophenyl)ethyl]-5-methyl-N-(1-methylcyclopropyl)pyrazolo[1,5-a]pyrimidin-7-amine;

2-[1-(4-chlorophenyl)ethyl]-7-(3,3-difluoropyrrolidin-1-yl)-5-methylpyrazolo[1,5-a]pyrimidine;

2-[1-(4-chlorophenyl)ethyl]-7-(4-fluoropiperidin-1-yl)-5-methylpyrazolo[1,5-a]pyrimidine;

(1-{2-[1-(4-chlorophenyl)ethyl]-5-methylpyrazolo[1,5-a]pyrimidin-7-yl}piperidin-2-yl)methanol;

2-[1-(4-chlorophenyl)ethyl]-7-(3-fluoropiperidin-1-yl)-5-methylpyrazolo[1,5-a]pyrimidine;

2-[1-(4-chlorophenyl)ethyl]-7-(3,3-difluoropiperidin-1-yl)-5-methylpyrazol[1,5-a]pyrimidine;

N-tert-butyl-2-[1-(4-chlorophenyl)ethyl]-5-methylpyrazol[1,5-a]pyrimidin-7-amine;

2-[1-(4-chlorophenyl)ethyl]-5-methyl-7-(2-oxa-7-azaspiro[3.5]non-7-yl)pyrazolo[1,5-a]pyrimidine;

(3S)-1-{2-[1-(4-chlorophenyl)ethyl]-5-methylpyrazolo[1,5-a]pyrimidin-7-yl}piperidin-3-ol;

(3R)-1-{2-[1-(4-chlorophenyl)ethyl]-5-methylpyrazolo[1,5-a]pyrimidin-7-yl}piperidin-3-ol;

7-(azetidin-1-yl)-2-[1-(4-chlorophenyl)ethyl]-5-methylpyrazolo[1,5-a]pyrimidine;

2-[1-(4-chlorophenyl)ethyl]-5-methyl-7-(7-oxa-2-azaspiro[3.5]non-2-yl)pyrazolo[1,5-a]pyrimidine;

2-[1-(4-chlorophenyl)ethyl]-N-(3-fluorocyclobutyl)-5-methylpyrazolo[1,5-a]pyrimidin-7-amine;

(2R,3R)-1-{2-[1-(4-chlorophenyl)ethyl]-5-methylpyrazolo[1,5-a]pyrimidin-7-yl}-3-ethylazetidine-2-carboxylic acid;

2-[1-(4-chlorophenyl)ethyl]-N-[(3,3-difluorocyclobutyl)methyl]-5-methylpyrazolo[1,5-a]pyrimidin-7-amine;

N-[(3S)-1-{2-[1-(4-chlorophenyl)ethyl]-5-methylpyrazolo[1,5-a]pyrimidin-7-yl}pyrrolidin-3-yl]acetamide;
cis-3-({2-[1-(4-chlorophenyl)ethyl]-5-methylpyrazolo[1,5-a]pyrimidin-7-yl}amino)cyclobutanol;
trans-3-({2-[1-(4-chlorophenyl)ethyl]-5-methylpyrazolo[1,5-a]pyrimidin-7-yl}amino)cyclobutanol;
6-{2-[1-(4-chlorophenyl)ethyl]-5-methylpyrazolo[1,5-a]pyrimidin-7-yl}-6-azaspiro[3.4]octan-1-ol;
2-[1-(4-chlorophenyl)ethyl]-N-(3,3-difluorocyclobutyl)-5-methylpyrazolo[1,5-a]pyrimidin-7-amine;
2-[1-(4-chlorophenyl)ethyl]-7-[(2R)-2-ethylpiperidin-1-yl]-5-methylpyrazolo[1,5-a]pyrimidine;
N-[(3R)-1-{2-[1-(4-chlorophenyl)ethyl]-5-methylpyrazolo[1,5-a]pyrimidin-7-yl}pyrrolidin-3-yl]acetamide;
2-(1-{2-[1-(4-chlorophenyl)propyl]-5-methylpyrazolo[1,5-a]pyrimidin-7-yl}piperidin-2-yl)ethanol;
2-[1-(4-chlorophenyl)propyl]-7-(3,3-difluoropiperidin-1-yl)-5-methylpyrazolo[1,5-a]pyrimidine;
2-(1-{2-[1-(4-chlorophenyl)-2-methylpropyl]-5-methylpyrazolo[1,5-a]pyrimidin-7-yl}piperidin-2-yl)ethanol;
2-[1-(4-chlorophenyl)-2-methylpropyl]-7-(3,3-difluoropiperidin-1-yl)-5-methylpyrazolo[1,5-a]pyrimidine;
2-(1-{2-[1-(4-chlorophenyl)butyl]-5-methylpyrazolo[1,5-a]pyrimidin-7-yl}piperidin-2-yl)ethanol;
2-[1-(4-chlorophenyl)butyl]-7-(3,3-difluoropiperidin-1-yl)-5-methylpyrazolo[1,5-a]pyrimidine;
2-(1-{5-methyl-2-[3-(trifluoromethyl)benzyl]pyrazolo[1,5-a]pyrimidin-7-yl}piperidin-2-yl)ethanol;
2-{1-[5-methyl-2-(tricyclo[3.3.1.1$^{3,7}$]dec-1-ylmethyl)pyrazolo[1,5-a]pyrimidin-7-yl]piperidin-2-yl}ethanol;
(2S)-1-(5-methyl-2-{1-[4-(trifluoromethyl)phenyl]ethyl}pyrazolo[1,5-a]pyrimidin-7-yl)azetidine-2-carboxamide;
2-[1-(5-methyl-2-{1-[4-(trifluoromethyl)phenyl]ethyl}pyrazolo[1,5-a]pyrimidin-7-yl)piperidin-2-yl]ethanol;
5-methyl-7-(2-oxa-6-azaspiro[3.4]oct-6-yl)-2-{1-[4-(trifluoromethyl)phenyl]ethyl}pyrazolo[1,5-a]pyrimidine;
5-methyl-7-(7-oxa-2-azaspiro[3.5]non-2-yl)-2-{1-[4-(trifluoromethyl)phenyl]ethyl}pyrazolo[1,5-a]pyrimidine;
(3R)-1-(5-methyl-2-{1-[4-(trifluoromethyl)phenyl]ethyl}pyrazolo[1,5-a]pyrimidin-7-yl)piperidin-3-ol;
N-(3-fluorocyclobutyl)-5-methyl-2-{1-[4-(trifluoromethyl)phenyl]ethyl}pyrazolo[1,5-a]pyrimidin-7-amine;
N-[(3S)-1-(5-methyl-2-{1-[4-(trifluoromethyl)phenyl]ethyl}pyrazolo[1,5-a]pyrimidin-7-yl)pyrrolidin-3-yl]acetamide;
5-methyl-N-(1-methylcyclopropyl)-2-{1-[4-(trifluoromethyl)phenyl]ethyl}pyrazolo[1,5-a]pyrimidin-7-amine;
[1-(5-methyl-2-{1-[4-(trifluoromethyl)phenyl]ethyl}pyrazolo[1,5-a]pyrimidin-7-yl)piperidin-2-yl]methanol;
(2S)-1-(5-methyl-2-{1-[4-(trifluoromethyl)phenyl]ethyl}pyrazolo[1,5-a]pyrimidin-7-yl)azetidine-2-carboxylic acid;
7-(4-fluoropiperidin-1-yl)-5-methyl-2-{1-[4-(trifluoromethyl)phenyl]ethyl}pyrazolo[1,5-a]pyrimidine;
7-(3-fluoropiperidin-1-yl)-5-methyl-2-{1-[4-(trifluoromethyl)phenyl]ethyl}pyrazolo[1,5-a]pyrimidine;
3-(2-hydroxyethyl)-4-(5-methyl-2-{1-[4-(trifluoromethyl)phenyl]ethyl}pyrazolo[1,5-a]pyrimidin-7-yl)piperazin-2-one;
N-[(3,3-difluorocyclobutyl)methyl]-5-methyl-2-{1-[4-(trifluoromethyl)phenyl]ethyl}pyrazolo[1,5-a]pyrimidin-7-amine;
7-(3,3-difluoropyrrolidin-1-yl)-5-methyl-2-{1-[4-(trifluoromethyl)phenyl]ethyl}pyrazolo[1,5-a]pyrimidine;
N-[(3R)-1-(5-methyl-2-{1-[4-(trifluoromethyl)phenyl]ethyl}pyrazolo[1,5-a]pyrimidin-7-yl)pyrrolidin-3-yl]acetamide;
7-(3,3-difluoropiperidin-1-yl)-5-methyl-2-{1-[4-(trifluoromethyl)phenyl]ethyl}pyrazolo[1,5-a]pyrimidine;
1-(5-methyl-2-{1-[4-(trifluoromethyl)phenyl]ethyl}pyrazolo[1,5-a]pyrimidin-7-yl)piperidin-2-one;
N-tert-butyl-5-methyl-2-{1-[4-(trifluoromethyl)phenyl]ethyl}pyrazolo[1,5-a]pyrimidin-7-amine;
N-(3,3-difluorocyclobutyl)-5-methyl-2-{1-[4-(trifluoromethyl)phenyl]ethyl}pyrazolo[1,5-a]pyrimidin-7-amine;
5-methyl-7-(2-oxa-7-azaspiro[3.5]non-7-yl)-2-{1-[4-(trifluoromethyl)phenyl]ethyl}pyrazolo[1,5-a]pyrimidine;
1-(5-methyl-2-{1-[4-(trifluoromethyl)phenyl]ethyl}pyrazolo[1,5-a]pyrimidin-7-yl)pyrrolidine-3-carboxamide;
(1-{2-[1-(5-chloropyridin-2-yl)ethyl]-5-methylpyrazolo[1,5-a]pyrimidin-7-yl}piperidin-3-yl)methanol;
2-[1-(5-chloropyridin-2-yl)ethyl]-N-(3,3-difluorocyclobutyl)-5-methylpyrazolo[1,5-a]pyrimidin-7-amine;
(3S)-1-{2-[1-(5-chloropyridin-2-yl)ethyl]-5-methylpyrazolo[1,5-a]pyrimidin-7-yl}piperidin-3-ol;
2-[1-(5-chloropyridin-2-yl)ethyl]-7-(3,3-difluoropiperidin-1-yl)-5-methylpyrazolo[1,5-a]pyrimidine;
2-[1-(5-chloropyridin-2-yl)ethyl]-7-(3,3-difluoropyrrolidin-1-yl)-5-methylpyrazolo[1,5-a]pyrimidine;
N-tert-butyl-2-[1-(5-chloropyridin-2-yl)ethyl]-5-methylpyrazolo[1,5-a]pyrimidin-7-amine;
2-[1-(5-chloropyridin-2-yl)ethyl]-5-methyl-N-(1-methylcyclopropyl)pyrazolo[1,5-a]pyrimidin-7-amine;
2-[1-(5-chloropyridin-2-yl)ethyl]-N-(3-fluorocyclobutyl)-5-methylpyrazolo[1,5-a]pyrimidin-7-amine;
2-[1-(5-chloropyridin-2-yl)ethyl]-5-methyl-7-(7-oxa-2-azaspiro[3.5]non-2-yl)pyrazolo[1,5-a]pyrimidine;
N-[(3R)-1-{2-[1-(5-chloropyridin-2-yl)ethyl]-5-methylpyrazolo[1,5-a]pyrimidin-7-yl}pyrrolidin-3-yl]acetamide;
N-[(3S)-1-{2-[1-(5-chloropyridin-2-yl)ethyl]-5-methylpyrazolo[1,5-a]pyrimidin-7-yl}pyrrolidin-3-yl]acetamide;
N-{(3R)-1-[2-(4-chlorobenzyl)-5-methylpyrazolo[1,5-a]pyrimidin-7-yl]pyrrolidin-3-yl}methanesulfonamide;
N-{(3S)-1-[2-(4-chlorobenzyl)-5-methylpyrazolo[1,5-a]pyrimidin-7-yl]piperidin-3-yl}methanesulfonamide; and
2-{1-[2-(3-chlorobenzyl)-5-methylpyrazolo[1,5-a]pyrimidin-7-yl]piperidin-2-yl}ethanol.

Compound names are assigned by using Name 2014 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1)

attachment of a mixture of enantiomers to a chiral auxiliary, separation of the resulting mixture of diastereomers by recrystallization or chromatography and optional liberation of the optically pure product from the auxiliary as described in Fumrniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Present compounds may be used in the form of pharmaceutically acceptable salts. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of the invention may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The invention contemplates compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-2. In Schemes 1-2, the variables $R^1$, $R^2$, $R^3$, $R^4$, $G^1$, and $L^1$ are as described in the Summary.

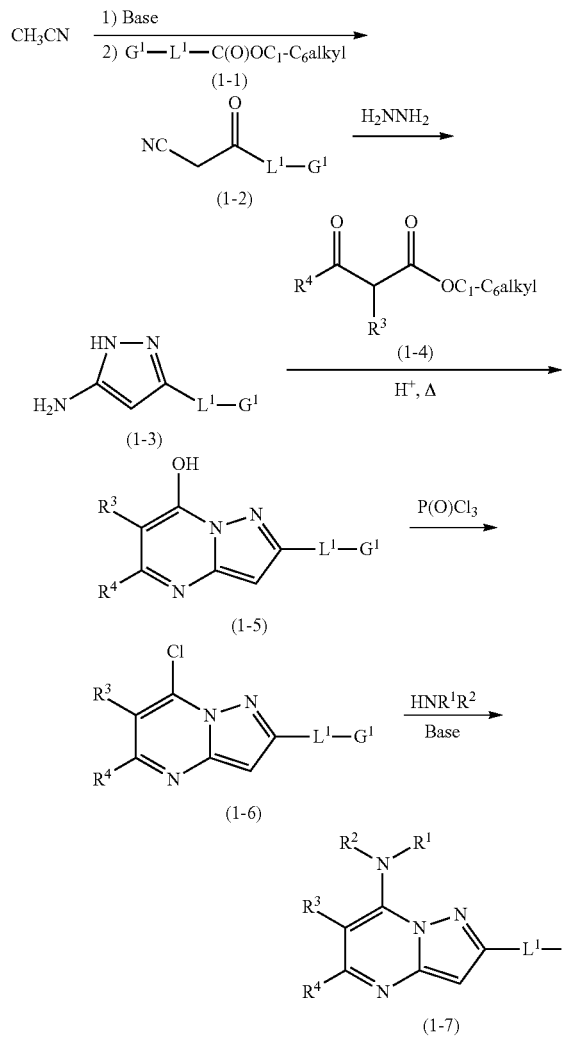

As shown in Scheme 1, compounds of formula (1-7) can be prepared starting from acetonitrile and compounds of formula (1-1). Accordingly, acetonitrile can be treated with a base, such as but not limited to n-butyllithium, in a solvent such as tetrahydrofuran at −70 to −80° C. over 15 to 120 minutes. The anion of acetonitrile can then be reacted with compounds of formula (1-1) initially at −70 to −80° C. followed by gradual warming over 4 to 24 hours to give compounds of formula (1-2). Compounds of formula (1-2) can be reacted with hydrazine or hydrazine hydrate in ethanol at or near the refluxing temperature over 2 to 8 hours to give compounds of formula (1-3). Compounds of formula (1-3) can then be reacted with compounds of formula (1-4) in acetic acid heated between 90° C. and the reflux temperature over 2 to 8 hours to provide compounds of formula (1-5). Compounds of formula (1-5) can be reacted with phosphoryl chloride at reflux temperature over 1 to 12 hours optionally with a co-solvent such as acetonitrile and optionally in the presence of a base such as triethylamine to give compounds of formula (1-6). Compounds of formula (1-6) can be reacted with $HNR^1R^2$ in the presence of a base in a heated solvent to give compounds of formula (1-7). Suitable bases for the conversion of compounds of formula (1-6) to compounds of formula (1-7) are potassium carbonate, sodium carbonate, cesium carbonate in the presence of potassium iodide, triethylamine or diisopropylethylamine. Suitable solvents for the conversion of compounds of formula (1-6) to compounds of formula (1-7) include but are not limited to N,N-dimethylformamide, dioxane, ethanol or acetonitrile heated conventionally from 40-135° C. over 4 to 36 hours dependent on the particular solvent used. The heating can also be achieved with microwave irradiation in a sealed vessel heated between 100-160° C. over 30 to 150 minutes. Compounds of formula (1-7) are representative of compounds of formula (I).

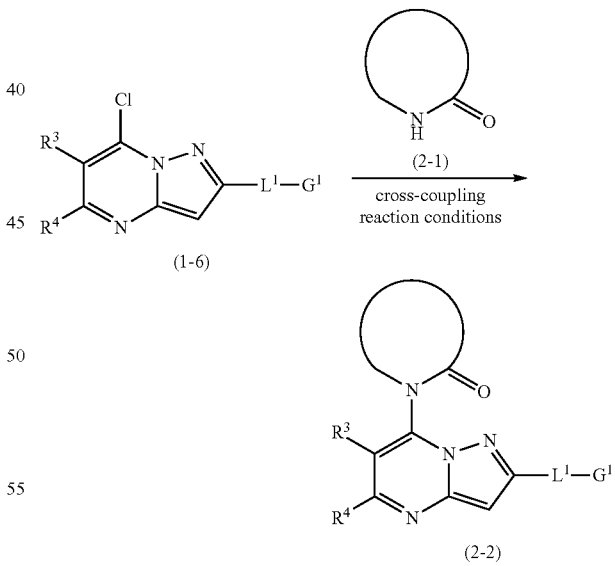

As shown in Scheme 2, compounds of formula (2-2) can be prepared from compounds of formula (1-6). Compounds of formula (1-6) can be reacted under palladium catalyzed cross-coupling reaction conditions with four- to seven-membered lactams of formula (2-1) which are optionally substituted as described for $R^1$ and $R^2$. For example, compounds of formula (1-6) can be coupled with compounds of formula (2-1) in the presence of a palladium catalyst such as tris(dibenzylideneacetone)dipalladium(0) (Pd$_2$(dba)$_3$) or palladium(II) acetate, a phosphine ligand such as 2-dicyclohexylphosphino-2',4',6'-triisopropylbiphenyl (XPhos) or (9,9-dimethyl-9H-xanthene-4,5-diyl)bis(diphenylphosphine) (Xantphos), and a base such as cesium carbonate heated either conventionally or with microwave irradiation in a solvent such as N,N-dimethylformamide or dioxane to give compounds of formula (2-2). Compounds of formula (2-2) are representative of compounds of formula (I).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Fumrniss, Hannaford, Smith, and Tatchell, pub. Longman Scientific & Technical, Essex CM20 2JE, England.

Many of the compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Pharmaceutical Compositions

This invention also provides for pharmaceutical compositions comprising a therapeutically effective amount of a compound of formula (I), or a pharmaceutically acceptable salt thereof together with a pharmaceutically acceptable carrier, diluent, or excipient thereof. The phrase "pharmaceutical composition" refers to a composition suitable for administration in medical or veterinary use.

The pharmaceutical compositions that comprise a compound of formula (I), alone or in combination with a second therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogenfree water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I). In certain embodiments, the compound of formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Methods of Use

The compounds and compositions using any amount and any route of administration may be administered to a subject for the treatment or prevention of pain, substance abuse (especially in alcohol dependence), or spasticity.

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, via implantation, transdermally, topically, and via implantation. In certain embodiments, the compounds and compositions thereof may be delivered orally. The compounds may also be delivered rectally, bucally, intravaginally, ocularly, or by insufflation. GABA-B modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as positive allosteric modulators of GABA-B. Thus, the compounds and compositions are particularly useful for treating or lessening the severity, or progression of a disease, disorder, or a condition where the GABA-B receptor is involved. Accordingly, the invention provides a method for treating of pain, substance abuse (especially in alcohol dependence), or spasticity in a subject, wherein the method comprises the step of administering to said subject a therapeutically effective amount of a compound of formula (I) or a preferred embodiment thereof as set forth above, with or without a pharmaceutically acceptable carrier. Particularly, the method is for the treatment or prevention of pain.

The invention also relates to a compound according to formula (I) or a pharmaceutically acceptable salt thereof for use in medicine.

The invention further relates to a compound according to formula (I) or a pharmaceutically acceptable salt thereof for use in the treatment of pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus.

The invention further relates to the use of a compound according to formula (I) or a pharmaceutically acceptable salt thereof in the preparation of a medicament.

The invention further relates to the use of a compound according to formula (I) in the preparation of a medicament for use in the treatment of pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus.

The present compounds may be co-administered to a subject. The term "co-administered" means the administration of two or more different therapeutic agents that are administered to a subject by combination in the same pharmaceutical composition or separate pharmaceutical compositions. Thus co-administration involves administration at the same time of a single pharmaceutical composition comprising two or more therapeutic agents or administration of two or more different compositions to the same subject at the same or different times.

The compounds of the invention may be co-administered with a therapeutically effective amount of one or more agents to treat pain, where examples of the agents include, nonsteroidal anti-inflammatory drugs (NSAIDs), opioid analgesics, barbiturates, benzodiazapines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-HT$_{2A}$ receptor antagonists, cholinergic analgesics, α$_2$δ ligands (such as gabapentin or pregabalin), cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin E$_2$ subtype 4 antagonists, leukotriene B4 antagonists, 5-lipoxygenase inhibitors, sodium channel blockers, 5-HT$_3$ antagonists, N-methyl-D-aspartic acid receptor antagonists, phosphodiesterase V inhibitors, voltage-gated calcium channel blockers (e.g., N-type and T-type), and KCNQ openers (e.g., KCNQ2/3 (K$_v$7.2/3)).

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, modulate the γ-aminobutyric acid receptor, and treat a disease treatable by modulating the γ-aminobutyric acid receptor (including pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus).

This invention also is directed to a use of one or more compounds and/or salts of the invention in the preparation of a medicament. The medicament optionally can comprise one or more additional therapeutic agents. In some embodiments, the medicament is useful for treating pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus.

This invention also is directed to a use of one or more compounds and/or salts of the invention in the manufacture of a medicament for the treatment of pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus. The medicament optionally can comprise one or more additional therapeutic agents.

Further benefits of Applicants' invention will be apparent to one skilled in the art from reading this patent application.

The following Examples may be used for illustrative purposes and should not be deemed to narrow the scope of the invention.

EXAMPLES

Abbreviations: d for day; h for hour; DMSO for dimethyl sulfoxide; ESI for electrospray ionization; Et for ethyl; LC-MS for liquid chromatography/mass spectrometry; room temperature (20-25° C.);

I. Preparation of Intermediates

The starting materials used in the examples are either commercially available or can be synthesized by the average skilled person trained in organic chemistry following routine laboratory practice as outlined, for example in the examples below.

Intermediate a1: 7-chloro-2-(4-chlorobenzyl)-5-methylpyrazolo[1,5-a]pyrimidine a1.1) 3-(4-chlorobenzyl)-1H-pyrazol-5-amine A mixture of 4-(4-chlorophenyl)-3-oxobutanenitrile (1955 mg, 10.10 mmol) and hydrazine monohydrate (1011 mg, 20.19 mmol) in ethanol (30 mL) was refluxed for 3 h. For work-up, the reaction mixture was partitioned between water and ethyl acetate. The combined organic layers were washed with 50% aqueous NaHCO$_3$ solution and brine, dried over MgSO$_4$, and concentrated in vacuo to give the titled compound (1.6 g, 76%). LC-MS (ESI+) m/z 208.1 [M+H]$^+$.

a1.2) 2-(4-chlorobenzyl)-5-methylpyrazolo[1,5-a]pyrimidin-7-ol

A mixture of compound a1.1 (1.6 g, 7.70 mmol) and ethyl 3-oxobutanoate (1.504 g, 11.56 mmol) in acetic acid (30 mL) was refluxed for 3 h. Then, the reaction mixture was concentrated, and the residue was dissolved in dichloromethane. The resultant solid was collected by filtration and dried in vacuo overnight to give the titled compound (2.10 g, 100%). LC-MS (ESI+) m/z 274.1 [M+H]$^+$.

a1.3) 7-chloro-2-(4-chlorobenzyl)-5-methylpyrazolo[1,5-a]pyrimidine

A mixture of compound a1.2 (2.1 g, 7.67 mmol) in phosphoryl trichloride (24.68 g, 15 mL, 161 mmol) was refluxed for 2 h. The reaction mixture was then slowly poured into water (exothermic reaction) with a temperature increase from room temperature to 35° C. observed. The solution was extracted with dichloromethane, and the organic layers were dried over MgSO$_4$ and concentrated. The residue was dissolved in ethyl acetate, and the insoluble residues (R1) were filtered off. The filtrate (F1) was concentrated, and the residue was triturated with ethyl acetate: diisopropyl ether (1:1) to separate the remaining solids (R2) from the triturate (F2). R1 and F2 were combined and purified chromatographically using a Teledyne Isco RediSep® silica gel cartridge (12 g) on a Teledyne Isco CombiFlash® system eluted with 20% ethyl acetate/cyclohexane (27 mL/minute) to obtain the titled compound (1.6 g, 71.4%). LC-MS (ESI+) m/z 292.0 [M+H]$^+$.

Intermediate a2) 7-chloro-2-[1-(4-chlorophenyl)ethyl]-5-methylpyrazolo[1,5-a]pyrimidine a2.1) 4-(4-chlorophenyl)-3-oxopentanenitrile A solution of butyllithium (1.6 M in hexane, 8.65 mL, 0.887 g, 13.84 mmol) in tetrahydrofuran (30 mL) was cooled to −75° C., and a solution of acetonitrile (0.568 g, 13.84 mmol) in tetrahydrofuran (3 mL) was added dropwise. After addition, the solution was stirred for another 90 minutes at −75° C. To the obtained white suspension, a solution of methyl 2-(4-chlorophenyl)propanoate (2.50 g, 12.59 mmol) in tetrahydrofuran (10 mL) was added at −75° C., and the reaction mixture was stirred overnight and allowed to warm to room temperature. The mixture was then partitioned between 80% aqueous $NH_4Cl$ solution and ethyl acetate. The organic phases were washed with water and brine, dried over $MgSO_4$, filtered, and concentrated in vacuo to give the titled compound (2.45 g, 94%). LC-MS (ESI+) m/z 208.1 $[M+H]^+$.

a2.2)
3-[1-(4-chlorophenyl)ethyl]-1H-pyrazol-5-amine

The synthesis was done analogously to the synthesis of intermediate a1.1 to give the titled compound (100%). LC-MS (ESI+) m/z 222.1 $[M+H]^+$.

a2.3) 2-[1-(4-chlorophenyl)ethyl]-5-methylpyrazolo[1,5-a]pyrimidin-7-ol

The reaction was done analogously to the synthesis of intermediate a1.2. For workup, the reaction mixture was stirred with water (60 mL) and diisopropyl ether (20 mL). The resultant solids were collected by filtration, washed with additional diisopropyl ether, and dried in a vacuum oven overnight to give the titled compound (63.3%). LC-MS (ESI+) m/z 288.0 $[M+H]^+$.

a2.4) 7-chloro-2-[1-(4-chlorophenyl)ethyl]-5-methylpyrazolo[1,5-a]pyrimidine

A mixture of compound a2.3 (2.4 g, 8.34 mmol) and phosphoryl trichloride (3.84 g, 2.33 mL, 25.02 mmol) in acetonitrile (15 mL) was refluxed for 8 h. The reaction mixture was quenched with water. The mixture was then partitioned between ethyl acetate and 50% aqueous sodium bicarbonate. The organic fraction was washed with 50% aqueous sodium bicarbonate, dried over $MgSO_4$, and concentrated. The residue was purified chromatographically using a Teledyne Isco RediSep® silica gel cartridge (40 g) on a Teledyne Isco CombiFlash® system eluted with a gradient of 2-3.5% methanol/dichloromethane (35 mL/minute) to obtain the titled compound (2.4 g, 94%). LC-MS (ESI+) m/z 306.0 $[M+H]^+$.

Intermediate a3) 7-chloro-2-[1-(4-chlorophenyl) propyl]-5-methylpyrazolo[1,5-a]pyrimidine a3.1) 4-(4-chlorophenyl)-3-oxohexanenitrile A solution of butyllithium (6.57 mL, 10.34 mmol, 1.6 M in hexane) in tetrahydrofuran (30 mL) was cooled to −75° C., and at this temperature, a solution of acetonitrile (0.540 mL, 10.34 mmol) in tetrahydrofuran (3 mL) was added dropwise. The resultant mixture was stirred for 90 minutes at −75° C. producing a white suspension. Then a solution of methyl 2-(4-chlorophenyl)butanoate (2.00 g, 9.40 mmol) in tetrahydrofuran (10 mL) was slowly added at −75° C., and the reaction mixture was allowed to gradually warm to ambient temperature with continued stirring overnight. The reaction mixture was then partitioned between ethyl acetate and 80% aqueous ammonium chloride. The ethyl acetate fraction was subsequently washed with water and brine, dried over magnesium sulfate, and filtered. The filtrate was concentrated under reduced pressure to provide the titled compound (2.1 g, 100%). MS (ESI+) m/z 222.1 $[M+H]^+$.

a3.2)
3-[1-(4-chlorophenyl)propyl]-1H-pyrazol-5-amine

A mixture of 4-(4-chlorophenyl)-3-oxohexanenitrile (2.1 g, 9.47 mmol, a3.1), hydrazine hydrate (0.929 mL, 18.95 mmol), and ethanol (30 mL) was stirred at the reflux temperature for 3 hours. The reaction mixture was then partitioned between ethyl acetate and water. The organic phase was subsequently washed with saturated aqueous sodium bicarbonate solution and brine, dried over magnesium sulfate, and filtered. The filtrate was concentrated under reduced pressure to provide the titled compound (2.6 g, 100%). LC-MS (ESI+) m/z 236.1 $[M+H]^+$.

a3.3) 2-[1-(4-chlorophenyl)propyl]-5-methylpyrazolo[1,5-a]pyrimidin-7-ol

A mixture of 3-[1-(4-chlorophenyl)propyl]-1H-pyrazol-5-amine (2.23 g, 9.46 mmol, a3.2), ethyl acetoacetate (1.795 mL, 14.19 mmol), and acetic acid (30 mL) was stirred for 3 hours at the reflux temperature. The reaction mixture was partitioned between water (60 mL) and ethyl acetate (20 mL). The organic fraction was subsequently washed with water and 50% aqueous sodium bicarbonate. A precipitate was noted in the organic fraction. The organic fraction was concentrated under reduced pressure, and the residue was stirred with diisopropyl ether. The resultant solid was collected by filtration, washed with diisopropyl ether, and dried overnight in a vacuum oven at 40° C. to give the titled compound (1.785 g, 62.5%). LC-MS (ESI+) m/z 302.2 $[M+H]^+$.

a3.4) 7-chloro-2-[1-(4-chlorophenyl)propyl]-5-methylpyrazolo[1,5-a]pyrimidine

A mixture of 2-[1-(4-chlorophenyl)propyl]-5-methylpyrazolo[1,5-a]pyrimidin-7-ol (1.785 g, 5.92 mmol, a3.3), phosphoryl trichloride (1.654 mL, 17.75 mmol) and acetonitrile (30 mL) was stirred at the reflux temperature for 8 hours. The reaction was quenched with water. The mixture was partitioned between a 50% aqueous sodium bicarbonate solution and ethyl acetate. The organic phase was then washed with 50% aqueous sodium bicarbonate solution, dried over $MgSO_4$, and concentrated under reduced pressure. The residue was chromatographically purified (Teledyne Isco CombiFlash® Rf, 40 g RediSep® silica gel cartridge eluted with a linear gradient of 2-3.5% methanol/dichloromethane over 7 minutes, flow rate 35 mL/minute) to provide the titled compound (1.8 g, 95%). LC-MS ($ESI^+$) m/z 320.2 $[M+H]^+$.

Intermediate a4) 7-chloro-2-[1-(4-chlorophenyl)-2-methylpropyl]-5-methylpyrazolo[1,5-a]pyrimidine a4.1)
4-(4-chlorophenyl)-5-methyl-3-oxohexanenitrile The synthesis was done analogously to the synthesis of intermediate a2.1 to give the titled compound (100%).

a4.2) 3-[1-(4-chlorophenyl)-2-methylpropyl]-1H-pyrazol-5-amine

The synthesis was done analogously to the synthesis of intermediate a1.1 to give the titled compound (100%). LC-MS (ESI+) m/z 250.2 [M+H]$^+$.

a4.3) 2-[1-(4-chlorophenyl)-2-methylpropyl]-5-methylpyrazolo[1,5-a]pyrimidin-7-ol The synthesis was done analogously to the synthesis of intermediate a3.3. For workup, the reaction mixture was partitioned between water and ethyl acetate. The organic fraction was washed with brine, dried over MgSO$_4$, filtered, and concentrated. The residue was chromatographically purified (Teledyne Isco CombiFlash® Rf, 40 g RediSep® silica gel cartridge eluted with a linear gradient of 2-3.5% methanol/dichloromethane, flow rate 35 mL/minute) to provide the titled compound (55.2%). MS (ESI+) m/z 316.2 [M+H]$^+$.

a4.4) 7-chloro-2-[1-(4-chlorophenyl)-2-methylpropyl]-5-methylpyrazolo[1,5-a]pyrimidine The synthesis and extractive workup were done analogously to the synthesis of intermediate a3.4. The resultant residue was chromatographically purified (Teledyne Isco CombiFlash® Rf, 24 g RediSep® silica gel cartridge eluted with a linear gradient of 2-3.5% methanol/dichloromethane, flow rate 28 mL/minute) to provide the titled compound (63.0%) which was stored in a refrigerator. LC-MS (ESI+) m/z 334.2 [M+H]$^+$.

Intermediate a5) 7-chloro-2-[1-(4-chlorophenyl)butyl]-5-methylpyrazolo[1,5-a]pyrimidine The synthesis was done analogously to the synthesis of INTERMEDIATE a2. The titled compound was obtained as yellow oil that was stored in the refrigerator. LC-MS (ESI+) m/z 334.2 [M+H]$^+$.

Intermediate a6: 7-chloro-5-methyl-2-[3-(trifluoromethyl)benzyl]pyrazolo[1,5-a]pyrimidine a6.1) 3-oxo-4-[3-(trifluoromethyl)phenyl]butanenitrile

A solution of butyllithium (1.6 M in hexane, 8.02 mL, 12.83 mmol) in tetrahydrofuran (30 mL) was cooled to −75° C., and a solution of acetonitrile (0.737 mL, 13.84 mmol) in tetrahydrofuran (3 mL) was added dropwise. After addition, the solution was stirred for another 90 minutes at −75° C. To the obtained white suspension, a solution of methyl 2-(3-(trifluoromethyl)phenyl)acetate (2.80 g, 12.83 mmol) in tetrahydrofuran (10 mL) was added at −75° C., and the reaction mixture was stirred overnight and allowed to warm to room temperature. The mixture was then partitioned between 80% aqueous NH$_4$Cl solution and ethyl acetate. The combined organic phases were washed with water and brine, dried over MgSO$_4$, filtered, and concentrated in vacuo. The residue was purified chromatographically using a Teledyne Isco RediSep® silica gel cartridge (24 g) on a Teledyne Isco CombiFlash® system eluted with 25% ethyl acetate/cyclohexane (28 mL/minute) to obtain the titled compound (1.0 g, 34.3%). LC-MS (ESI+) m/z 250.0 [M+Na]$^+$.

a6.2) 3-[3-(trifluoromethyl)benzyl]-1H-pyrazol-5-amine

The synthesis was done analogously to the synthesis of intermediate a1.1. The titled compound was obtained as brown solid (100%). LC-MS (ESI+) m/z 242.0 [M+H]$^+$.

a6.3) 5-methyl-2-[3-(trifluoromethyl)benzyl]pyrazolo[1,5-a]pyrimidin-7-ol

A mixture of compound a6.2 (1060 mg, 4.39 mmol) and ethyl 3-oxobutanoate (858 mg, 6.59 mmol) in acetic acid (10 mL) was refluxed for 3 h. For work-up, the reaction mixture was poured in water (40 mL), and the precipitate was collected by filtration and washed with diisopropyl ether. The titled compound was obtained after drying in vacuo as a solid (1030 mg, 76%). LC-MS (ESI+) m/z 308.1 [M+H]$^+$.

a6.4) 7-chloro-5-methyl-2-[3-(trifluoromethyl)benzyl]pyrazolo[1,5-a]pyrimidine A mixture of compound a6.3 (1020 mg, 3.32 mmol) and phosphoryl trichloride (1018 mg, 0.619 mL, 6.64 mmol) in acetonitrile (15 mL) was refluxed for 8 h. For work-up, water was added to the reaction mixture, and the mixture was partitioned between 50% aqueous NaHCO$_3$ solution and ethyl acetate. The organic layers were washed with 50% aqueous NaHCO$_3$, dried over MgSO$_4$, and concentrated in vacuo. The residue was purified chromatographically using a Teledyne Isco RediSep® silica gel cartridge (12 g) on a Teledyne Isco CombiFlash® system eluted with a gradient of 2-5% methanol/dichloromethane (30 mL/minute) to obtain the titled compound (880 mg, 81%). LC-MS (ESI+) m/z 326.0 [M+H]$^+$.

Intermediate a7: 7-chloro-5-methyl-2-(tricyclo[3.3.1.1$^{3,7}$]dec-1-ylmethyl)pyrazolo[1,5-a]pyrimidine a7.1) 3-oxo-4-(tricyclo[3.3.1.1$^{3,7}$]dec-1-yl)butanenitrile

A solution of butyllithium (1.6 M in hexane, 6.00 mL, 9.60 mmol) in tetrahydrofuran (30 mL) was cooled to −75° C., and a solution of acetonitrile (0.552 mL, 10.56 mmol) in tetrahydrofuran (3 mL) was added dropwise. After addition, the solution was stirred for another 90 minutes at −75° C. To the obtained white suspension, a solution of methyl 2-(adamantan-1-yl)acetate (2.00 g, 9.60 mmol) in tetrahydrofuran (10 mL) was added at −75° C., and the reaction mixture was stirred overnight and allowed to warm to room temperature. The mixture was then partitioned between 80% aqueous NH$_4$Cl solution and ethyl acetate. The organic phases were washed with water and brine, dried over MgSO$_4$, filtered, and concentrated in vacuo. The residue was purified chromatographically using a Teledyne Isco RediSep® silica gel cartridge (40 g) on a Teledyne Isco CombiFlash® system eluted with 25% ethyl acetate/cyclohexane (28 mL/minute) to obtain the titled compound (780 mg, 37.4%). LC-MS (ESI+) m/z 218.2 [M+H]$^+$.

a7.2) 3-(tricyclo[3.3.1.1$^{3,7}$]dec-1-ylmethyl)-1H-pyrazol-5-amine

The synthesis was done analogously to the synthesis of intermediate a1.1. The titled compound was obtained as an off-white solid (100%). LC-MS (ESI+) m/z 232.2 [M+H]$^+$.

a7.3) 5-methyl-2-(tricyclo[3.3.1.1³,⁷]dec-1-ylm-ethyl)pyrazolo[1,5-a]pyrimidin-7-ol A mixture of compound a7.2 (830 mg, 3.59 mmol) and ethyl 3-oxobutanoate (700 mg, 5.38 mmol) in acetic acid (10 mL) was refluxed for 3 h. For workup, the reaction mixture was stirred with water (40 mL). The resultant solids were collected by filtration, washed with diisopropyl ether, and dried in a vacuum oven overnight to give the titled compound (900 mg, 84%). LC-MS (ESI+) m/z 298.2 [M+H]$^+$.

a7.4) 7-chloro-5-methyl-2-(tricyclo[3.3.1.1³,⁷]dec-1-ylmethyl)pyrazolo[1,5-a]pyrimidine A mixture of compound a7.3 (900 mg, 3.03 mmol) and phosphoryl trichloride (928 mg, 0.564 mL, 6.05 mmol) in acetonitrile (15 mL) was refluxed for 8 h. Water was then added to the reaction mixture. The mixture was then partitioned between ethyl acetate and 50% aqueous sodium bicarbonate. The organic fraction was washed with 50% aqueous sodium bicarbonate, dried over MgSO$_4$, and concentrated. The residue was purified chromatographically using a Teledyne Isco RediSep® silica gel cartridge (12 g) on a Teledyne Isco CombiFlash® system eluted with a gradient of 2-5% methanol/dichloromethane (30 mL/minute) to obtain the titled compound (650 mg, 71.1%). LC-MS (ESI+) m/z 316.2 [M+H]$^+$.

Intermediate a8): 7-chloro-5-methyl-2-{1-[4-(trifluoromethyl)phenyl]ethyl}pyrazolo[1,5-a]pyrimidine a8.1) ethyl 2-[4-(trifluoromethyl)phenyl]propanoate Sodium bis(trimethylsilyl)amide (1.895 g, 10.34 mmol) was added dropwise into a solution of ethyl [4-(trifluoromethyl)phenyl]acetate (2.0 g, 8.61 mmol) in tetrahydrofuran (40 mL) at −78° C. under an atmosphere of nitrogen. After stirring for 10 minutes, a solution of iodomethane (1.345 g, 9.47 mmol) in tetrahydrofuran (3 mL) was added. The reaction mixture was stirred at −50° C. for 2 hours. Water and ethyl acetate were added, the organic layer was separated, and the aqueous layer was extracted with ethyl acetate. The combined organic layers were washed with water and dried over sodium sulfate. After filtration and concentration under reduced pressure, the crude product was distilled under vacuum to give the titled compound (1.6 g, 75%). $^1$H NMR (400 MHz, CDCl$_3$) δ ppm 1.21 (t, 3H), 1.51 (d, 3H), 3.77 (q, 1H), 4.15 (m, 2H), 7.42 (d, 2H), 7.57 (d, 2H).

a8.2) 3-oxo-4-[4-(trifluoromethyl)phenyl]pentanenitrile

Acetonitrile (0.367 g, 8.93 mmol) was added dropwise into the solution of butyllithium (0.572 g, 8.93 mmol) in tetrahydrofuran (5 mL) at −78° C. under an atmosphere of nitrogen. After stirring for 2 hours at −78° C., ethyl 2-[4-(trifluoromethyl)phenyl]propanoate (2.0 g, 8.12 mmol, a8.1) was added dropwise. The temperature was allowed to gradually arise to room temperature. Water and ethyl acetate were added, the organic layer was separated, and the aqueous layer was extracted with ethyl acetate. The combined organic layers were washed with water, dried over sodium sulfate, and concentrated under vacuum. The residue was distilled under reduced pressure to give the titled compound (1.8 g, 92%), which was used to the next step without further purification. MS (ESI+) m/z 242.1 [M+H]$^+$.

a8.3) 5-{1-[4-(trifluoromethyl)phenyl]ethyl}-1H-pyrazol-3-amine

Hydrazine hydrate (0.374 g, 7.46 mmol) was added to a solution of 3-oxo-4-[4-(trifluoromethyl)phenyl]pentanenitrile (1.8 g, 7.46 mmol, a8.2) in ethanol (20 mL). The resulting mixture was stirred at 80° C. for 4 hours. Concentration under vacuum gave the titled compound (1.7 g, 89%), which was used directly to the next step without further purification. MS (ESI+) m/z 256.0 [M+H]$^+$.

a8.4) 5-methyl-2-{1-[4-(trifluoromethyl)phenyl]ethyl}pyrazolo[1,5-a]pyrimidin-7-ol Into a solution of 5-{1-[4-(trifluoromethyl)phenyl]ethyl}-1H-pyrazol-3-amine (1.7 g, 6.66 mmol, a8.3) in acetic acid (20 mL) was added ethyl 3-oxobutanoate (0.953 g, 7.33 mmol). The resulting mixture was stirred at 100° C. for 4 hours. After concentration under vacuum, the residue was washed with water and dried in vacuo to afford the titled compound (1.7 g, 79%). MS (ESI+) m/z 322.1 [M+H]$^+$.

a8.5) 7-chloro-5-methyl-2-{1-[4-(trifluoromethyl)phenyl]ethyl}pyrazolo[1,5-a]pyrimidine 5-Methyl-2-{1-[4-(trifluoromethyl)phenyl]ethyl}pyrazolo[1,5-a]pyrimidin-7-ol (1.7 g, 5.29 mmol, a8.4) in phosphoryl trichloride (1.623 g, 10.58 mmol) and triethylamine (0.811 mL, 5.82 mmol) was heated to reflux for 2 hours. The reaction mixture was concentrated under vacuum, and the residue was poured into water/ice (50 mL). The resultant solid was collected by filtration and washed with hexane to give the titled compound (1.7 g, 95%). $^1$H NMR (400 MHz, CDCl$_3$) δ ppm 1.76 (d, 3H), 2.57 (s, 3H), 4.49 (q, 1H), 6.43 (s, 1H), 6.79 (s, 1H), 7.45 (d, 2H), 7.55 (d, 2H).

Intermediate a9): 7-chloro-2-[1-(5-chloropyridin-2-yl)ethyl]-5-methylpyrazolo[1,5-a]pyrimidine a9.1) methyl 2-(5-chloropyridin-2-yl)propanoate 2-Bromo-5-chloropyridine (1 g, 5.20 mmol) was added to a suspension of methyl 2-bromopropanoate (0.955 g, 5.72 mmol) and copper (0.759 g, 11.95 mmol) in dimethyl sulfoxide (5 mL). The mixture was stirred at 50° C. for 2 hours. After cooling to room temperature, the reaction mixture was diluted with ethyl acetate (30 mL). An aqueous solution of potassium dihydrogenphosphate (0.707 g, 5.20 mmol, 15 mL) was added, and the mixture stirred for 30 minutes before filtering. The copper salts were washed with ethyl acetate. The organic layer was washed with water, dried over sodium sulfate, filtered, and concentrated in vacuum. Purification by flash chromatography (petroleum ether/ethyl acetate) provided the titled compound (500 mg, 48.2%). MS (ESI+) m/z 200.0 [M+H]$^+$; $^1$H NMR (400 MHz, CDCl$_3$) δ ppm 1.55 (d, 3H), 3.69 (s, 3H), 3.95 (q, 1H), 7.25 (d, 1H), 7.65 (d, 1H), 8.51 (s, 1H).

a9.2) 4-(5-chloropyridin-2-yl)-3-oxopentanenitrile

Acetonitrile (103 mg, 2.505 mmol) was added dropwise into the solution of butyllithium (2 mL, 0.90 equivalents) in tetrahydrofuran (10 mL) at −78° C. under an atmosphere of nitrogen. After stirring for 0.5 hours at −78° C., methyl 2-(5-chloropyridin-2-yl)propanoate (500 mg, 2.505 mmol, a9.1) in tetrahydrofuran (5 mL) was added dropwise. The temperature was allowed to gradually rise to room temperature. The resulting solution was stirred overnight at room temperature and then quenched by the addition of water. The pH value of the solution was adjusted to 5 with 1 N hydrochloric acid. The resulting solution was extracted with ethyl acetate. The combined organic layers were washed with brine, dried over anhydrous sodium sulfate and concentrated under vacuum. Purification by flash chromatography (petroleum ether/ethyl acetate) provided the titled compound (400 mg, 77%). MS (ESI+) m/z 209.0 [M+H]+.

a9.3) 5-[1-(5-chloropyridin-2-yl)ethyl]-1H-pyrazol-3-amine

Hydrazine hydrate (3.60 g, 71.9 mmol) was added to a solution of 4-(5-chloropyridin-2-yl)-3-oxopentanenitrile (5 g, 23.96 mmol, a9.2) in ethanol (20 mL). The resulting solution was stirred at 80° C. for 4 hours. After cooled to room temperature, the resulting mixture was concentrated under vacuum. This provided the titled compound (3 g, 56.2%). MS (ESI+) m/z 223.0 [M+H]+.

a9.4) 2-[1-(5-chloropyridin-2-yl)ethyl]-5-methylpyrazolo[1,5-a]pyrimidin-7-ol

5-[1-(5-Chloropyridin-2-yl)ethyl]-1H-pyrazol-3-amine (4 g, 17.96 mmol, a9.3) in acetic acid (20 mL) was treated with ethyl 3-oxobutanoate (7.01 g, 53.9 mmol). The resulting solution was stirred at 100° C. for 4 hours. The resulting mixture was concentrated under vacuum, and the residue was washed with ethyl acetate to provide the titled compound (4 g, 77%). MS (ESI+) m/z 289.0 [M+H]+.

a9.5) 7-chloro-2-[1-(5-chloropyridin-2-yl)ethyl]-5-methylpyrazolo[1,5-a]pyrimidine Into a solution of 2-[1-(5-chloropyridin-2-yl)ethyl]-5-methylpyrazolo[1,5-a]pyrimidin-7-ol (2 g, 6.93 mmol, a9.4) in phosphoryl trichloride (3.19 g, 20.78 mmol), triethylamine (2.103 g, 20.78 mmol) was added. The resulting solution was stirred at 100° C. for 2 hours. The reaction mixture was concentrated under vacuum. The crude product was washed with ethyl acetate. The solid was collected and dried in vacuo to provide the titled compound (200 mg, 9.4%). MS (ESI+) m/z 309.0 [M+H]+.

Intermediate a10): (3R)-1-[2-(4-chlorobenzyl)-5-methylpyrazolo[1,5-a]pyrimidin-7-yl]pyrrolidin-3-amine a10.1) tert-butyl {(3R)-1-[2-(4-chlorobenzyl)-5-methylpyrazolo[1,5-a]pyrimidin-7-yl]pyrrolidin-3-yl}carbamate 7-Chloro-2-(4-chlorobenzyl)-5-methylpyrazolo[1,5-a]pyrimidine (500 mg, 1.711 mmol. INTERMEDIATE a1) was added to a suspension of tert-butyl (3R)-pyrrolidin-3-ylcarbamate (319 mg, 1.711 mmol) and potassium carbonate (237 mg, 1.711 mmol) in N,N-dimethylformamide (10 mL). The mixture was stirred at 65° C. for 3 hours. Water and ethyl acetate were added, the organic layer was separated, and the aqueous layer was extracted with ethyl acetate. The combined organic layers were washed with water and dried over sodium sulfate. Purification by flash chromatography (petroleum ether/ethyl acetate) provided the titled compound (450 mg, 59.4%). MS (ESI+) m/z 442.1 [M+H]+; 1H NMR (400 MHz, CD3OD) δ ppm 1.44 (s, 9H), 1.99 (m, 1H), 2.21 (m, 1H), 2.34 (s, 3H), 3.94 (m, 3H), 4.02 (s, 2H), 4.22 (m, 2H), 5.74 (s, 1H), 5.94 (s, 1H), 7.26 (m, 4H).

a10.2) (3R)-1-[2-(4-chlorobenzyl)-5-methylpyrazolo[1,5-a]pyrimidin-7-yl]pyrrolidin-3-amine tert-Butyl {(3R)-1-[2-(4-chlorobenzyl)-5-methylpyrazolo[1,5-a]pyrimidin-7-yl]pyrrolidin-3-yl}carbamate (80 mg, 0.181 mmol, a10.1) in dichloromethane (5 mL) was treated with 2,2,2-trifluoroacetic acid (2 mL). The reaction mixture was stirred at room temperature for 3 hours and then concentrated under vacuum. The crude product was purified by flash chromatography, C18 column (acetonitrile/water, 3:1 v/v) to provide the titled compound (20.8 mg, 33.6%). MS (ESI+) m/z 342.0 [M+H]+; 1H NMR (400 MHz, CD3OD) δ ppm 1.91 (m, 1H), 2.23 (m, 1H), 2.38 (s, 3H), 3.68 (m, 1H), 3.91 (m, 2H), 4.08 (m, 3H), 4.21 (m, 1H), 5.76 (s, 1H), 5.98 (s, 1H), 7.29 (m, 4H).

Intermediate a11): (3S)-1-[2-(4-chlorobenzyl)-5-methylpyrazolo[1,5-a]pyrimidin-7-yl]piperidin-3-amine a11.1) tert-butyl {(3S)-1-[2-(4-chlorobenzyl)-5-methylpyrazolo[1,5-a]pyrimidin-7-yl]piperidin-3-yl}carbamate 7-Chloro-2-(4-chlorobenzyl)-5-methylpyrazolo[1,5-a]pyrimidine (500 mg, 1.711 mmol, INTERMEDIATE a1) was added to a suspension of tert-butyl (3S)-piperidin-3-ylcarbamate (377 mg, 1.883 mmol) and potassium carbonate (237 mg, 1.711 mmol) in N,N-dimethylformamide (6 mL). The mixture was stirred at 50° C. overnight. Water and ethyl acetate were added, the organic layer was separated, and the aqueous layer was extracted with ethyl acetate. The combined organic layers were washed with water and dried over sodium sulfate. Purification by flash chromatography (petroleum ether/ethyl acetate) provided the titled compound (430 mg, 55.1%). A 30 mg aliquot of the titled compound was further purified by preparative-HPLC, Column: Waters XBridge® C18, 19×150 mm, 5 µm; Mobile Phase A: water/ 10 mM NH4HCO3, Mobile Phase B: acetonitrile; Flow rate: 20 mL/minute; Gradient: 30% B to 70% B in 10 minutes; 254 nm. MS (ESI+) m/z 456.1 [M+H]+; 1H NMR (400 MHz, DMSO-d6) δ ppm 1.38 (s, 9H), 1.61 (m, 2H), 1.84 (m, 2H), 2.38 (s, 3H), 3.03 (t, 2H), 3.55 (m, 1H), 4.05 (s, 2H), 4.18 (m, 2H), 6.13 (s, 1H), 6.24 (s, 1H), 7.01 (brs, 1H), 7.33 (m, 4H).

a11.2) (3S)-1-[2-(4-chlorobenzyl)-5-methylpyrazolo[1,5-a]pyrimidin-7-yl]piperidin-3-amine tert-Butyl {(3S)-1-[2-(4-chlorobenzyl)-5-methylpyrazolo[1,5-a]pyrimidin-7-yl]piperidin-3-yl}carbamate (400 mg, 0.877 mmol, a11.1) in N,N-dimethylformamide (5 mL) was treated with 2,2,2-trifluoroacetic acid (100 mg, 0.877 mmol). The mixture was stirred at room temperature overnight and then concentrated under vacuum. The crude material (280 mg, 90%) was used for next step directly without further purification. A 30 mg aliquot of the crude material was purified by preparative-HPLC, Column: Waters XBridge® C18, 19×150 mm, 5 m; Mobile Phase A: water/10 mM NH4HCO3, Mobile Phase B: acetonitrile; Flow rate: 20 mL/minute; Gradient: 30% B to 70% B in 10 minutes; 254 nm, afforded the titled compound (13.6 mg). MS (ESI+) m/z 356.1 [M+H]+; 1H NMR (400 MHz, CD3OD) δ ppm 1.50 (m, 1H), 1.75 (m, 1H), 1.90 (m, 1H), 2.02 (m, 1H), 2.44 (s, 3H), 3.19 (m, 3H), 4.07 (m, 4H), 6.11 (s, 1H), 6.20 (s, 1H), 7.28 (m, 4H).

Intermediate a12): 7-chloro-2-(3-chlorobenzyl)-5-methylpyrazolo[1,5-a]pyrimidine a12.1) 4-(3-chlorophenyl)-3-oxobutanenitrile A solution of butyllithium (1.6 M in hexane, 8.12 mL, 0.833 g, 13.0 mmol) in tetrahydrofuran (30 mL) was cooled to −75° C., and a solution of acetonitrile (0.747 mL, 0.587 g, 14.3 mmol) in tetrahydrofuran (3 mL) was added dropwise. After addition, the solution was stirred for another 90 minutes at −75° C. To the obtained white suspension, a solution of methyl 2-(3-chlorophenyl)acetate (2.40 g, 13.0 mmol) in tetrahydrofuran (10 mL) was added at −75° C., and the reaction mixture was stirred overnight and allowed to warm to room temperature. The mixture was then partitioned between 80% aqueous $NH_4Cl$ solution and ethyl acetate. The organic phases were washed with water and brine, dried over $MgSO_4$, filtered, and concentrated. The residue was chromatographically purified using a Teledyne Isco CombiFlash® system (normal phase: 24 g column, eluent: 25% ethyl acetate/cyclohexane) to give the titled compound (1.47 g, 58%). LC-MS (ESI+) m/z 194.0 [M+H]+.

a12.2) 3-(3-chlorobenzyl)-1H-pyrazol-5-amine

A mixture of 4-(3-chlorophenyl)-3-oxobutanenitrile (1.47 g, 7.59 mmol) and hydrazine monohydrate (0.745 mL, 0.760 g, 15.18 mmol) in ethanol (20 mL) was refluxed for 3 h. For work-up, the reaction mixture was partitioned between water and ethyl acetate. The combined organic layers were washed with 50% aqueous $NaHCO_3$ solution and brine, dried over $MgSO_4$, and concentrated in vacuo. The residue was stirred in a mixture of ethyl acetate/diisopropyl ether (1:1), and the solid was collected by vacuum filtration and dried in a vacuum oven overnight to give the titled compound (772 mg, 49.0%). LC-MS (ESI+) m/z 208.1 [M+H]+.

a12.3) 2-(3-chlorobenzyl)-5-methylpyrazolo[1,5-a]pyrimidin-7-ol

A mixture of compound a12.2 (772 mg, 3.72 mmol) and ethyl 3-oxobutanoate (0.705 mL, 726 mg, 5.58 mmol) in acetic acid (10 mL) was refluxed for 3 h. Then, the reaction mixture was diluted with water (40 mL), and the resultant precipitate was collected by vacuum filtration. The collected solid was washed with diisopropyl ether and dried overnight in a vacuum oven to give the titled compound (1.00 g, 98%). LC-MS (ESI+) m/z 274.0 [M+H]+.

a12.4) 7-chloro-2-(3-chlorobenzyl)-5-methylpyrazolo[1,5-a]pyrimidine

A mixture of compound a12.3 (1.00 g, 3.65 mmol) and phosphoryl trichloride (1.12 g, 0.681 mL, 7.31 mmol) in acetonitrile (15 mL) was refluxed for 8 h. The reaction mixture was quenched with water. The mixture was then partitioned between ethyl acetate and 50% aqueous sodium bicarbonate. The organic fraction was washed with 50% aqueous sodium bicarbonate, dried over $MgSO_4$, and concentrated. The residue was purified chromatographically using a Teledyne Isco RediSep® silica gel cartridge (12 g) on a Teledyne Isco CombiFlash® system eluted with a gradient of 2-5% methanol/dichloromethane (30 mL/minute) to obtain the titled compound (750 mg, 70.3%). LC-MS (ESI+) m/z 292.0 [M+H]+.

II. EXAMPLE COMPOUNDS

Preparation of Compounds Derived from Intermediate a1

Example 1-1

2-{1-[2-(4-chlorobenzyl)-5-methylpyrazolo[1,5-a]pyrimidin-7-yl]piperidin-2-yl}ethanol A mixture of INTERMEDIATE a1 (50 mg, 0.171 mmol), 2-(piperidin-2-yl)ethanol (33.25 mg, 0.25675 mmol), and N-ethyl-N-isopropylpropan-2-amine (33.2 mg, 0.257 mmol) in ethanol (3 mL) was stirred at room temperature. After 12 h, additional 2-(piperidin-2-yl)ethanol (99.75 mg, 0.77025 mmol) was added and stirring was continued for another 3 d.

For work-up, the reaction mixture was partitioned between $H_2O$ and $CH_2Cl_2$, and the combined organic layers were washed with brine, dried over $MgSO_4$, filtered and concentrated in vacuo. The crude product was chromatographically purified using Teledyne Isco CombiFlash® system (normal phase: 4 g column, eluent: 3-5% $CH_3OH/CH_2Cl_2$). The titled compound was obtained after concentration in vacuo over night as clear oil (29 mg, 44.0%). LC-MS (ESI+) m/z 385.2 [M+H]+; 1H NMR (600 MHz, DMSO-d6) δ ppm 12.75 (s, 1H), 10.97 (s, 1H), 7.75 (d, J=8.67 Hz, 1H), 7.50 (dd, J=2.68, 8.77 Hz, 1H), 7.41-7.34 (m, 3H), 7.30 (dd, J=3.84, 5.15 Hz, 1H), 5.28 (s, 2H), 5.08 (d, J=10.50 Hz, 1H), 4.20-4.14 (m, 1H), 3.96 (t, J=12.41 Hz, 1H), 3.51 (d, J=12.27 Hz, 1H), 3.42 (d, J=12.46 Hz, 1H), 3.33 (s, 1H), 3.25 (s, 2H), 3.19 (s, 1H), 2.84 (t, J=7.45 Hz, 2H), 2.74 (q, J=7.54 Hz, 2H), 1.17 (t, J=7.54 Hz, 3H).

Example 1-2

{1-[2-(4-chlorobenzyl)-5-methylpyrazolo[1,5-a]pyrimidin-7-yl]piperidin-2-yl}methanol A mixture of INTERMEDIATE a1 (50 mg, 0.171 mmol), piperidin-2-ylmethanol (79 mg, 0.685 mmol), and N-ethyl-N-isopropylpropan-2-amine (44.2 mg, 0.342 mmol) in ethanol (3 mL) was stirred at ambient temperature for 3 d.

For work-up, the reaction mixture was extracted using $H_2O/CH_2Cl_2$, and the combined organic layers were washed with brine, dried over $MgSO_4$, filtered and concentrated in vacuo. The crude product was chromatographically purified using Teledyne Isco CombiFlash® system (normal phase: 4 g column, eluent: 5-10% $CH_3OH/CH_2Cl_2$). The titled compound was obtained after concentration in vacuo overnight as clear oil (13 mg, 20.48%). LC-MS (ESI+) m/z 371.2 [M+H]+; 1H NMR (600 MHz, DMSO-d6) δ ppm 7.38-7.29 (m, 4H), 6.16 (s, 1H), 6.07 (s, 1H), 5.09 (tt, J=7.0, 4.1 Hz, 1H), 4.65 (t, J=5.3 Hz, 1H), 4.05 (s, 2H), 3.76-3.67 (m, 2H), 3.55 (ddd, J=11.3, 6.6, 5.0 Hz, 1H), 3.35-3.27 (m, 1H), 2.35 (s, 3H), 1.81-1.69 (m, 3H), 1.68-1.56 (m, 3H).

Example 1-3

2-(4-chlorobenzyl)-5-methyl-N-(1-methylcyclopropyl)pyrazolo[1,5-a]pyrimidin-7-amine A mixture of INTERMEDIATE a1 (50 mg, 0.171 mmol), 1-methylcyclopropanamine (48.7 mg, 0.685 mmol), and N-ethyl-N-isopropylpropan-2-amine (44.2 mg, 0.342 mmol) in ethanol (3 mL) were stirred at ambient temperature for 3 d.

For work-up, the reaction mixture was extracted using $H_2O/CH_2Cl_2$ and the combined organic layers were washed with brine, dried over $MgSO_4$, filtered and concentrated in vacuo. The crude product was purified chromatographically using a Teledyne Isco CombiFlash® system (normal phase: 4 g column, eluent: 3-5% $CH_3OH/CH_2Cl_2$). The titled compound was obtained after concentration in vacuo over night as clear oil (22 mg, 39.3%). LC-MS (ESI+) m/z 327.2 $[M+H]^+$; $^1H$ NMR (600 MHz, DMSO-$d_6$) δ ppm 8.07 (s, 1H), 7.37-7.27 (m, 4H), 6.11 (s, 1H), 6.03 (s, 1H), 4.05 (s, 2H), 2.38 (s, 3H), 1.38 (s, 3H), 0.90-0.84 (m, 2H), 0.79-0.74 (m, 2H).

Example 1-4

2-(4-chlorobenzyl)-7-(3,3-difluoropiperidin-1-yl)-5-methylpyrazolo[1,5-a]pyrimidine A mixture of INTERMEDIATE a1 (50 mg, 0.171 mmol), 3,3-difluoropiperidine hydrochloride (108 mg, 0.685 mmol), and N-ethyl-N-isopropylpropan-2-amine (133 mg, 1.027 mmol) in ethanol (3 mL) was stirred at ambient temperature for 3 d.

For work-up, the reaction mixture was extracted using $H_2O/CH_2Cl_2$, and the combined organic layers were washed with brine, dried over $MgSO_4$, filtered and concentrated in vacuo. The crude product was purified chromatographically using a Teledyne Isco CombiFlash® system (normal phase: 4 g column, eluent: 5-10% $CH_3OH/CH_2Cl_2$). The obtained material was triturated with a small amount of ethyl acetate, and the solid was collected by filtration. The titled compound was obtained as white solid after drying in vacuo overnight (44 mg, 68.2%). LC-MS (ESI+) m/z 377.2 $[M+H]^+$; $^1H$ NMR (500 MHz, DMSO-$d_6$) δ ppm 7.38-7.29 (m, 4H), 6.33 (s, 1H), 6.17 (s, 1H), 4.29 (t, J=11.91 Hz, 2H), 4.08 (s, 2H), 3.69 (t, J=5.32 Hz, 2H), 2.40 (s, 3H), 2.15 (tt, J=6.28, 13.85 Hz, 2H), 1.90 (dq, J=5.43, 6.02, 11.50 Hz, 2H).

Example 1-5

1-[2-(4-chlorobenzyl)-5-methylpyrazolo[1,5-a]pyrimidin-7-yl]-3,3-difluoropiperidin-4-ol The synthesis was done analogously to the synthesis described in EXAMPLE 1-4 to obtain the titled compound as a white solid (15 mg, 22.31%). LC-MS (ESI+) m/z 393.2 $[M+H]^+$; $^1H$ NMR (500 MHz, DMSO-$d_6$) δ ppm 7.38-7.29 (m, 4H), 6.34 (s, 1H), 6.17 (s, 1H), 5.80 (d, J=4.8 Hz, 1H), 4.49 (ddd, J=18.7, 13.8, 5.4 Hz, 1H), 4.09 (s, 3H), 3.96 (t, J=10.3 Hz, 1H), 3.82 (td, J=8.4, 6.8, 4.2 Hz, 1H), 3.59 (ddd, J=12.2, 8.1, 3.2 Hz, 1H), 2.40 (s, 3H), 2.03 (ddt, J=15.2, 7.4, 3.8 Hz, 1H), 1.85 (dtt, J=16.6, 7.5, 3.2 Hz, 1H).

Example 1-6

(3S)-1-[2-(4-chlorobenzyl)-5-methylpyrazolo[1,5-a]pyrimidin-7-yl]piperidin-3-ol 7-Chloro-2-(4-chlorobenzyl)-5-methylpyrazolo[1,5-a]pyrimidine (100 mg, 0.342 mmol) was added to a suspension of sodium carbonate (72.6 mg, 0.685 mmol) and (S)-piperidin-3-ol (45.0 mg, 0.445 mmol) in N,N-dimethylformamide (5 mL). The mixture was stirred at 65° C. for 3 hours. The reaction mixture was partitioned between water and ethyl acetate, the organic layer was separated, and the aqueous layer was extracted with ethyl acetate. The combined organic layers were washed with water, dried over sodium sulfate, and concentrated. The residue was purified by flash chromatography, C18 column (acetonitrile/water 3:1 v/v) to provide the titled compound (48.3 mg, 39.5%). MS(ESI+) m/z 357.1 $[M+H]^+$; $^1H$ NMR (400 MHz, DMSO-$d_6$) δ ppm 1.44 (m, 1H), 1.58 (m, 1H), 1.82 (m, 1H), 1.94 (m, 1H), 2.37 (s, 3H), 3.09 (m, 1H), 3.17 (m, 1H), 3.68 (m, 1H), 4.03 (m, 1H), 4.06 (s, 2H), 4.15 (m, 1H), 6.11 (s, 1H), 6.20 (s, 1H), 7.32 (m, 4H).

Example 1-7

(3R)-1-[2-(4-chlorobenzyl)-5-methylpyrazolo[1,5-a]pyrimidin-7-yl]piperidin-3-ol 7-Chloro-2-(4-chlorobenzyl)-5-methylpyrazolo[1,5-a]pyrimidine (70 mg, 0.240 mmol) was added to a suspension of potassium carbonate (33.1 mg, 0.240 mmol) and (R)-piperidin-3-ol (26.7 mg, 0.264 mmol) in N,N-dimethylformamide (6 mL). The mixture was stirred at 50° C. overnight. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: XBridge® C18, 19×150 mm, 5 μm; mobile phase A: water/10 mM $NH_4HCO_3$, mobile phase B: acetonitrile; flow rate: 20 mL/minute; gradient: 30% B to 70% B in 10 minutes; 254 nm) provided the titled compound (28.5 mg, 33.3%). MS(ESI+) m/z 357.1 $[M+H]^+$; $^1H$ NMR (400 MHz, CD$_3$OD) δ ppm 1.71 (m, 2H), 2.05 (m, 2H), 2.47 (s, 3H), 3.34 (m, 2H), 3.95 (m, 2H), 4.13 (s, 2H), 4.23 (m, 1H), 6.13 (s, 1H), 6.22 (s, 1H), 7.32 (m, 4H).

Example 1-8

{(3S)-1-[2-(4-chlorobenzyl)-5-methylpyrazolo[1,5-a]pyrimidin-7-yl]piperidin-3-yl}methanol 7-Chloro-2-(4-chlorobenzyl)-5-methylpyrazolo[1,5-a]pyrimidine (70 mg, 0.240 mmol) was added to a suspension of potassium carbonate (33.1 mg, 0.240 mmol) and (S)-piperidin-3-ylmethanol (30.4 mg, 0.264 mmol) in N,N-dimethylformamide (6 mL). The mixture was stirred at 50° C. overnight. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters XBridge® C18, 19×150 mm, 5 μm; mobile phase A: water/0.05% trifluoroacetic acid, mobile phase B: acetonitrile; flow rate: 20 mL/minute; gradient: 30% B to 70% B in 10 minutes; 254 nm) provided the titled compound as a trifluoroacetic acid salt (21.6 mg, 18.6%). MS(ESI+) m/z 371.1 [M+H]+; $^1$H NMR (400 MHz, DMSO-$d_6$) δ ppm 1.25 (m, 1H), 1.72 (m, 4H), 2.38 (s, 3H), 2.97 (m, 2H), 3.37 (m, 2H), 4.05 (s, 2H), 4.22 (m, 1H), 4.29 (m, 1H), 4.64 (t, 1H), 6.12 (s, 1H), 6.19 (s, 1H), 7.33 (m, 4H).

Example 1-9

2-(4-chlorobenzyl)-5-methyl-7-(piperidin-1-yl)pyrazolo[1,5-a]pyrimidine

Into a mixture of piperidine (17.49 mg, 0.205 mmol) and potassium carbonate (71 mg, 0.513 mmol) in 1,4-dioxane (5 mL) was added 7-chloro-2-(4-chlorobenzyl)-5-methylpyrazolo[1,5-a]pyrimidine (50 mg, 0.171 mmol). The resulting mixture was stirred overnight at 95° C. After concentration under vacuum, the residue was purified by preparative-HPLC, Column: Waters XBridge® C18, 19×150 mm, 5 µm; Mobile Phase A: water/0.05% trifluoroacetic acid, Mobile Phase B: acetonitrile; Flow rate: 20 mL/minute; Gradient: 30% B to 70% B in 10 minutes; 254 nm, to provide the titled compound as a trifluoroacetic acid salt (33.7 mg, 43.3%). MS (ESI+) m/z 341.1 [M+H]+; NMR (400 MHz, CD$_3$OD) δ ppm 1.82 (m, 6H), 2.51 (s, 3H), 4.11 (s, 2H), 4.23 (m, 4H), 6.21 (s, 1H), 6.42 (s, 1H), 7.29 (m, 4H).

Example 1-10

1-[2-(4-chlorobenzyl)-5-methylpyrazolo[1,5-a]pyrimidin-7-yl]piperidin-2-one

7-Chloro-2-(4-chlorobenzyl)-5-methylpyrazolo[1,5-a]pyrimidine (100 mg, 0.342 mmol) was added to a suspension of piperidin-2-one (67.9 mg, 0.685 mmol), tris(dibenzylideneacetone)dipalladium(0) (Pd$_2$(dba)$_3$, 31 mg, 0.034 mmol), 2-dicyclohexylphosphino-2',4',6'-triisopropylbiphenyl (XPhos, 16 mg, 0.034 mmol) and cesium carbonate (335 mg, 1.027 mmol) in 1,4-dioxane (3 mL). The vessel was flushed with argon, and then the mixture was stirred and heated in the microwave (100° C., 300 W, 1 hour). The final mixture was concentrated under vacuum. Purification of the residue by flash chromatography on silica eluted with ethyl acetate/petroleum ether (gradient ethyl acetate:petroleum ether from 0:1 to 1:1) provided the titled compound (42.1 mg, 34.7%). MS(ESI+) m/z 355.1 [M+H]+; $^1$H NMR (400 MHz, CD$_3$OD) δ ppm 2.07 (m, 4H), 2.60 (s, 3H), 2.65 (t, 2H), 3.82 (t, 2H), 4.16 (s, 2H), 6.38 (s, 1H), 6.93 (s, 1H), 7.31 (m, 4H).

Example 1-11

N-{(3R)-1-[2-(4-chlorobenzyl)-5-methylpyrazolo[1,5-a]pyrimidin-7-yl]pyrrolidin-3-yl}acetamide Into a mixture of N-[(3R)-pyrrolidin-3-yl]acetamide (32.9 mg, 0.257 mmol) and potassium carbonate (71 mg, 0.513 mmol) in 1,4-dioxane (5 mL) was added 7-chloro-2-(4-chlorobenzyl)-5-methylpyrazolo[1,5-a]pyrimidine (50 mg, 0.171 mmol). The resulting mixture was stirred overnight at 95° C. Water and ethyl acetate were added, the organic layer was separated and the aqueous layer was extracted with ethyl acetate. The combined organic layers were washed with water and dried over sodium sulfate. After filtration and concentration under reduced pressure, the crude residue was purified by preparative-HPLC, Column: Waters XBridge® C18, 19×150 mm, 5 µm; Mobile Phase A: water/0.1% trifluoroacetic acid, Mobile Phase B: acetonitrile; Flow rate: 20 mL/minute; Gradient: 30% B to 70% B in 10 minutes; 254 nm, to provide the titled compound (45 mg, 68.5%). MS (ESI+) m/z 384.1 [M+H]+; NMR (400 MHz, DMSO-$d_6$) δ ppm 1.81 (s, 3H), 1.90 (m, 1H), 2.11 (m, 1H), 2.29 (s, 3H), 3.85 (m, 3H), 4.00 (s, 2H), 4.10 (m, 1H), 4.32 (m, 1H), 5.80 (s, 1H), 5.98 (s, 1H), 7.33 (m, 4H), 8.17 (d, 1H).

Example 1-12

2-(4-chlorobenzyl)-5-methyl-7-(pyrrolidin-1-yl)pyrazolo[1,5-a]pyrimidine

Into a mixture of pyrrolidine (18.26 mg, 0.257 mmol) and potassium carbonate (71 mg, 0.513 mmol) in 1,4-dioxane (5 mL) was added 7-chloro-2-(4-chlorobenzyl)-5-methylpyrazolo[1,5-a]pyrimidine (50 mg, 0.171 mmol). The resulting mixture was stirred overnight at 95° C. Water and ethyl acetate were added, the organic layer was separated, and the aqueous layer was extracted with ethyl acetate. The combined organic layers were washed with water and dried over sodium sulfate. After filtration and concentration under reduced pressure, the crude product was purified by preparative-HPLC, Column: Waters XBridge® C18, 19×150 mm, 5 µm; Mobile Phase A: water/0.1% trifluoroacetic acid, Mobile Phase B: acetonitrile; Flow rate: 20 mL/minute; Gradient: 30% B to 70% B in 10 minutes; 254 nm, to give the titled compound (41.3 mg, 73.8%). MS (ESI+) m/z 327.3 [M+H]+; NMR (400 MHz, CD$_3$OD) δ ppm 2.10 (m, 4H), 2.50 (s, 3H), 3.82 (m, 2H), 4.11 (s, 2H), 4.64 (m, 2H), 6.14 (s, 1H), 6.15 (s, 1H), 7.32 (m, 4H).

Example 1-13

7-(azetidin-1-yl)-2-(4-chlorobenzyl)-5-methylpyrazolo[1,5-a]pyrimidine

7-Chloro-2-(4-chlorobenzyl)-5-methylpyrazolo[1,5-a]pyrimidine (50 mg, 0.171 mmol) was added to a solution of azetidine (14.66 mg, 0.257 mmol) and triethylamine (52.0 mg, 0.513 mmol) in acetonitrile (5 mL). The resulting mixture was stirred overnight at 95° C. Water and ethyl acetate were added, the organic layer was separated and the aqueous layer was extracted with ethyl acetate. The combined organic layers were washed with water and dried over sodium sulfate. After filtration and concentration under reduced pressure, the crude product was purified by preparative-HPLC, Column: Waters XBridge® C18, 19×150 mm, 5 µm; Mobile Phase A: water/0.1% trifluoroacetic acid, Mobile Phase B: acetonitrile; Flow rate: 20 mL/minute; Gradient: 30% B to 70% B in 10 minutes; 254 nm, to provide the titled compound (42.5 mg, 79.4%). MS (ESI+) m/z 313.3 [M+H]+; NMR (400 MHz, CD$_3$OD) δ ppm 2.48 (s, 3H), 2.61 (m, 2H), 4.09 (s, 2H), 4.51 (m, 2H), 5.15 (m, 2H), 5.88 (s, 1H), 6.12 (s, 1H), 7.32 (m, 4H).

Example 1-14

N-tert-butyl-2-(4-chlorobenzyl)-5-methylpyrazolo[1,5-a]pyrimidin-7-amine

7-Chloro-2-(4-chlorobenzyl)-5-methylpyrazolo[1,5-a]pyrimidine (50 mg, 0.171 mmol) was added to a solution of 2-methylpropan-2-amine (62.6 mg, 0.856 mmol) and triethylamine (52.0 mg, 0.513 mmol) in acetonitrile (5 mL). The mixture was stirred at 95° C. overnight and then concentrated under vacuum. The residue was purified by preparative-HPLC (column: Waters XBridge® C18, 19×150 mm, 5 µm; mobile phase A: water/0.05% trifluoroacetic acid, mobile phase B: acetonitrile; flow rate: 20 mL/minute; gradient: 30% B to 70% B in 10 minutes; 254 nm) to provide the titled compound (5.1 mg, 9.1%). MS(ESI+) m/z 329.2 [M+H]$^+$; $^1$H NMR (400 MHz, DMSO-d$_6$) δ ppm 1.57 (s, 9H), 2.41 (s, 3H), 4.10 (s, 2H), 4.60 (brs, 1H), 6.06 (s, 1H), 6.20 (s, 1H), 7.31 (m, 4H).

Example 1-15

2-(4-chlorobenzyl)-5-methyl-N-[1-(trifluoromethyl)cyclopropyl]pyrazolo[1,5-a]pyrimidin-7-amine 7-Chloro-2-(4-chlorobenzyl)-5-methylpyrazolo[1,5-a]pyrimidine (100 mg, 0.342 mmol) was added to a suspension of 1-(trifluoromethyl)cyclopropanamine hydrochloride (276 mg, 1.711 mmol), cesium carbonate (335 mg, 1.027 mmol) and potassium iodide (56.8 mg, 0.342 mmol) in 1,4-dioxane (5 mL). The resulting mixture was stirred at 135° C. overnight. This reaction mixture was concentrated under vacuum, and the residue was purified by preparative-HPLC (column: Waters XBridge® C18, 19×150 mm, 5 m; mobile phase A: water/0.5% NH$_4$HCO$_3$, mobile phase B: acetonitrile; flow rate: 20 mL/minute; gradient: 30% B to 70% B in 10 minutes; 254 nm) to provide the titled compound (38.3 mg, 29.4%). MS(ESI+) m/z 381.2 [M+H]$^+$; $^1$H NMR (400 MHz, CD$_3$OD) δ ppm 1.36 (m, 2H), 1.56 (m, 2H), 2.48 (s, 3H), 4.13 (s, 2H), 6.10 (s, 1H), 6.27 (s, 1H), 7.30 (m, 4H).

Example 1-16

2-(4-chlorobenzyl)-5-methyl-N-(2,2,2-trifluoroethyl)pyrazolo[1,5-a]pyrimidin-7-amine 7-Chloro-2-(4-chlorobenzyl)-5-methylpyrazolo[1,5-a]pyrimidine (20 mg, 0.068 mmol) was added to a solution of 2,2,2-trifluoroethanamine (67.8 mg, 0.685 mmol) and triethylamine (20.8 mg, 0.205 mmol) in acetonitrile (5 mL). The resulting mixture was stirred at 90° C. overnight. This reaction mixture was concentrated under vacuum, and the crude residue was purified by preparative-HPLC (column: Waters XBridge® C18, 19×150 mm, 5 µm; mobile phase A: water/0.05% trifluoroacetic acid, mobile phase B: acetonitrile; flow rate: 20 mL/minute; gradient: 30% B to 70% B in 10 minutes; 254 nm) to provide the titled compound as a trifluoroacetic acid salt (14.1 mg, 43.9%). MS(ESI+) m/z 355.3 [M+H]$^+$; $^1$H NMR (400 MHz, CD$_3$OD) δ ppm 2.63 (s, 3H), 4.21 (s, 2H), 4.43 (q, 2H), 6.32 (s, 1H), 6.65 (s, 1H), 7.33 (m, 4H).

Example 1-17

N-{(3S)-1-[2-(4-chlorobenzyl)-5-methylpyrazolo[1,5-a]pyrimidin-7-yl]pyrrolidin-3-yl}acetamide Into a mixture of N-[(3S)-pyrrolidin-3-yl]acetamide (32.9 mg, 0.257 mmol) and potassium carbonate (71 mg, 0.513 mmol) in 1,4-dioxane (5 mL) was added 7-chloro-2-(4-chlorobenzyl)-5-methylpyrazolo[1,5-a]pyrimidine (50 mg, 0.171 mmol). The resulting mixture was stirred overnight at 95° C. Water and ethyl acetate were added, the organic layer was separated, and the aqueous layer was extracted with ethyl acetate. The combined organic layers were washed with water and dried over sodium sulfate. After filtration and concentration under reduced pressure, the crude product was purified by preparative-HPLC, Column: Waters XBridge® C18, 19×150 mm, 5 µm; Mobile Phase A: water/0.1% trifluoroacetic acid, Mobile Phase B: acetonitrile; Flow rate: 20 mL/minute; Gradient: 30% B to 70% B in 10 minutes; 254 nm, to provide the titled compound (56.7 mg, 86.4%). MS (ESI+) m/z 384.1 [M+H]$^+$; NMR (400 MHz, DMSO-d$_6$) δ ppm 1.81 (s, 3H), 1.90 (m, 1H), 2.11 (m, 1H), 2.29 (s, 3H), 3.85 (m, 3H), 4.00 (s, 2H), 4.10 (m, 1H), 4.32 (m, 1H), 5.80 (s, 1H), 5.98 (s, 1H), 7.33 (m, 4H), 8.17 (d, 1H).

Example 1-18

2-(4-chlorobenzyl)-5-methyl-N-[(2S)-1,1,1-trifluoropropan-2-yl]pyrazolo[1,5-a]pyrimidin-7-amine 7-Chloro-2-(4-chlorobenzyl)-5-methylpyrazolo[1,5-a]pyrimidine (100 mg, 0.342 mmol) was added to a suspension of (S)-1,1,1-trifluoropropan-2-amine hydrochloride (256 mg, 1.711 mmol), potassium iodide (85 mg, 0.513 mmol) and cesium carbonate (335 mg, 1.027 mmol) in 1,4-dioxane (5 mL). The resulting solution was stirred at 130° C. for 48 hours. This reaction mixture was concentrated under vacuum, and the residue was purified by preparative-HPLC (column: Waters XBridge® C18, 19×150 mm, 5 µm; mobile phase A: water/0.1% NH$_4$HCO$_3$, mobile phase B: acetonitrile; flow rate: 20 mL/minute; gradient: 30% B to 70% B in 10 minutes; 254 nm) to provide the titled compound (50.4 mg, 39.9%). MS(ESI+) m/z 369.3 [M+H]$^+$; $^1$H NMR (400 MHz, CD$_3$OD) δ ppm 1.58 (d, 3H), 2.47 (s, 3H), 4.13 (s, 2H), 4.68 (m, 1H), 6.11 (s, 1H), 6.26 (s, 1H), 7.31 (m, 4H).

Example 1-19

1-[2-(4-chlorobenzyl)-5-methylpyrazolo[1,5-a]pyrimidin-7-yl]piperidine-3-carboxamide 7-Chloro-2-(4-chlorobenzyl)-5-methylpyrazolo[1,5-a]pyrimidine (100 mg, 0.342 mmol) was added to a suspension of piperidine-3-carboxamide (65.8 mg, 0.513 mmol) and potassium carbonate (95 mg, 0.685 mmol) in N,N-dimethylformamide (3 mL). The mixture was stirred at 50° C. for 5 hours and then concentrated under vacuum. Purification of the residue by flash chromatography on silica gel eluted with methanol/dichloromethane (gradient methanol:dichloromethane from 0:1 to 1:3) provided a solid. Then washing the solid with ether provided the titled compound (114.9 mg, 87%). MS(ESI+) m/z 384.1 [M+H]$^+$; $^1$H NMR (400 MHz, CD$_3$OD) δ ppm 1.83 (m, 1H), 1.96 (m, 2H), 2.14 (m, 1H), 2.55 (s, 3H), 2.77 (m, 1H), 3.32 (m, 2H), 3.70 (m, 1H), 4.02 (m, 1H), 4.14 (s, 2H), 6.26 (s, 1H), 6.51 (s, 1H), 7.31 (m, 4H).

Example 1-20

2-(4-chlorobenzyl)-5-methyl-N-[(2R)-1,1,1-trifluoropropan-2-yl]pyrazolo[1,5-a]pyrimidin-7-amine 7-Chloro-2-(4-chlorobenzyl)-5-methylpyrazolo[1,5-a]pyrimidine (100 mg, 0.342 mmol) was added to a suspension of (R)-1,1,1-trifluoropropan-2-amine hydrochloride (256 mg, 1.711 mmol), potassium iodide (114 mg, 0.685 mmol) and cesium carbonate (335 mg, 1.027 mmol) in 1,4-dioxane (5 mL). The resulting solution was stirred at 130° C. for 48 hours. This reaction mixture was concentrated under vacuum, and the residue was purified by preparative-HPLC (column: Waters XBridge® C18, 19×150 mm, 5 µm; mobile phase A: water/0.1% NH$_4$HCO$_3$, mobile phase B: acetonitrile; flow rate: 20 mL/minute; gradient: 30% B to 70% B in 10 minutes; 254 nm) to provide the titled compound (35.9 mg, 28.4%). MS(ESI+) m/z 369.3 [M+H]+; 1H NMR (400 MHz, CD3OD) δ ppm 1.57 (d, 3H), 2.46 (s, 3H), 4.11 (s, 2H), 4.67 (m, 1H), 6.11 (s, 1H), 6.25 (s, 1H), 7.28 (m, 4H).

Example 1-21

{(3R)-1-[2-(4-chlorobenzyl)-5-methylpyrazolo[1,5-a]pyrimidin-7-yl]piperidin-3-yl}methanol 7-Chloro-2-(4-chlorobenzyl)-5-methylpyrazolo[1,5-a]pyrimidine (100 mg, 0.342 mmol) was added to a suspension of (R)-piperidin-3-ylmethanol (59.1 mg, 0.513 mmol) and potassium carbonate (95 mg, 0.685 mmol) in N,N-dimethylformamide (3 mL). The mixture was stirred at 60° C. for 5 hours and then concentrated under vacuum. Purification of the residue by flash chromatography on silica gel eluted with ethyl acetate/petroleum ether (gradient ethyl acetate:petroleum ether from 0:1 to 1:1) provided the titled compound (44.4 mg, 35%). MS(ESI+) m/z 371.1 [M+H]+; 1H NMR (400 MHz, CD3OD) δ ppm 1.32 (m, 1H), 1.66 (m, 1H), 1.74 (m, 2H), 1.88 (m, 1H), 2.34 (s, 3H), 3.04 (m, 1H), 3.17 (m, 1H), 3.45 (m, 1H), 3.54 (m, 1H), 4.04 (m, 4H), 6.02 (s, 1H), 6.09 (s, 1H), 7.18 (m, 4H).

Preparation of Compounds Derived from Intermediate a2

Example 2-1

2-(1-{2-[1-(4-chlorophenyl)ethyl]-5-methylpyrazolo[1,5-a]pyrimidin-7-yl}piperidin-2-yl)ethanol A mixture of INTERMEDIATE a2 (300 mg, 0.980 mmol), 2-(piperidin-2-yl)ethanol (506 mg, 3.92 mmol), and N-ethyl-N-isopropylpropan-2-amine (253 mg, 1.960 mmol) was dissolved in ethanol (3 mL) and stirred at 50° C. for 12 h.
For work-up, the reaction mixture was extracted with H2O/CH2Cl2, and the organic layers were washed with brine, dried over MgSO4, filtered and concentrated. The residue was purified chromatographically using a Teledyne Isco CombiFlash® system (normal phase: 4 g column, eluent: 3-5% CH3OH/CH2Cl2) to give the titled compound as a clear yellow oil (115 mg, 29.4%).

Example 2-2

2-[1-(4-chlorophenyl)ethyl]-5-methyl-N-(1-methylcyclopropyl)pyrazolo[1,5-a]pyrimidin-7-amine The synthesis was done analogously to the synthesis described in EXAMPLE 2-1 to obtain the titled compound as a clear oil (7.49%). LC-MS (ESI+) m/z 341.2 [M+H]+; 1H NMR (600 MHz, CDCl3) δ ppm 7.29-7.19 (m, 4H), 6.64 (s, 1H), 6.24 (s, 1H), 6.07 (s, 1H), 4.25 (q, J=7.2 Hz, 1H), 2.55 (s, 3H), 1.67 (d, J=7.3 Hz, 3H), 1.49 (s, 3H), 1.02-0.97 (m, 2H), 0.87-0.81 (m, 2H).

Example 2-3

2-[1-(4-chlorophenyl)ethyl]-7-(3,3-difluoropyrrolidin-1-yl)-5-methylpyrazolo[1,5-a]pyrimidine The synthesis was done analogously to the synthesis described in EXAMPLE 2-1 to obtain the titled compound as a clear oil (13.54%). LC-MS (ESI+) m/z 377.2 [M+H]+; 1H NMR (600 MHz, DMSO-d6) δ ppm 7.34 (s, 7H), 6.10 (s, 2H), 5.95 (s, 2H), 5.76 (s, 1H), 4.39 (t, J=13.2 Hz, 5H), 4.27 (q, J=7.2 Hz, 2H), 2.34 (s, 6H), 1.61 (d, J=7.2 Hz, 7H).

Example 2-4

2-[1-(4-chlorophenyl)ethyl]-7-(4-fluoropiperidin-1-yl)-5-methylpyrazolo[1,5-a]pyrimidine A mixture of INTERMEDIATE a2 (70 mg, 0.229 mmol), 4-fluoropiperidine hydrochloride (96 mg, 0.686 mmol), and N-ethyl-N-isopropylpropan-2-amine (117 mg, 1.372 mmol) was dissolved in dioxane (2 mL) and stirred at 50° C. for 6 h and then stirred overnight at room temperature.
For work-up, the reaction mixture was extracted with H2O/ethyl acetate, and the combined organic layers were washed with brine, dried over MgSO4, filtered and concentrated. After chromatographic purification using a Teledyne Isco CombiFlash® system (normal phase: 4 g column, eluent: CH3OH/CH2Cl2), the titled compound was obtained as clear oil (54 mg, 63.3%). 1H NMR (500 MHz, DMSO-d6) δ ppm 7.34 (s, 6H), 6.25 (s, 2H), 6.19 (s, 2H), 4.99 (tt, J=6.8, 3.4 Hz, 1H), 4.31 (q, J=7.2 Hz, 2H), 3.78 (t, J=10.2 Hz, 4H), 3.70 (dq, J=11.2, 5.0 Hz, 4H), 3.29 (s, 3H), 2.39 (s, 6H), 2.05 (dddd, J=26.0, 12.4, 8.4, 3.9 Hz, 4H), 1.86 (dtd, J=13.6, 10.5, 6.4 Hz, 4H), 1.62 (d, J=7.1 Hz, 6H).

Example 2-5

(1-{2-[1-(4-chlorophenyl)ethyl]-5-methylpyrazolo[1,5-a]pyrimidin-7-yl}piperidin-2-yl)methanol A mixture of INTERMEDIATE a2 (70 mg, 0.229 mmol), piperidin-2-ylmethanol (79 mg, 0.686 mmol), and N-ethyl-N-isopropylpropan-2-amine (89 mg, 0.686 mmol) was dissolved in dioxane (3 mL) and stirred at 50° C. for 6 h and stirred over night at room temperature. The reaction was then placed in a CEM-MW microwave reactor at 140° C. for 90 minutes.
For work-up, the reaction mixture was extracted with H2O/ethyl acetate and the organic layers were washed with brine, dried over MgSO4, filtered and concentrated. After chromatographic purification using a Teledyne Isco CombiFlash® system (normal phase: 4 g column, eluent: CH3OH/CH2Cl2), the titled compound was obtained as a clear oil (64 mg, 72.2%). LC-MS (ESI+) m/z 385.2 [M+H]+; 1H NMR (500 MHz, DMSO-d6) δ ppm 7.39-7.30 (m, 4H), 6.17-6.07 (m, 2H), 5.03 (s, 1H), 4.65 (td, J=5.1, 3.6 Hz, 2H), 4.32-4.24 (m, 2H), 3.81-3.68 (m, 4H), 3.57 (dt, J=11.3, 5.8 Hz, 2H), 3.34-3.25 (m, 2H), 2.35 (d, J=1.0 Hz, 3H), 1.74 (d, J=18.8 Hz, 3H).

Example 2-6

2-[1-(4-chlorophenyl)ethyl]-7-(3-fluoropiperidin-1-yl)-5-methylpyrazolo[1,5-a]pyrimidine The synthesis was done analogously to the synthesis described in EXAMPLE 2-4 to obtain the titled compound as a clear oil (66.9%). LC-MS (ESI+) m/z 373.2 [M+H]+; 1H NMR (600 MHz, DMSO-d6) δ ppm 7.34 (d, J=2.1 Hz, 8H), 6.25 (s, 2H), 6.18 (d, J=8.5 Hz, 2H), 4.90 (dh, J=6.0, 2.9 Hz, 1H), 4.82 (tq, J=5.7, 2.8 Hz, 1H), 4.34-4.19 (m, 2H), 3.87-3.77 (m, 4H), 3.47 (ddt, J=12.1, 9.1, 4.5 Hz, 2H), 3.32 (s, 1H), 2.38 (s, 3H), 2.03-1.85 (m, 3H), 1.67-1.60 (m, 4H).

Example 2-7

2-[1-(4-chlorophenyl)ethyl]-7-(3,3-difluoropiperidin-1-yl)-5-methylpyrazolo[1,5-a]pyrimidine The synthesis was done analogously to the synthesis described in EXAMPLE 2-4 to obtain the titled compound as a clear oil (66.0%). LC-MS (ESI+) m/z 391.2; $^1$H NMR (500 MHz, DMSO-$d_6$) δ ppm 7.34 (s, 4H), 6.32 (s, 1H), 6.21 (s, 1H), 4.39-4.20 (m, 2H), 3.68 (t, J=5.6 Hz, 2H), 2.40 (s, 3H), 2.14 (tt, J=13.9, 6.3 Hz, 2H), 1.90 (d, J=5.9 Hz, 2H), 1.63 (d, J=7.3 Hz, 4H).

Example 2-8

N-tert-butyl-2-[1-(4-chlorophenyl)ethyl]-5-methylpyrazolo[1,5-a]pyrimidin-7-amine A mixture of INTERMEDIATE a2 (80 mg, 0.261 mmol), 2-methylpropan-2-amine (57.3 mg, 0.784 mmol), and N-ethyl-N-isopropylpropan-2-amine (101 mg, 0.784 mmol) was dissolved in dioxane (2 mL) and irradiated in a CEM microwave reactor at 160° C. for 120 minutes.

For work-up, the reaction mixture was extracted with ethyl acetate and the organic layers were washed with brine, dried over MgSO$_4$, filtered, and concentrated. Chromatographic purification with Teledyne Isco CombiFlash® system (normal phase: 4 g column, eluent: 3-5% CH$_3$OH/ CH$_2$Cl$_2$) gave the titled compound as an orange oil (15 mg, 16.74%). LC-MS (ESI+) m/z 343.2 [M+H]$^+$; $^1$H NMR (600 MHz, DMSO-$d_6$) δ ppm 7.34 (s, 3H), 6.42 (s, 1H), 6.20 (s, 1H), 6.15 (s, 1H), 4.29 (q, J=7.2 Hz, 1H), 2.38 (s, 3H), 1.60 (d, J=7.2 Hz, 3H), 1.48 (s, 9H).

Example 2-9

2-[1-(4-chlorophenyl)ethyl]-5-methyl-7-(2-oxa-7-azaspiro[3.5]non-7-yl)pyrazolo[1,5-a]pyrimidine The synthesis was done analogously to the synthesis described in EXAMPLE 2-4 to obtain the titled compound as a clear oil (24.24%). LC-MS (ESI+) m/z 397.2 [M+H]$^+$; $^1$H NMR (600 MHz, DMSO-$d_6$) δ ppm 7.34 (s, 5H), 6.19 (d, J=13.8 Hz, 3H), 4.37 (s, 7H), 4.30 (q, J=7.2 Hz, 2H), 3.64-3.56 (m, 7H), 2.37 (s, 5H), 1.99 (s, 1H), 1.95 (t, J=5.6 Hz, 7H), 1.62 (d, J=7.2 Hz, 5H), 1.17 (t, J=7.1 Hz, 1H).

Example 2-10

(3S)-1-{2-[1-(4-chlorophenyl)ethyl]-5-methylpyrazolo[1,5-a]pyrimidin-7-yl}piperidin-3-ol The synthesis was done analogously to the synthesis described in EXAMPLE 2-4 to obtain the titled compound as a clear oil (61.3%). LC-MS (ESI+) m/z 371.2 [M+H]$^+$; $^1$H NMR (600 MHz, DMSO-$d_6$) δ ppm 7.35 (d, J=2.1 Hz, 3H), 6.21-6.14 (m, 2H), 4.93 (d, J=4.3 Hz, 1H), 4.29 (q, J=7.2 Hz, 1H), 4.15 (dt, J=12.7, 3.4 Hz, 1H), 4.09-3.99 (m, 1H), 3.69 (dd, J=8.5, 4.2 Hz, 1H), 3.20-3.04 (m, 2H), 2.37 (s, 3H), 2.01-1.90 (m, 1H), 1.83 (dp, J=12.8, 4.2 Hz, 1H), 1.64-1.52 (m, 4H), 1.49-1.40 (m, 1H).

Example 2-11

(3R)-1-{2-[1-(4-chlorophenyl)ethyl]-5-methylpyrazolo[1,5-a]pyrimidin-7-yl}piperidin-3-ol The synthesis was done analogously to the synthesis described in EXAMPLE 2-4 to obtain the titled compound as a clear oil (68.4%). LC-MS (ESI+) m/z 371.2 [M+H]$^+$; $^1$H NMR (600 MHz, DMSO-$d_6$) δ ppm 7.38-7.31 (m, 4H), 6.21-6.14 (m, 2H), 4.94 (d, J=4.3 Hz, 1H), 4.29 (q, J=7.2 Hz, 1H), 4.15 (dt, J=12.4, 3.3 Hz, 1H), 4.09-3.99 (m, 2H), 3.68 (tp, J=8.3, 4.1 Hz, 1H), 3.35-3.26 (m, 1H), 3.20-3.04 (m, 2H), 2.37 (s, 3H), 1.99 (s, 1H), 1.94 (dq, J=12.6, 4.3 Hz, 1H), 1.83 (dp, J=12.9, 4.4 Hz, 1H), 1.64-1.53 (m, 4H), 1.44 (dddd, J=12.7, 10.6, 8.9, 4.0 Hz, 1H), 1.17 (t, J=7.1 Hz, 1H).

Example 2-12

7-(azetidin-1-yl)-2-[1-(4-chlorophenyl)ethyl]-5-methylpyrazolo[1,5-a]pyrimidine

The synthesis was done analogously to the synthesis described in EXAMPLE 2-5 to obtain the titled compound as a white solid (28.1%). LC-MS (ESI+) m/z 372.2 [M+H]$^+$; $^1$H NMR (600 MHz, DMSO-$d_6$) δ ppm 7.33 (d, J=0.7 Hz, 4H), 5.99 (s, 1H), 5.61 (s, 1H), 4.43-4.37 (m, 4H), 4.22 (q, J=7.2 Hz, 1H), 2.41-2.32 (m, 2H), 2.29 (s, 3H), 1.58 (d, J=7.2 Hz, 3H).

Example 2-13

2-[1-(4-chlorophenyl)ethyl]-5-methyl-7-(7-oxa-2-azaspiro[3.5]non-2-yl)pyrazolo[1,5-a]pyrimidine The synthesis was done analogously to the synthesis described in EXAMPLE 2-5 to obtain the titled compound as a white solid (62.8%). LC-MS (ESI+) m/z 398.1 [M+H]$^+$; $^1$H NMR (600 MHz, DMSO-$d_6$) δ ppm 7.37-7.29 (m, 4H), 6.01 (s, 1H), 5.65 (s, 1H), 4.23 (q, J=7.2 Hz, 1H), 4.17 (s, 5H), 3.55 (q, J=6.4, 5.5 Hz, 4H), 3.33 (d, J=8.7 Hz, 2H), 2.29 (s, 3H), 1.78 (t, J=5.3 Hz, 4H), 1.59 (d, J=7.2 Hz, 3H).

Example 2-14

2-[1-(4-chlorophenyl)ethyl]-N-(3-fluorocyclobutyl)-5-methylpyrazolo[1,5-a]pyrimidin-7-amine The synthesis was done analogously to the synthesis described in EXAMPLE 2-5 to obtain the titled compound as a clear oil (68.30%). LC-MS (ESI+) m/z 360.1

Example 2-15

(2R,3R)-1-{2-[1-(4-chlorophenyl)ethyl]-5-methylpyrazolo[1,5-a]pyrimidin-7-yl}-3-ethylazetidine-2-carboxylic acid The synthesis was done analogously to the synthesis described in EXAMPLE 2-4 to obtain the titled compound as a clear foam (17.55%). LC-MS (ESI+) m/z 399.1 [M+H]$^+$; $^1$H NMR (600 MHz, DMSO-$d_6$) δ ppm 12.81 (s, 1H), 7.35-7.26 (m, 4H), 5.93 (d, J=10.1 Hz, 1H), 5.74 (d, J=28.4 Hz, 1H), 5.52 (s, 1H), 4.33 (s, 1H), 4.18 (q, J=7.2 Hz, 1H), 4.13 (s, 1H), 3.78 (s, 1H), 3.40-3.35 (m, 1H), 3.32 (d, J=6.1 Hz, 1H), 3.11 (s, 1H), 2.31 (d, J=1.8 Hz, 3H), 1.60-1.53 (m, 4H), 1.44 (dq, J=14.7, 7.6 Hz, 1H), 1.21-1.16 (m, 2H), 0.94 (t, J=7.3 Hz, 1H), 0.87 (td, J=7.4, 2.4 Hz, 3H).

Example 2-16

2-[1-(4-chlorophenyl)ethyl]-N-[(3,3-difluorocyclobutyl)methyl]-5-methylpyrazolo[1,5-a]pyrimidin-7-amine The synthesis was done analogously to the synthesis described in EXAMPLE 2-5 to obtain the titled compound as a clear oil (71.6%). LC-MS (ESI+) m/z 392.1 [M+H]$^+$; $^1$H NMR (600 MHz, DMSO-d$_6$) δ ppm 7.85 (t, J=6.3 Hz, 2H), 7.33 (d, J=0.7 Hz, 8H), 6.15 (s, 2H), 6.08 (s, 2H), 5.76 (s, 1H), 4.29 (q, J=7.2 Hz, 2H), 3.50-3.40 (m, 4H), 3.32 (d, J=5.8 Hz, 1H), 2.69-2.58 (m, 4H), 2.57-2.51 (m, 1H), 2.34 (s, 10H), 1.62 (d, J=7.2 Hz, 6H), 1.04 (d, J=6.1 Hz, 1H).

Example 2-17

N-[(3S)-1-{2-[1-(4-chlorophenyl)ethyl]-5-methylpyrazolo[1,5-a]pyrimidin-7-yl}pyrrolidin-3-yl]acetamide 7-Chloro-2-[1-(4-chlorophenyl)ethyl]-5-methylpyrazolo[1,5-a]pyrimidine (100 mg, 0.327 mmol, INTERMEDIATE a2) was added to a suspension of potassium carbonate (90 mg, 0.653 mmol) and (S)—N-(pyrrolidin-3-yl)acetamide (50.2 mg, 0.392 mmol) in N,N-dimethylformamide (5 mL). The mixture was stirred at 65° C. overnight and then concentrated under vacuum. Purification of the residue by flash chromatography on silica gel eluted with ethyl acetate/petroleum ether (gradient ethyl acetate:petroleum ether from 0:1 to 1:1) provided the titled compound (56.1 mg, 43.2%). MS(ESI+) m/z 398.1 [M+H]$^+$; $^1$H NMR (DMSO-d$_6$) δ ppm 1.59 (d, 3H), 1.81 (s, 3H), 1.88 (m, 1H), 2.12 (m, 1H), 2.29 (s, 3H), 3.83 (m, 3H), 4.07 (m, 1H), 4.23 (q, 1H), 4.32 (m, 1H), 5.79 (s, 1H), 6.01 (s, 1H), 7.33 (m, 4H), 8.18 (d, 1H).

Example 2-18 cis-3-({2-[1-(4-chlorophenyl)ethyl]-5-methylpyrazolo[1,5-a]pyrimidin-7-yl}amino)cyclobutanol The synthesis was done analogously to the synthesis described in EXAMPLE 2-5 to obtain the titled compound as a clear oil (33.1%). LC-MS (ESI+) m/z 357.2 [M+H]$^+$; $^1$H NMR (600 MHz, DMSO-d$_6$) δ ppm 7.65 (d, J=6.6 Hz, 1H), 7.34 (s, 5H), 6.13 (s, 1H), 5.89 (s, 1H), 5.76 (s, 2H), 5.14 (d, J=6.2 Hz, 1H), 4.30 (q, J=7.2 Hz, 1H), 3.93-3.83 (m, 1H), 3.64-3.54 (m, 1H), 3.41-3.26 (m, 3H), 2.71 (dddd, J=12.6, 6.3, 3.7, 1.2 Hz, 2H), 2.33 (s, 3H), 2.07-1.97 (m, 2H), 1.62 (d, J=7.2 Hz, 3H), 1.04 (d, J=6.1 Hz, 1H).

Example 2-19 trans-3-({2-[1-(4-chlorophenyl)ethyl]-5-methylpyrazolo[1,5-a]pyrimidin-7-yl}amino)cyclobutanol The synthesis was done analogously to the synthesis described in EXAMPLE 2-8 to obtain the titled compound as a clear foam (23.29%). LC-MS (ESI+) m/z 357.2 [M+H]$^+$; $^1$H NMR (600 MHz, DMSO-d$_6$) δ ppm 7.70 (d, J=6.1 Hz, 1H), 7.34 (s, 3H), 6.15 (s, 1H), 5.78 (s, 1H), 5.12 (d, J=5.2 Hz, 1H), 4.32 (dq, J=19.1, 7.1 Hz, 2H), 4.18-4.10 (m, 1H), 2.34 (s, 3H), 2.24 (dddd, J=9.7, 7.0, 5.1, 1.7 Hz, 2H), 1.62 (d, J=7.2 Hz, 3H).

Example 2-20

6-{2-[1-(4-chlorophenyl)ethyl]-5-methylpyrazolo[1,5-a]pyrimidin-7-yl}-6-azaspiro[3.4]octan-1-ol The synthesis was done analogously to the synthesis described in EXAMPLE 2-8 to obtain the titled compound as a white solid (74.9%). LC-MS (ESI+) m/z 397.2 [M+H]$^+$.

Example 2-21

2-(1-(4-chlorophenyl)ethyl)-N-(3,3-difluorocyclobutyl)-5-methylpyrazolo[1,5-a]pyrimidin-7-amine The synthesis was done analogously to the synthesis described in EXAMPLE 2-8 to obtain the titled compound as a clear oil (86%). LC-MS (ESI+) m/z 377.1 [M+H]$^+$; $^1$H NMR (500 MHz, DMSO-d$_6$) δ ppm 8.05 (d, J=6.6 Hz, 1H), 7.34 (s, 4H), 6.17 (s, 1H), 6.03 (s, 1H), 4.31 (q, J=7.2 Hz, 1H), 4.08 (p, J=7.1, 6.6 Hz, 1H), 3.60 (p, J=6.1 Hz, 1H), 3.14-2.88 (m, 4H), 2.35 (s, 3H), 1.63 (d, J=7.3 Hz, 3H), 1.04 (d, J=6.1 Hz, 4H).

Example 2-22

2-[1-(4-chlorophenyl)ethyl]-7-[(2R)-2-ethylpiperidin-1-yl]-5-methylpyrazolo[1,5-a]pyrimidine The synthesis was done analogously to the synthesis described in EXAMPLE 2-8 to obtain the titled compound as a clear oil (20.56%). LC-MS (ESI+) m/z 383.2 [M+H]$^+$; $^1$H NMR (500 MHz, DMSO-d$_6$) δ ppm 7.34 (d, J=1.5 Hz, 4H), 6.15-6.09 (m, 2H), 4.97 (s, 1H), 4.29 (qd, J=7.2, 2.4 Hz, 1H), 3.80 (d, J=13.1 Hz, 1H), 3.33-3.22 (m, 3H), 2.36 (s, 3H), 1.76-1.57 (m, 11H), 0.72 (dt, J=13.3, 7.4 Hz, 3H).

Example 2-23

N-[(3R)-1-{2-[1-(4-chlorophenyl)ethyl]-5-methylpyrazolo[1,5-a]pyrimidin-7-yl}pyrrolidin-3-yl]acetamide 7-Chloro-2-[1-(4-chlorophenyl)ethyl]-5-methylpyrazolo[1,5-a]pyrimidine (100 mg, 0.327 mmol, INTERMEDIATE a2) was added to a suspension of potassium carbonate (90 mg, 0.653 mmol) and (R)—N-(pyrrolidin-3-yl)acetamide (46.0 mg, 0.359 mmol) in N,N-dimethylformamide (5 mL). The mixture was stirred at 65° C. overnight and then concentrated under vacuum. Purification of the residue by flash chromatography on silica gel eluted with ethyl acetate/petroleum ether (gradient ethyl acetate:petroleum ether from 0:1 to 1:1) provided the titled compound (37.7 mg, 29.0%). MS(ESI+) m/z 398.1 [M+H]$^+$; $^1$H NMR (400 MHz, DMSO-d$_6$) δ ppm 1.59 (d, 3H), 1.81 (s, 3H), 1.88 (m, 1H), 2.13 (m, 1H), 2.29 (s, 3H), 3.84 (m, 3H), 4.07 (m, 1H), 4.24 (q, 1H), 4.33 (m, 1H), 5.78 (s, 1H), 6.01 (s, 1H), 7.33 (m, 4H), 8.18 (d, 1H).

Preparation of Compounds Derived from Intermediate a3

Example 3-1

2-(1-{2-[1-(4-chlorophenyl)propyl]-5-methylpyrazolo[1,5-a]pyrimidin-7-yl}piperidin-2-yl)ethanol The synthesis was done analogously to the synthesis described in EXAMPLE 2-8 to obtain the titled compound as a white solid (34.9%). LC-MS (ESI+) m/z 413.2 [M+H]$^+$; $^1$H NMR (500 MHz, DMSO-d$_6$) δ ppm 7.41-7.30 (m, 4H), 6.20 (dd, J=21.4, 3.0 Hz, 2H), 5.05-4.96 (m, 1H), 4.58 (q, J=5.3 Hz, 1H), 3.98 (t, J=7.7 Hz, 2H), 3.43-3.32 (m, 2H), 3.31-3.19 (m, 2H), 2.49 (s, 2H), 2.35 (s, 3H), 2.21-2.09 (m, 1H), 2.04-1.91 (m, 1H), 1.91-1.78 (m, 2H), 1.78-1.58 (m, 6H), 0.84 (td, J=7.4, 2.8 Hz, 3H).

Example 3-2

2-[1-(4-chlorophenyl)propyl]-7-(3,3-difluoropiperidin-1-yl)-5-methylpyrazolo[1,5-a]pyrimidine The synthesis was done analogously to the synthesis described in EXAMPLE 2-8 to obtain the titled compound as a clear oil (93%). LC-MS (ESI+) m/z 405.2 [M+H]$^+$; $^1$H NMR (500 MHz, DMSO-d$_6$) δ ppm 7.40-7.30 (m, 7H), 6.31 (s, 2H), 6.26 (s, 2H), 5.76 (s, 1H), 4.28 (t, J=11.9 Hz, 3H), 4.02 (t, J=7.7 Hz, 2H), 3.67 (t, J=5.3 Hz, 3H), 3.29 (s, 1H), 2.39 (s, 5H), 2.22-2.08 (m, 5H), 2.04-1.86 (m, 5H), 0.85 (t, J=7.3 Hz, 5H).

Preparation of Compounds Derived from Intermediate a4

Example 4-1

2-(1-{2-[1-(4-chlorophenyl)-2-methylpropyl]-5-methylpyrazolo[1,5-a]pyrimidin-7-yl}piperidin-2-yl)ethanol The synthesis was done analogously to the synthesis described in EXAMPLE 2-8 to obtain the titled compound as a white solid (37.2%). LC-MS (ESI+) m/z 427.2 [M+H]$^+$; $^1$H NMR (500 MHz, DMSO-d$_6$) δ ppm 7.44 (dd, J=8.6, 2.4 Hz, 2H), 7.32 (dd, J=8.5, 2.1 Hz, 2H), 6.27 (d, J=2.1 Hz, 1H), 6.21 (d, J=6.9 Hz, 1H), 5.01 (d, J=7.7 Hz, 1H), 4.60 (dt, J=18.4, 5.2 Hz, 1H), 3.94 (dd, J=32.5, 12.9 Hz, 1H), 3.68 (d, J=10.0 Hz, 1H), 3.45-3.32 (m, 2H), 3.32-3.20 (m, 1H), 2.46 (ddd, J=13.2, 6.5, 3.4 Hz, 1H), 2.35 (s, 3H), 1.95-1.59 (m, 8H), 0.88 (dd, J=6.6, 1.9 Hz, 3H), 0.77 (d, J=6.6 Hz, 3H).

Example 4-2

2-[1-(4-chlorophenyl)-2-methylpropyl]-7-(3,3-difluoropiperidin-1-yl)-5-methylpyrazolo[1,5-a]pyrimidine The synthesis was done analogously to the synthesis described in EXAMPLE 2-8 to obtain the titled compound as a yellow clear oil (73.8%). LC-MS (ESI+) m/z 419.2 [M+H]$^+$; $^1$H NMR (500 MHz, DMSO-d$_6$) δ ppm 7.48-7.41 (m, 2H), 7.36-7.29 (m, 2H), 6.35 (s, 1H), 6.31 (s, 1H), 4.31 (t, J=12.0 Hz, 2H), 3.76-3.63 (m, 3H), 3.30 (d, J=8.5 Hz, 1H), 2.39 (s, 4H), 2.15 (tt, J=14.0, 6.3 Hz, 2H), 1.91 (p, J=5.7 Hz, 2H), 0.88 (d, J=6.4 Hz, 3H), 0.78 (d, J=6.5 Hz, 3H).

Preparation of Compounds Derived from Intermediate a5

Example 5-1

2-(1-{2-[1-(4-chlorophenyl)butyl]-5-methylpyrazolo[1,5-a]pyrimidin-7-yl}piperidin-2-yl)ethanol The synthesis was done analogously to the synthesis described in EXAMPLE 2-8 to obtain the titled compound as a clear oil (75%). LC-MS (ESI+) m/z 427.2 [M+H]$^+$; $^1$H NMR (500 MHz, DMSO-d$_6$) δ ppm 7.41-7.29 (m, 4H), 6.24-6.16 (m, 2H), 4.59 (q, J=5.1 Hz, 1H), 4.09 (td, J=7.7, 2.8 Hz, 1H), 3.95 (dd, J=21.8, 13.1 Hz, 1H), 3.60 (hept, J=6.1 Hz, 1H), 3.44-3.19 (m, 4H), 2.35 (s, 3H), 2.16-2.03 (m, 1H), 1.99-1.79 (m, 3H), 1.78-1.60 (m, 6H), 1.30-1.17 (m, 2H), 1.04 (d, J=6.1 Hz, 5H), 0.88 (td, J=7.4, 1.0 Hz, 3H).

Example 5-2

2-[1-(4-chlorophenyl)butyl]-7-(3,3-difluoropiperidin-1-yl)-5-methylpyrazolo[1,5-a]pyrimidine The synthesis was done analogously to the synthesis described in EXAMPLE 2-8 to obtain the titled compound as a clear oil (84%). LC-MS (ESI+) m/z 419.2 [M+H]$^+$; $^1$H NMR (500 MHz, DMSO-d$_6$) δ ppm 7.41-7.30 (m, 4H), 6.31 (s, 1H), 6.26 (s, 1H), 4.29 (t, J=11.8 Hz, 2H), 4.13 (t, J=7.8 Hz, 1H), 3.67 (t, J=5.3 Hz, 2H), 3.31 (d, J=8.7 Hz, 1H), 2.39 (s, 3H), 2.21-2.05 (m, 3H), 2.00-1.86 (m, 3H), 1.23 (dddd, J=14.5, 10.9, 7.3, 5.3 Hz, 2H), 0.88 (t, J=7.3 Hz, 3H).

Preparation of Compounds Derived from Intermediate a6

Example 6-1

2-(1-{5-methyl-2-[3-(trifluoromethyl)benzyl]pyrazolo[1,5-a]pyrimidin-7-yl}piperidin-2-yl)ethanol A mixture of 7-chloro-5-methyl-2-[3-(trifluoromethyl)benzyl]pyrazolo[1,5-a]pyrimidine (80 mg, 0.246 mmol, INTERMEDIATE a6), 2-(piperidin-2-yl)ethanol) (63.5 mg, 0.491 mmol), and N-ethyl-N-isopropylpropan-2-amine (127 mg, 0.982 mmol) in ethanol (3 mL) was stirred at room temperature for 12 h and then at 50° C. for 6 h.

For work-up, the reaction mixture was extracted with H$_2$O/CH$_2$Cl$_2$, and the combined organic layers were washed with brine, dried over MgSO$_4$, filtered, and concentrated. After chromatographic purification using a Teledyne Isco CombiFlash® system (normal phase: 4 g column, eluent: 3-5% CH$_3$OH/CH$_2$Cl$_2$), the titled compound was obtained as a clear oil (38 mg, 37.0%). LC-MS (ESI+) m/z 419.2 [M+H]$^+$; $^1$H NMR (600 MHz, DMSO-d$_6$) δ ppm 7.72 (t, J=1.7 Hz, 1H), 7.64-7.50 (m, 3H), 6.26 (s, 1H), 6.15 (s, 1H), 4.97 (d, J=7.7 Hz, 1H), 4.61 (t, J=5.2 Hz, 1H), 4.17 (s, 2H), 3.96 (d, J=12.7 Hz, 1H), 3.41-3.19 (m, 3H), 2.37 (s, 3H), 1.91-1.56 (m, 8H), 1.04 (d, J=6.1 Hz, 2H).

Preparation of Compounds Derived from Intermediate a7

Example 7-1

2-{1-[5-methyl-2-(tricyclo[3.3.1.1$^{3^,7}$]dec-1-ylmethyl)pyrazolo[1,5-a]pyrimidin-7-yl]piperidin-2-yl}ethanol A mixture of INTERMEDIATE a7 (80 mg, 0.253 mmol), 2-(piperidin-2-yl)ethanol (65.5 mg, 0.507 mmol), and N-ethyl-N-isopropylpropan-2-amine (131 mg, 1.013 mmol) in ethanol (3 mL) was stirred at room temperature for 36 h and then at 50° C. for 6 h.

For work-up, the reaction mixture was extracted with H$_2$O/CH$_2$Cl$_2$, and the combined organic layers were washed with brine, dried over MgSO$_4$, filtered, and concentrated. The resultant residue was chromatographically purified using a Teledyne Isco CombiFlash® system (normal phase: 4 g column, eluent: 3-5% CH$_3$OH/CH$_2$Cl$_2$). The material obtained from the chromatography was triturated with ethyl acetate/diisopropyl ether, and the resultant solid was collected by filtration and dried in a vacuum oven overnight to give the titled compound as a white solid (15 mg, 15.0%). LC-MS (ESI+) m/z 409.4 [M+H]$^+$; $^1$H NMR (600 MHz, DMSO-d$_6$) δ ppm 6.22 (s, 1H), 6.07 (s, 1H), 5.05 (s, 1H), 4.67 (dd, J=6.0, 4.7 Hz, 1H), 3.90 (d, J=13.0 Hz, 1H), 3.46-3.35 (m, 2H), 3.35-3.21 (m, 3H), 2.44 (s, 2H), 2.37 (s, 3H), 1.93-1.83 (m, 4H), 1.83-1.58 (m, 11H), 1.57-1.49 (m, 9H).

Preparation of Compounds Derived from Intermediate a8

Example 8-1

(2S)-1-(5-methyl-2-{1-[4-(trifluoromethyl)phenyl]ethyl}pyrazolo[1,5-a]pyrimidin-7-yl)azetidine-2-carboxamide A drop of N,N-dimethylformamide and oxalyl dichloride (2.5 mL) were added to a solution of (2S)-1-(5-methyl-2-{1-[4-(trifluoromethyl)phenyl]ethyl}pyrazolo[1,5-a]pyrimidin-7-yl)azetidine-2-carboxylic acid (100 mg, 0.247 mmol, EXAMPLE 8-10) in dichloromethane (1 mL). The vessel was flushed with argon, and then the mixture was stirred at room temperature for 5 hours. The mixture was then concentrated, and the residue was diluted with dichloromethane (3 mL). Ammonium hydroxide (2.5 mL, aqueous 15 M solution) was added, and the reaction solution was stirred at room temperature overnight. The crude residue was purified by flash chromatography, C18 column (CH$_3$OH/water: gradient from 5:95 to 50:50) provided the titled compound (53.4 mg, 53%). MS (ESI+) m/z 404.1 [M+H]$^+$; $^1$H NMR (400 MHz, CD$_3$OD) δ ppm 1.72 (d, 3H), 2.40 (m, 4H), 2.88 (m, 1H), 4.25 (m, 1H), 4.32 (m, 1H), 4.42 (m, 1H), 5.50 (m, 1H), 5.71 (s, 1H), 5.98 (d, 1H), 7.48 (d, 2H), 7.60 (d, 2H).

Example 8-2

2-[1-(5-methyl-2-{1-[4-(trifluoromethyl)phenyl]ethyl}pyrazolo[1,5-a]pyrimidin-7-yl)piperidin-2-yl]ethanol 7-Chloro-5-methyl-2-{1-[4-(trifluoromethyl)phenyl]ethyl}pyrazolo[1,5-a]pyrimidine (100 mg, 0.294 mmol, INTERMEDIATE a8) and 2-(piperidin-2-yl)ethanol (76 mg, 0.589 mmol) were added to a solution of triethylamine (0.123 mL, 0.883 mmol) in acetonitrile (2 mL). The reaction mixture was stirred overnight at 60° C. under nitrogen and then cooled down to room temperature. Water and ethyl acetate were added, the organic layer was separated and the aqueous layer was extracted with ethyl acetate. The combined organic layers were washed with water and dried over sodium sulfate. After filtration and concentration under reduced pressure, the residue was purified by preparative-HPLC, Column: Waters XBridge® C18, 19×150 mm, 5 μm; Mobile Phase A: water/10 mM NH$_4$HCO$_3$, Mobile Phase B: acetonitrile; Flow rate: 20 mL/minute; Gradient: 38% B to 52% B in 8 minutes; 254 nm, to provide the titled compound (31.3 mg, 24.6%) as a white solid. MS (ESI+) m/z 433.1 [M+H]$^+$; NMR (400 MHz, CD$_3$OD) δ ppm 1.75 (m, 6H), 1.84 (m, 4H), 2.17 (m, 1H), 2.41 (s, 3H), 3.42 (m, 1H), 3.63 (m, 2H), 3.92 (d, 1H), 4.39 (q, 1H), 5.15 (m, 1H), 6.12 (d, 1H), 6.25 (s, 1H), 7.47 (d, 2H), 7.54 (d, 2H).

Example 8-3

5-methyl-7-(2-oxa-6-azaspiro[3.4]oct-6-yl)-2-{1-[4-(trifluoromethyl)phenyl]ethyl}pyrazolo[1,5-a]pyrimidine 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a suspension of potassium carbonate (122 mg, 0.883 mmol) and 2-oxa-6-azaspiro[3.4]octane (40.0 mg, 0.353 mmol) in N,N-dimethylformamide (4 mL). The mixture was stirred at 60° C. overnight. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters XBridge® C18, 19×150 mm, 5 m; mobile phase A: water/10 mM NH$_4$HCO$_3$, mobile phase B: acetonitrile; flow rate: 25 mL/minute; gradient: 25% B to 60% B in 10 minutes; 254 nm) provided the titled compound (8.1 mg, 6.6%). MS(ESI+) m/z 417.1 [M+H]$^+$; $^1$H NMR (400 MHz, CD$_3$OD) δ ppm 1.73 (d, 3H), 2.33 (t, 2H), 2.37 (s, 3H), 3.97 (t, 2H), 4.26 (s, 2H), 4.39 (q, 1H), 4.67 (d, 2H), 4.72 (d, 2H), 5.79 (s, 1H), 6.02 (s, 1H), 7.52 (d, 2H), 7.60 (d, 2H).

Example 8-4

5-methyl-7-(7-oxa-2-azaspiro[3.5]non-2-yl)-2-{1-[4-(trifluoromethyl)phenyl]ethyl}pyrazolo[1,5-a]pyrimidine 7-Chloro-5-methyl-2-{1-[4-(trifluoromethyl)phenyl]ethyl}pyrazolo[1,5-a]pyrimidine (60 mg, 0.177 mmol, INTERMEDIATE a8) was added to a solution of 7-oxa-2-azaspiro[3.5]nonane (57.8 mg, 0.353 mmol) and triethylamine (0.098 mL, 0.706 mmol) in acetonitrile (3 mL). The mixture was stirred at 60° C. overnight under nitrogen. The residue was purified by preparative-HPLC (column: Waters SunFire® C18 19×150 mm, 5 μm; mobile phase A: water/0.05% trifluoroacetic acid, mobile phase B: acetonitrile; flow rate: 20 mL/minute; gradient: 15% B to 50% B in 9 minutes; 254 nm) the titled compound as a trifluoroacetic acid salt (70 mg, 72.8%). MS(ESI+) m/z 431.2 [M+H]$^+$; $^1$H NMR (400 MHz, CD$_3$OD) δ ppm 1.75 (d, 3H), 1.94 (t, 4H), 2.51 (s, 3H), 3.32 (s, 2H), 3.70 (t, 4H), 4.25 (s, 2H), 4.44 (q, 1H), 5.95 (s, 1H), 6.18 (s, 1H), 7.54 (d, 2H), 7.63 (d, 2H).

Example 8-5

(3R)-1-(5-methyl-2-{1-[4-(trifluoromethyl)phenyl]ethyl}pyrazolo[1,5-a]pyrimidin-7-yl)piperidin-3-ol 7-Chloro-5-methyl-2-{1-[4-(trifluoromethyl)phenyl]ethyl}pyrazolo[1,5-a]pyrimidine (80 mg, 0.235 mmol, INTERMEDIATE a8) was added to a solution of triethylamine (23.8 mg, 0.235 mmol) and (R)-piperidin-3-ol (47.6 mg, 0.471 mmol) in acetonitrile (2 mL). The resulting solution was stirred overnight at 60° C. under nitrogen. The reaction mixture was partitioned between water and ethyl acetate, the organic layer was separated, and the aqueous layer was extracted with ethyl acetate. The combined organic layers were washed with water, dried over sodium sulfate and concentrated. Purification of the residue by preparative-HPLC: column: Waters XBridge® C18, 19×150 mm, 5 μm; mobile phase A: water/10 mM NH$_4$HCO$_3$, mobile phase B: acetonitrile; flow rate: 20 mL/minute; gradient: 45% B to 58% B in 8 minutes; 254 nm) provided the titled compound (20.8 mg, 21.8%). MS(ESI+) m/z 405.2 [M+H]$^+$; $^1$H NMR (400 MHz, CD$_3$OD) δ ppm 1.65 (m, 1H), 1.75 (m, 4H), 2.04 (m, 2H), 2.46 (s, 3H), 3.36 (m, 2H), 3.90 (m, 1H), 4.00 (m, 1H), 4.21 (d, 1H), 4.44 (q, 1H), 6.18 (s, 1H), 6.21 (d, 1H), 7.55 (d, 2H), 7.61 (d, 2H).

Example 8-6

N-(3-fluorocyclobutyl)-5-methyl-2-{1-[4-(trifluoromethyl)phenyl]ethyl}pyrazolo[1,5-a]pyrimidin-7-amine 7-Chloro-5-methyl-2-{1-[4-(trifluoromethyl)phenyl]ethyl}pyrazolo[1,5-a]pyrimidine (80 mg, 0.235 mmol, INTERMEDIATE a8) was added to a suspension of potassium carbonate (98 mg, 0.706 mmol) and 3-fluorocyclobutanamine (42.0 mg, 0.471 mmol) in N,N-dimethylformamide (3 mL). The vessel was flushed with argon, and then the mixture was stirred and heated in a microwave (100° C., 300 W, 1 hour). The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters XBridge® C18, 19×150 mm, 5 μm; mobile phase A: Water/10 mM $NH_4HCO_3$, mobile phase B: acetonitrile; flow rate: 20 mL/minute; gradient: 45% B to 58% B in 8 minutes; 254 nm) provided the titled compound (14.6 mg, 15.8%). MS(ESI+) m/z 393.1 [M+H]$^+$; $^1$H NMR (400 MHz, $CD_3OD$) δ ppm 1.76 (d, 3H), 2.38 (m, 1H), 2.45 (s, 3H), 2.60 (m, 1H), 2.75 (m, 1H), 3.02 (m, 1H), 3.81 (m, 0.6H), 4.45 (m, 1.4H), 4.90 (dm, 0.6H), 5.28 (dm, 0.4H), 5.91 (m, 1H), 6.16 (m, 1H), 7.52 (m, 2H), 7.61 (m, 2H).

Example 8-7

N-[(3S)-1-(5-methyl-2-{1-[4-(trifluoromethyl)phenyl]ethyl}pyrazolo[1,5-a]pyrimidin-7-yl)pyrrolidin-3-yl]acetamide 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a solution of triethylamine (89 mg, 0.883 mmol) and (S)—N-(pyrrolidin-3-yl)acetamide (75 mg, 0.589 mmol) in acetonitrile (2 mL). The resulting solution was stirred overnight at 60° C. under nitrogen. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC: column: Waters XBridge® C18, 19×150 mm, 5 μm; mobile phase A: water/10 mM $NH_4HCO_3$, mobile phase B: acetonitrile; flow rate: 20 mL/minute; gradient: 39% B to 53% B in 8 minutes; 254 nm) provided the titled compound (58.6 mg, 46.1%). MS(ESI+) m/z 432.1 [M+H]$^+$; $^1$H NMR (400 MHz, $CD_3OD$) δ ppm 1.68 (d, 3H), 1.90 (s, 3H), 1.97 (m, 1H), 2.21 (m, 1H), 2.33 (s, 3H), 3.96 (m, 3H), 4.19 (m, 1H), 4.31 (q, 1H), 4.43 (m, 1H), 5.74 (s, 1H), 5.98 (s, 1H), 7.47 (d, 2H), 7.55 (d, 2H).

Example 8-8

5-methyl-N-(1-methylcyclopropyl)-2-{1-[4-(trifluoromethyl)phenyl]ethyl}pyrazolo[1,5-a]pyrimidin-7-amine 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a suspension of 1-methylcyclopropanamine hydrochloride (95 mg, 0.883 mmol) and potassium carbonate (122 mg, 0.883 mmol) in N,N-dimethylformamide (3 mL). The vessel was flushed with argon, and then the mixture was stirred and heated in a microwave (100° C., 300 W, 1 hour). The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters XBridge® C18, 19×150 mm, 5 μm; mobile phase A: water/10 mM $NH_4HCO_3$, mobile phase B: acetonitrile; flow rate: 20 mL/minute; gradient: 45% B to 58% B in 8 minutes; 254 nm) provided the titled compound (17.7 mg, 16.1%). MS(ESI+) m/z 375.1 [M+H]$^+$; $^1$H NMR (400 MHz, $CD_3OD$) δ ppm 1.01 (m, 2H), 1.09 (m, 2H), 1.56 (s, 3H), 1.78 (d, 3H), 2.64 (s, 3H), 4.51 (q, 1H), 6.30 (s, 1H), 6.58 (s, 1H), 7.55 (d, 2H), 7.63 (d, 2H).

Example 8-9

[1-(5-methyl-2-{1-[4-(trifluoromethyl)phenyl]ethyl}pyrazolo[1,5-a]pyrimidin-7-yl)piperidin-2-yl]methanol 7-Chloro-5-methyl-2-{1-[4-(trifluoromethyl)phenyl]ethyl}pyrazolo[1,5-a]pyrimidine (80 mg, 0.235 mmol, INTERMEDIATE a8) was added to a suspension of piperidin-2-ylmethanol (81 mg, 0.706 mmol) and potassium carbonate (98 mg, 0.706 mmol) in 1,4-dioxane (2 mL). The resulting solution was stirred at 120° C. for 48 hours. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC: column: Waters XBridge® C18, 19×150 mm, 5 μm; mobile phase A: water/10 mM $NH_4HCO_3$, mobile phase B: acetonitrile; flow rate: 20 mL/minute; gradient: 45% B to 58% B in 8 minutes; 254 nm) provided the titled compound (20.4 mg, 20.7%). MS(ESI+) m/z 419.1 [M+H]$^+$; $^1$H NMR (400 MHz, $CD_3OD$) δ ppm 1.77 (m, 8H), 1.91 (m, 1H), 2.45 (s, 3H), 3.46 (m, 1H), 3.67 (q, 1H), 3.84 (m, 1H), 4.03 (m, 1H), 4.42 (q, 1H), 5.14 (m, 1H), 6.16 (d, 1H), 6.24 (s, 1H), 7.54 (d, 2H), 7.61 (d, 2H).

Example 8-10

(2S)-1-(5-methyl-2-{1-[4-(trifluoromethyl)phenyl]ethyl}pyrazolo[1,5-a]pyrimidin-7-yl)azetidine-2-carboxylic acid 7-Chloro-5-methyl-2-{1-[4-(trifluoromethyl)phenyl]ethyl}pyrazolo[1,5-a]pyrimidine (200 mg, 0.589 mmol, INTERMEDIATE a8) was added to a suspension of (S)-azetidine-2-carboxylic acid (119 mg, 1.177 mmol) and potassium carbonate (244 mg, 1.766 mmol) in 1,4-dioxane (5 mL). The mixture was stirred at 50° C. for 48 hours and then concentrated under vacuum. Purification of the residue by flash chromatography on silica gel eluted with methanol/dichloromethane (gradient from 0:1 to 1:3) provided the titled compound (26.1 mg, 11%). MS(ESI+) m/z 405.1 [M+H]$^+$; $^1$H NMR (400 MHz, $CD_3OD$) δ ppm 1.70 (d, 3H), 2.38 (m, 4H), 2.89 (m, 1H), 3.37 (s, 3H), 4.33 (q, 1H), 5.69 (s, 1H), 5.98 (s, 1H), 7.54 (d, 2H), 7.60 (d, 2H).

Example 8-11

7-(4-fluoropiperidin-1-yl)-5-methyl-2-{1-[4-(trifluoromethyl)phenyl]ethyl}pyrazolo[1,5-a]pyrimidine 7-Chloro-5-methyl-2-{1-[4-(trifluoromethyl)phenyl]ethyl}pyrazolo[1,5-a]pyrimidine (60 mg, 0.177 mmol, INTERMEDIATE a8) was added to a solution of 4-fluoropiperidine hydrochloride (49.3 mg, 0.353 mmol) and triethylamine (0.098 mL, 0.706 mmol) in acetonitrile (3 mL). The mixture was stirred at 60° C. overnight under nitrogen and then concentrated. The crude residue was purified by preparative-HPLC (column: Waters SunFire® C18 19×150 mm, 5 μm; mobile phase A: water/0.05% trifluoroacetic acid, mobile phase B: acetonitrile; flow rate: 20 mL/minute; gradient: 15% B to 50% B in 11 minutes; 254 nm) to provide the titled compound as a trifluoroacetic acid salt (55 mg, 59.8%). MS(ESI+) m/z 407.1 [M+H]$^+$; $^1$H NMR (400 MHz, CD$_3$OD) δ ppm 1.77 (d, 3H), 2.12 (m, 4H), 2.56 (s, 3H), 4.14 (m, 2H), 4.48 (q, 1H), 4.50 (m, 2H), 5.06 (m, 1H), 6.29 (s, 1H), 6.51 (s, 1H), 7.55 (d, 2H), 7.63 (d, 2H).

Example 8-12

7-(3-fluoropiperidin-1-yl)-5-methyl-2-{1-[4-(trifluoromethyl)phenyl]ethyl}pyrazolo[1,5-a]pyrimidine 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a suspension of 3-fluoropiperidine (91 mg, 0.883 mmol) and potassium carbonate (81 mg, 0.589 mmol) in 1,4-dioxane (3 mL). The mixture was stirred at 50° C. for 48 hours and then concentrated under vacuum. Purification of the residue by flash chromatography on silica gel eluted with ethyl acetate/petroleum ether (gradient ethyl acetate:petroleum ether from 0:1 to 1:1) provided the titled compound (20.9 mg, 17.5%). MS(ESI+) m/z 407.1 [M+H]$^+$; $^1$H NMR (400 MHz, CD$_3$OD) δ ppm 1.72 (m, 1H), 1.76 (d, 3H), 2.05 (m, 3H), 2.46 (s, 3H), 3.58 (m, 1H), 3.88 (m, 2H), 4.19 (m, 1H), 4.43 (q, 1H), 4.77 (m, 0.7H), 4.88 (m, 0.3H), 6.17 (s, 1H), 6.22 (s, 1H), 7.53 (d, 2H), 7.61 (d, 2H).

Example 8-13

3-(2-hydroxyethyl)-4-(5-methyl-2-{1-[4-(trifluoromethyl)phenyl]ethyl}pyrazolo[1,5-a]pyrimidin-7-yl)piperazin-2-one 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a suspension of 3-(2-hydroxyethyl)piperazin-2-one (42.4 mg, 0.294 mmol) and potassium carbonate (61.0 mg, 0.442 mmol) in N,N-dimethylformamide (4 mL). The mixture was stirred at 65° C. overnight and then concentrated under vacuum. The residue was purified by preparative-HPLC (column: Waters XBridge® C18, 19×150 mm, 5 μm; mobile phase A: water/0.05% trifluoroacetic acid, mobile phase B: acetonitrile; flow rate: 25 mL/minute; gradient: 25% B to 60% B in 10 minutes; 254 nm) to provide the titled compound as a trifluoroacetic acid salt (44.0 mg, 26.6%). MS(ESI+) m/z 448.1 [M+H]$^+$; $^1$H NMR (400 MHz, CD$_3$OD) δ ppm 1.76 (d, 3H), 2.35 (m, 2H), 2.54 (s, 3H), 3.42 (m, 1H), 3.63 (m, 2H), 3.84 (m, 2H), 4.49 (q, 1H), 5.31 (brs, 1H), 5.60 (brs, 1H), 6.30 (s, 1H), 6.72 (s, 1H), 7.53 (d, 2H), 7.61 (d, 2H).

Example 8-14

N-[(3,3-difluorocyclobutyl)methyl]-5-methyl-2-{1-[4-(trifluoromethyl)phenyl]ethyl}pyrazolo[1,5-a]pyrimidin-7-amine 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a suspension of (3,3-difluorocyclobutyl)methanamine (39.2 mg, 0.324 mmol) and sodium carbonate (62.4 mg, 0.589 mmol) in N,N-dimethylformamide (3 mL). The vessel was flushed with argon, and then the mixture was stirred and heated in the microwave (100° C., 300 W, 1 hour). The final mixture was concentrated under vacuum. The residue was purified by flash chromatography on silica gel eluted with ethyl acetate/petroleum ether (gradient ethyl acetate:petroleum ether from 0:1 to 1:1) to provide the titled compound (57.8 mg, 46.3%). MS(ESI+) m/z 425.2 [M+H]$^+$; $^1$H NMR (400 MHz, CD$_3$OD) δ ppm 1.79 (d, 3H), 2.47 (m, 2H), 2.60 (s, 3H), 2.75 (m, 3H), 3.76 (d, 2H), 4.54 (q, 1H), 6.32 (s, 1H), 6.53 (s, 1H), 7.55 (d, 2H), 7.63 (d, 2H).

Example 8-15

7-(3,3-difluoropyrrolidin-1-yl)-5-methyl-2-{1-[4-(trifluoromethyl)phenyl]ethyl}pyrazolo[1,5-a]pyrimidine 7-Chloro-5-methyl-2-{1-[4-(trifluoromethyl)phenyl]ethyl}pyrazolo[1,5-a]pyrimidine (60 mg, 0.177 mmol, INTERMEDIATE a8) was added to a solution of 3,3-difluoropyrrolidine hydrochloride (50.7 mg, 0.353 mmol) and triethylamine (0.098 mL, 0.706 mmol) in acetonitrile (3 mL). The mixture was stirred at 60° C. overnight under nitrogen. The residue was purified by preparative-HPLC (column: Waters SunFire® C18 19×150 mm, 5 μm; mobile phase A: water/0.05% trifluoroacetic acid, mobile phase B: acetonitrile; flow rate: 20 mL/minute; gradient: 10% B to 55% B in 9 minutes; 254 nm) to provide the titled compound as a trifluoroacetic acid salt (46.3 mg, 50.0%). MS(ESI+) m/z 411.2 [M+H]$^+$; $^1$H NMR (400 MHz, CD$_3$OD) δ ppm 1.77 (d, 3H), 2.56 (s, 3H), 2.68 (m, 2H), 4.39 (m, 2H), 4.48 (q, 1H), 4.73 (m, 2H), 6.24 (s, 1H), 6.27 (s, 1H), 7.55 (d, 2H), 7.64 (d, 2H).

Example 8-16

N-[(3R)-1-(5-methyl-2-{1-[4-(trifluoromethyl)phenyl]ethyl}pyrazolo[1,5-a]pyrimidin-7-yl)pyrrolidin-3-yl]acetamide 7-Chloro-5-methyl-2-{1-[4-(trifluoromethyl)phenyl]ethyl}pyrazolo[1,5-a]pyrimidine (50 mg, 0.147 mmol, INTERMEDIATE a8) was added to a solution of triethylamine (44.7 mg, 0.442 mmol) and (R)—N-(pyrrolidin-3-yl)acetamide (18.9 mg, 0.147 mmol) in acetonitrile (2 mL). The resulting solution was stirred overnight at 60° C. under nitrogen. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters XBridge® C18, 19×150 mm, 5 m; mobile phase A: water/10 mM NH$_4$HCO$_3$, mobile phase B: acetonitrile; flow rate: 20 mL/minute; gradient: 38% B to 52% B in 8 minutes; 254 nm) provided the titled compound (32.9 mg, 51.8%). MS(ESI+) m/z 432.1 [M+H]$^+$; $^1$H NMR (400 MHz, CD$_3$OD) δ ppm 1.68 (d, 3H), 1.90 (s, 3H), 2.01 (m, 1H), 2.21 (m, 1H), 2.33 (s, 3H), 3.94 (m, 3H), 4.23 (m, 1H), 4.34 (q, 1H), 4.45 (m, 1H), 5.76 (s, 1H), 5.99 (s, 1H), 7.49 (d, 2H), 7.56 (d, 2H).

Example 8-17

7-(3,3-difluoropiperidin-1-yl)-5-methyl-2-{1-[4-(trifluoromethyl)phenyl]ethyl}pyrazolo[1,5-a]pyrimidine 7-Chloro-5-methyl-2-{1-[4-(trifluoromethyl)phenyl]ethyl}pyrazolo[1,5-a]pyrimidine (60 mg, 0.177 mmol, INTERMEDIATE a8) was added to a solution of 3,3-difluoropiperidine hydrochloride (55.7 mg, 0.353 mmol) and triethylamine (0.098 mL, 0.706 mmol) in acetonitrile (3 mL). The mixture was stirred at 60° C. overnight under nitrogen. The residue was purified by preparative-HPLC (column: Waters SunFire® C18 19×150 mm, 5 m; mobile phase A: water/0.05% trifluoroacetic acid, mobile phase B: acetonitrile; flow rate: 20 mL/minute; gradient: 15% B to 50% B in 9 minutes; 254 nm) to provide the titled compound (13.6 mg, 18.14%). MS(ESI+) m/z 425.1 [M+H]$^+$; $^1$H NMR (400 MHz, CD$_3$OD) δ ppm 1.76 (d, 3H), 2.01 (m, 2H), 2.19 (m, 2H), 2.48 (s, 3H), 3.78 (m, 2H), 4.27 (m, 2H), 4.46 (q, 1H), 6.20 (s, 1H), 6.26 (s, 1H), 7.54 (d, 2H), 7.61 (d, 2H).

Example 8-18

1-(5-methyl-2-{1-[4-(trifluoromethyl)phenyl]ethyl}pyrazolo[1,5-a]pyrimidin-7-yl)piperidin-2-one (9,9-Dimethyl-9H-xanthene-4,5-diyl)bis(diphenylphosphine) (6.81 mg, 0.012 mmol) was added to a suspension of 7-chloro-5-methyl-2-{1-[4-(trifluoromethyl)phenyl]ethyl}pyrazolo[1,5-a]pyrimidine (80 mg, 0.235 mmol, INTERMEDIATE a8), cesium carbonate (230 mg, 0.706 mmol), palladium(II) acetate (52.9 mg, 0.235 mmol) and piperidin-2-one (23.34 mg, 0.235 mmol) in N,N-dimethylformamide (3 mL). The resulting solution was stirred at 130° C. for 48 hours. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters SunFire® C18, 19×150 mm, 5 μm; mobile phase A: water/ 0.05% trifluoroacetic acid, mobile phase B: acetonitrile; flow rate: 30 mL/minute; gradient: 28% B to 60% B in 11 minutes; 254 nm) provided the titled compound as a trifluoroacetic acid salt (9.7 mg, 7.98%). MS(ESI+) m/z 403.1 [M+H]$^+$; $^1$H NMR (400 MHz, CD$_3$OD) δ ppm 1.78 (d, 3H), 2.05 (m, 4H), 2.60 (s, 3H), 2.63 (m, 2H), 3.80 (m, 2H), 4.47 (q, 1H), 6.48 (s, 1H), 6.92 (s, 1H), 7.53 (d, 2H), 7.61 (d, 2H).

Example 8-19

N-tert-butyl-5-methyl-2-{1-[4-(trifluoromethyl)phenyl]ethyl}pyrazolo[1,5-a]pyrimidin-7-amine 7-Chloro-5-methyl-2-{1-[4-(trifluoromethyl)phenyl]ethyl}pyrazolo[1,5-a]pyrimidine (80 mg, 0.235 mmol, INTERMEDIATE a8) was added to a suspension of potassium carbonate (98 mg, 0.706 mmol) and 2-methylpropan-2-amine (51.7 mg, 0.706 mmol) in N,N-dimethylformamide (2 mL). The vessel was flushed with argon, and then the mixture was stirred and heated in a microwave (100° C., 300 W, 1 hour). The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters XBridge® C18, 19×150 mm, 5 m; mobile phase A: water/10 mM NH$_4$HCO$_3$, mobile phase B: acetonitrile; flow rate: 20 mL/minute; gradient: 45% B to 58% B in 8 minutes; 254 nm) provided the titled compound (33.9 mg, 29.4%). MS(ESI+) m/z 377.1 [M+H]$^+$; $^1$H NMR (400 MHz, CD$_3$OD) δ ppm 1.66 (s, 9H), 1.78 (d, 3H), 2.64 (s, 3H), 4.54 (q, 1H), 6.34 (m, 1H), 6.64 (s, 1H), 7.56 (d, 2H), 7.64 (d, 2H).

Example 8-20

N-(3,3-difluorocyclobutyl)-5-methyl-2-{1-[4-(trifluoromethyl)phenyl]ethyl}pyrazolo[1,5-a]pyrimidin-7-amine 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a suspension of potassium carbonate (122 mg, 0.883 mmol) and 3,3-difluorocyclobutanamine (63 mg, 0.589 mmol) in N,N-dimethylformamide (3 mL). The vessel was flushed with argon, and then the mixture was stirred and heated in a microwave (100° C., 300 W, 1 hour). The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters HSS C18, 2.1×50 mm, 1.8 μm; mobile phase A: water/ 0.05% trifluoroacetic acid, mobile phase B: acetonitrile/ 0.05% trifluoroacetic acid B: acetonitrile; flow rate: 0.7 mL/minute; gradient: 5% B to 55% B in 8.0 minutes; 254 nm) provided the titled compound as a trifluoroacetic acid salt (64 mg, 41.5%). MS(ESI+) m/z 411.1 [M+H]$^+$; $^1$H NMR (400 MHz, CD$_3$OD) δ ppm 1.78 (d, 3H), 2.60 (s, 3H), 2.99 (m, 2H), 3.18 (m, 2H), 4.42 (m, 1H), 4.53 (q, 1H), 6.34 (s, 1H), 6.41 (s, 1H), 7.56 (d, 2H), 7.63 (d, 2H).

Example 8-21

5-methyl-7-(2-oxa-7-azaspiro[3.5]non-7-yl)-2-{1-[4-(trifluoromethyl)phenyl]ethyl}pyrazolo[1,5-a]pyrimidine 7-Chloro-5-methyl-2-{1-[4-(trifluoromethyl)phenyl]ethyl}pyrazolo[1,5-a]pyrimidine (100 mg, 0.294 mmol, INTERMEDIATE a8) was added to a suspension of 2-oxa-7-azaspiro[3.5]nonane (74.9 mg, 0.589 mmol) and potassium carbonate (122 mg, 0.883 mmol) in 1,4-dioxane (3 mL). The mixture was stirred at 50° C. for 48 hours and then concentrated under vacuum. Purification of the residue by flash chromatography on silica gel eluted with ethyl acetate/ petroleum ether (gradient ethyl acetate:petroleum ether from 0:1 to 1:1) provided the titled compound (31.3 mg, 24.7%). MS(ESI+) m/z 431.2 [M+H]$^+$; $^1$H NMR (400 MHz, CD₃OD) δ ppm 1.72 (d, 3H), 1.89 (t, 4H), 2.38 (s, 3H), 3.69 (t, 4H), 4.28 (m, 4H), 4.36 (q, 1H), 5.63 (s, 1H), 6.01 (s, 1H), 7.52 (d, 2H), 7.60 (d, 2H).

Example 8-22

1-(5-methyl-2-{1-[4-(trifluoromethyl)phenyl] ethyl}pyrazolo[1,5-a]pyrimidin-7-yl)pyrrolidine-3-carboxamide 7-Chloro-5-methyl-2-{1-[4-(trifluoromethyl)phenyl] ethyl}pyrazolo[1,5-a]pyrimidine (100 mg, 0.294 mmol, INTERMEDIATE a8) was added to a suspension of pyrrolidine-3-carboxamide (40.3 mg, 0.353 mmol) and sodium carbonate (62.4 mg, 0.589 mmol) in N,N-dimethylformamide (5 mL). The vessel was flushed with argon, and then the mixture was stirred and heated in a microwave (100° C., 300 W, 1 hour). The final mixture was concentrated under vacuum. Purification of the residue by flash chromatography on silica gel eluted with ethyl acetate/petroleum ether (gradient ethyl acetate:petroleum ether from 0:1 to 1:1) provided the titled compound (27.7 mg, 22.54%). MS(ESI+) m/z 418.2 [M+H]⁺; ¹H NMR (400 MHz, CDCl3) 1.68 (d, 3H), 2.37 (m, 2H), 2.50 (s, 3H), 3.27 (m, 1H), 4.06 (m, 1H), 4.29 (q, 1H), 4.70 (m, 1H), 5.70 (m, 2H), 6.33 (s, 1H), 6.55 (s, 1H), 7.37 (d, 2H), 7.55 (d, 2H).

Preparation of Compounds Derived from Intermediate a9

Example 9-1

(1-{2-[1-(5-chloropyridin-2-yl)ethyl]-5-methylpyrazolo[1,5-a]pyrimidin-7-yl}piperidin-3-yl)methanol 7-Chloro-2-[1-(5-chloropyridin-2-yl)ethyl]-5-methylpyrazolo[1,5-a]pyrimidine (100 mg, 0.326 mmol, INTERMEDIATE a9) was added to a suspension of potassium carbonate (45.0 mg, 0.326 mmol) and piperidin-3-ylmethanol (41.2 mg, 0.358 mmol) in N,N-dimethylformamide (6 mL). The mixture was stirred at 50° C. overnight. The reaction mixture was partitioned between water and ethyl acetate, the organic layer was separated, and the aqueous layer was extracted with ethyl acetate. The combined organic layers were washed with water, dried over sodium sulfate, and concentrated. Purification of the residue by preparative-HPLC (column: Waters XBridge® C18, 19×150 mm, 5 μm; mobile phase A: Water/10 mM NH₄HCO₃, mobile phase B: acetonitrile; flow rate: 20 mL/minute; gradient: 30% B to 70% B in 10 minutes; 254 nm) provided the titled compound (44.1 mg, 35.1%). MS (ESI+) m/z 386.1 [M+H]⁺; ¹H NMR (400 MHz, CD₃OD) δ ppm 1.41 (m, 1H), 1.72 (d, 3H), 1.85 (m, 4H), 2.41 (s, 3H), 3.15 (m, 2H), 3.52 (m, 2H), 4.17 (m, 2H), 4.45 (q, 1H), 6.17 (d, 2H), 7.39 (d, 1H), 7.76 (d, 1H), 8.41 (s, 1H).

Example 9-2

2-[1-(5-chloropyridin-2-yl)ethyl]-N-(3,3-difluorocyclobutyl)-5-methylpyrazolo[1,5-a]pyrimidin-7-amine 7-Chloro-2-[1-(5-chloropyridin-2-yl)ethyl]-5-methylpyrazolo[1,5-a]pyrimidine (80 mg, 0.260 mmol, INTERMEDIATE a9) was added to a suspension of cesium carbonate (85 mg, 0.26 mmol), 3,3-difluorocyclobutanamine hydrochloride (37.4 mg, 0.260 mmol) and potassium iodide (43.2 mg, 0.260 mmol) in 1,4-dioxane (5 mL). The mixture was stirred at 100° C. for 10 hours then concentrated under vacuum. The residue was purified by preparative-HPLC (column: Waters XBridge® C18, 19×150 mm, 5 μm; mobile phase A: Water/0.5% NH₄HCO₃, mobile phase B: acetonitrile; flow rate: 20 mL/minute; gradient: 30% B to 70% B in 10 minutes; 254 nm) to provide the titled compound (26.7 mg, 27.1%). MS(ESI+) m/z 378.1 [M+H]⁺; ¹H NMR (400 MHz, CD₃OD) δ ppm 1.74 (d, 3H), 2.42 (s, 3H), 2.79 (m, 2H), 3.13 (m, 2H), 4.13 (m, 1H), 4.48 (q, 1H), 5.95 (s, 1H), 6.16 (s, 1H), 7.37 (d, 1H), 7.75 (d, 1H), 8.45 (s, 1H).

Example 9-3

(3S)-1-{2-[1-(5-chloropyridin-2-yl)ethyl]-5-methylpyrazolo[1,5-a]pyrimidin-7-yl}piperidin-3-ol 7-Chloro-2-[1-(5-chloropyridin-2-yl)ethyl]-5-methylpyrazolo[1,5-a]pyrimidine (80 mg, 0.260 mmol, INTERMEDIATE a9) was added to a solution of (S)-piperidin-3-ol (52.7 mg, 0.521 mmol) and triethylamine (79 mg, 0.781 mmol) in acetonitrile (10 mL). The mixture was stirred at 80° C. for 4 hours and then concentrated under vacuum. The residue was purified by preparative-HPLC (column: Waters XBridge® C18, 19×150 mm, 5 μm; mobile phase A: water/0.05% NH₄HCO₃, mobile phase B: acetonitrile; flow rate: 20 mL/minute; gradient: 30% B to 70% B in 10 minutes; 254 nm) provided the titled compound (55.4 mg, 57.2%). MS(ESI+) m/z 372.1 [M+H]⁺; ¹H NMR (400 MHz, CD₃OD) δ ppm 1.69 (m, 2H), 1.78 (d, 3H), 2.03 (m, 2H), 2.47 (s, 3H), 3.36 (m, 2H), 3.90 (m, 2H), 4.19 (m, 1H), 4.51 (q, 1H), 6.21 (m, 2H), 7.42 (d, 1H), 7.80 (d, 1H), 8.49 (s, 1H).

Example 9-4

2-[1-(5-chloropyridin-2-yl)ethyl]-7-(3,3-difluoropiperidin-1-yl)-5-methylpyrazolo[1,5-a]pyrimidine 7-Chloro-2-[1-(5-chloropyridin-2-yl)ethyl]-5-methylpyrazolo[1,5-a]pyrimidine (60 mg, 0.195 mmol, INTERMEDIATE a9) was added to a suspension of potassium carbonate (81 mg, 0.586 mmol) and 3,3-difluoropiperidine (71.0 mg, 0.586 mmol) in 1,4-dioxane (10 mL). The mixture was stirred at 100° C. for 10 hours and then concentrated under vacuum. The crude residue was purified by preparative-HPLC (column: Waters XBridge® C18, 19×150 mm, 5 μm; mobile phase A: water/0.5% NH₄HCO₃, mobile phase B: acetonitrile; flow rate: 20 mL/minute; gradient: 30% B to 70% B in 10 minutes; 254 nm) to provide the titled compound (32 mg, 41.8%). MS(ESI+) m/z 392.0 [M+H]⁺; ¹H NMR (400 MHz, CD₃OD) δ ppm 1.78 (d, 3H), 1.97 (m, 2H), 2.17 (m, 2H), 2.48 (s, 3H), 3.76 (m, 2H), 4.22 (m, 2H), 4.51 (q, 1H), 6.24 (s, 1H), 6.26 (s, 1H), 7.41 (d, 1H), 7.80 (d, 1H), 8.49 (s, 1H).

Example 9-5

2-[1-(5-chloropyridin-2-yl)ethyl]-7-(3,3-difluoropyrrolidin-1-yl)-5-methylpyrazolo[1,5-a]pyrimidine 7-Chloro-2-[1-(5-chloropyridin-2-yl)ethyl]-5-methylpyrazolo[1,5-a]pyrimidine (60 mg, 0.195 mmol, INTERMEDIATE a9) was added to a suspension of 3,3-difluoropyrrolidine hydrochloride (84 mg, 0.586 mmol) and potassium carbonate (81 mg, 0.586 mmol) in 1,4-dioxane (10 mL). The mixture was stirred at 100° C. for 10 hours and then concentrated under vacuum. The crude residue was purified by preparative-HPLC (column: Waters XBridge® C18, 19×150 mm, 5 μm; mobile phase A: water/0.5% NH₄HCO₃, mobile phase B: acetonitrile; flow rate: 20 mL/minute; gradient: 30% B to 70% B in 10 minutes; 254 nm) to provide the titled compound (4.4 mg, 5.96%). MS(ESI+) m/z 378.0 [M+H]⁺; ¹H NMR (400 MHz, CD₃OD) δ ppm 1.63 (d, 3H), 2.30 (s, 3H), 2.45 (m, 2H), 3.94 (t, 2H), 4.34 (m, 3H), 5.77 (s, 1H), 5.99 (s, 1H), 7.28 (d, 1H), 7.68 (d, 1H), 8.36 (s, 1H).

Example 9-6

N-tert-butyl-2-[1-(5-chloropyridin-2-yl)ethyl]-5-methylpyrazolo[1,5-a]pyrimidin-7-amine 7-Chloro-2-[1-(5-chloropyridin-2-yl)ethyl]-5-methyl-pyrazolo[1,5-a]pyrimidine (80 mg, 0.260 mmol, INTERMEDIATE a9) was added to a solution of 2-methylpropan-2-amine hydrochloride (285 mg, 2.60 mmol) and triethylamine (79 mg, 0.781 mmol) in 1,4-dioxane (5 mL). The resulting mixture was stirred at 130° C. for 24 hours. This reaction mixture was concentrated under vacuum and the residue was purified by preparative-HPLC (column: Waters XBridge® C18, 19×150 mm, 5 μm; mobile phase A: water/0.5% NH₄HCO₃, mobile phase B: acetonitrile; flow rate: 20 mL/minute; gradient: 30% B to 70% B in 10 minutes; 254 nm) to provide the titled compound (55.2 mg, 61.6%). MS(ESI+) m/z 344.1 [M+H]⁺; ¹H NMR (400 MHz, CD₃OD) δ ppm 1.56 (s, 9H), 1.75 (d, 3H), 2.45 (s, 3H), 4.47 (q, 1H), 6.15 (s, 1H), 6.18 (s, 1H), 7.37 (d, 1H), 7.77 (dd, 1H), 8.47 (d, 1H).

Example 9-7

2-[1-(5-chloropyridin-2-yl)ethyl]-5-methyl-N-(1-methylcyclopropyl)pyrazolo[1,5-a]pyrimidin-7-amine 7-Chloro-2-[1-(5-chloropyridin-2-yl)ethyl]-5-methyl-pyrazolo[1,5-a]pyrimidine (80 mg, 0.260 mmol, INTERMEDIATE a9) was added to a suspension of 1-methylcyclopropanamine hydrochloride (140 mg, 1.302 mmol), potassium iodide (43.2 mg, 0.260 mmol) and cesium carbonate (255 mg, 0.781 mmol) in 1,4-dioxane (5 mL). The resulting mixture was stirred at 130° C. for 4 hours. This reaction mixture was concentrated under vacuum, and the crude residue was purified by preparative-HPLC (column: Waters XBridge® C18, 19×150 mm, 5 μm; mobile phase A: water/0.05% NH₄HCO₃, mobile phase B: acetonitrile; flow rate: 20 mL/minute; gradient: 30% B to 70% B in 10 minutes; 254 nm) to provide the titled compound (22.1 mg, 24.8%). MS(ESI+) m/z 342.1 [M+H]⁺; ¹H NMR (400 MHz, CD₃OD) δ ppm 0.89 (m, 2H), 0.98 (m, 2H), 1.51 (s, 3H), 1.77 (d, 3H), 2.50 (s, 3H), 4.50 (q, 1H), 6.17 (s, 1H), 6.27 (s, 1H), 7.40 (d, 1H), 7.79 (dd, 1H), 8.49 (d, 1H).

Example 9-8

2-[1-(5-chloropyridin-2-yl)ethyl]-N-(3-fluorocyclobutyl)-5-methylpyrazolo[1,5-a]pyrimidin-7-amine 7-Chloro-2-[1-(5-chloropyridin-2-yl)ethyl]-5-methyl-pyrazolo[1,5-a]pyrimidine (100 mg, 0.326 mmol, INTERMEDIATE a9) was added to a suspension of potassium carbonate (135 mg, 0.977 mmol) and 3-fluorocyclobutanamine hydrochloride (49.1 mg 0.391 mmol) in N,N-dimethylformamide (2 mL). The vessel was flushed with argon, and then the mixture was stirred and heated in a microwave (100° C., 300 W, 1 hour). The final mixture was concentrated under vacuum. The residue was purified by preparative-HPLC (column: Waters XBridge® C18 19×150; mobile phase A: water/10 mM NH₄HCO₃, mobile phase B: acetonitrile; flow rate: 25 mL/minute; gradient: 10% B to 60% B in 7 minutes; 254 nm) to provide the titled compound (56.3 mg, 37%). MS(ESI+) m/z 360.1 [M+H]⁺; ¹H NMR (400 MHz, CD₃OD) δ ppm 1.78 (d, 3H), 2.50 (m, 1H), 2.59 (s, 3H), 2.76 (m, 1H), 3.03 (m, 2H), 4.03 (m, 0.5H), 4.58 (q, 1H), 4.84 (m, 1H), 5.04 (m, 0.5H), 6.35 (s, 1H), 6.36 (s, 1H), 7.43 (d, 1H), 7.80 (d, 1H), 8.50 (s, 1H).

Example 9-9

2-[1-(5-chloropyridin-2-yl)ethyl]-5-methyl-7-(7-oxa-2-azaspiro[3.5]non-2-yl)pyrazolo[1,5-a]pyrimidine 7-Chloro-2-[1-(5-chloropyridin-2-yl)ethyl]-5-methyl-pyrazolo[1,5-a]pyrimidine (100 mg, 0.326 mmol, INTERMEDIATE a9) was added to a suspension of 7-oxa-2-azaspiro[3.5]nonane hydrochloride (63.9 mg, 0.391 mmol) and potassium carbonate (135 mg, 0.977 mmol) in N,N-dimethylformamide (2 mL). The vessel was flushed with argon, and then the mixture was stirred and heated in a microwave (100° C., 300 W, 1 hour). The final mixture was concentrated under vacuum. The residue was purified by preparative-HPLC (column: Waters XBridge® C18 19×150 mm, 5 μm; mobile phase A: water/10 mM NH₄HCO₃, mobile phase B: acetonitrile; flow rate: 25 mL/minute; gradient: 10% B to 60% B in 7 minutes; 254 nm) to provide the titled compound (81 mg, 61.9%). MS(ESI+) m/z 398.1 [M+H]⁺; ¹H NMR (400 MHz, CD₃OD) δ ppm 1.75 (d, 3H), 1.92 (t, 4H), 2.49 (s, 3H), 3.32 (s, 2H), 3.69 (t, 4H), 4.23 (s, 2H), 4.49 (q, 1H), 5.93 (s, 1H), 6.21 (s, 1H), 7.43 (d, 1H), 7.82 (d, 1H), 8.49 (s, 1H).

Example 9-10

N-[(3R)-1-{2-[1-(5-chloropyridin-2-yl)ethyl]-5-methylpyrazolo[1,5-a]pyrimidin-7-yl}pyrrolidin-3-yl]acetamide 7-Chloro-2-[1-(5-chloropyridin-2-yl)ethyl]-5-methyl-pyrazolo[1,5-a]pyrimidine (80 mg, 0.260 mmol, INTERMEDIATE a9) was added to a suspension of (R)—N-(pyrrolidin-3-yl)acetamide (66.8 mg, 0.521 mmol) and potassium carbonate (108 mg, 0.781 mmol) in 1,4-dioxane (5 mL). The resulting mixture was stirred at 90° C. for 10 hours. This reaction mixture was concentrated under vacuum, and the residue was purified by preparative-HPLC (column: Waters XBridge® C18, 19×150 mm, 5 m; mobile phase A: water/0.05% NH₄HCO₃, mobile phase B: acetonitrile; flow rate: 20 mL/minute; gradient: 30% B to 70% B in 10 minutes; 254 nm) to provide the titled compound (31 mg, 29.8%). MS(ESI+) m/z 399.1 [M+H]⁺; ¹H NMR (400 MHz, CD₃OD) δ ppm 1.70 (d, 3H), 1.94 (s, 3H), 2.00 (m, 1H), 2.23 (m, 1H), 2.35 (s, 3H), 3.95 (m, 3H), 4.18 (m, 1H), 4.45 (m, 2H), 5.76 (s, 1H), 6.03 (s, 1H), 7.37 (d, 1H), 7.76 (dd, 1H), 8.44 (d, 1H).

Example 9-11

N-[(3S)-1-{2-[1-(5-chloropyridin-2-yl)ethyl]-5-methylpyrazolo[1,5-a]pyrimidin-7-yl}pyrrolidin-3-yl]acetamide 7-Chloro-2-[1-(5-chloropyridin-2-yl)ethyl]-5-methyl-pyrazolo[1,5-a]pyrimidine (100 mg, 0.326 mmol, INTER- MEDIATE a9) was added to a suspension of (S)—N-(pyrrolidin-3-yl)acetamide (83 mg, 0.651 mmol) and potassium carbonate (135 mg, 0.977 mmol) in 1,4-dioxane (5 mL). The resulting mixture was stirred at 90° C. for 10 hours. This reaction mixture was concentrated under vacuum, and the residue was purified by preparative-HPLC (column: Waters XBridge® C18, 19×150 mm, 5 m; mobile phase A: water/0.05% $NH_4HCO_3$, mobile phase B: acetonitrile; flow rate: 20 mL/minute; gradient: 30% B to 70% B in 10 minutes; 254 nm) to provide the titled compound (19.8 mg, 15.2%). MS(ESI+) m/z 399.1 $[M+H]^+$; $^1H$ NMR (400 MHz, $CD_3OD$) δ ppm 1.71 (d, 3H), 1.94 (s, 3H), 2.00 (m, 1H), 2.23 (m, 1H), 2.36 (s, 3H), 3.97 (m, 3H), 4.19 (m, 1H), 4.46 (m, 2H), 5.77 (s, 1H), 6.03 (s, 1H), 7.37 (d, 1H), 7.76 (dd, 1H), 8.44 (d, 1H).

Preparation of Compounds Derived from Intermediate a10

Example 10-1

N-{(3R)-1-[2-(4-chlorobenzyl)-5-methylpyrazolo[1,5-a]pyrimidin-7-yl]pyrrolidin-3-yl}methanesulfonamide Methanesulfonyl chloride (32.2 mg, 0.281 mmol) was added to a solution of (3R)-1-[2-(4-chlorobenzyl)-5-methylpyrazolo[1,5-a]pyrimidin-7-yl]pyrrolidin-3-amine (80 mg, 0.234 mmol, INTERMEDIATE a10) and triethylamine (47.4 mg, 0.468 mmol) in dichloromethane (10 mL). The mixture was stirred at room temperature for 1 hour. The final mixture was concentrated under vacuum. Purification of the residue by flash chromatography on silica gel eluted with ethyl acetate/petroleum ether (gradient ethyl acetate:petroleum ether from 0:1 to 1:1) provided the titled compound (38.0 mg, 38.7%). MS(ESI+) m/z 420.2 $[M+H]^+$; $^1H$ NMR (400 MHz, $CD_3OD$) δ ppm 2.18 (m, 1H), 2.39 (m, 1H), 2.53 (s, 3H), 3.04 (s, 3H), 3.32 (m, 4H), 4.13 (s, 2H), 4.26 (m, 1H), 6.18 (s, 1H), 6.20 (s, 1H), 7.34 (m, 4H).

Preparation of Compounds Derived from Intermediate a11

Example 11-1

N-{(3S)-1-[2-(4-chlorobenzyl)-5-methylpyrazolo[1,5-a]pyrimidin-7-yl]piperidin-3-yl)}methanesulfonamide A Methanesulfonyl chloride (35.4 mg, 0.309 mmol) was added dropwise to a solution of (3S)-1-[2-(4-chlorobenzyl)-5-methylpyrazolo[1,5-a]pyrimidin-7-yl]piperidin-3-amine (100 mg, 0.281 mmol, INTERMEDIATE a11) and triethylamine (0.196 mL, 1.405 mmol) in N,N-dimethylformamide (6 mL). The mixture was stirred at room temperature for 1 hour and then concentrated under vacuum. The residue was purified by preparative-HPLC (column: Waters XBridge® C18, 19×150 mm, 5 μm; mobile phase A: water/0.05% trifluoroacetic acid, mobile phase B: acetonitrile; flow rate: 20 mL/minute; gradient: 30% B to 70% B in 10 minutes; 254 nm) to provide the titled compound as a trifluoroacetic acid salt (17.6 mg, 11.4%). MS(ESI+) m/z 434.1 $[M+H]^+$; $^1H$ NMR (400 MHz, $CD_3OD$) δ ppm 1.78 (m, 2H), 2.02 (m, 1H), 2.15 (m, 1H), 2.53 (s, 3H), 2.99 (s, 3H), 3.70 (m, 1H), 3.81 (m, 2H), 4.13 (s, 2H), 4.53 (m, 1H), 4.95 (m, 1H), 6.23 (s, 1H), 6.48 (s, 1H), 7.28 (m, 4H).

Preparation of Compounds Derived from Intermediate a12

Example 12-1

2-{1-[2-(3-chlorobenzyl)-5-methylpyrazolo[1,5-a]pyrimidin-7-yl]piperidin-2-yl}ethanol A mixture of 7-chloro-2-(3-chlorobenzyl)-5-methylpyrazolo[1,5-a]pyrimidine (80 mg, 0.274 mmol, INTERMEDIATE a12), 2-(piperidin-2-yl)ethanol (70.8 mg, 0.548 mmol), and N-ethyl-N-isopropylpropan-2-amine (142 mg, 1.095 mmol) in ethanol (3 mL) were stirred at room temperature for 12 h and then at 50° C. for 6 h.

For work-up, the reaction mixture was extracted with $H_2O/CH_2Cl_2$, and the combined organic layers were washed with brine, dried over $MgSO_4$, filtered, and concentrated. After chromatographic purification using a Teledyne Isco CombiFlash® system (normal phase: 4 g column, eluent: 3-5% $CH_3OH/CH_2Cl_2$), the titled compound was obtained as clear oil (40 mg, 38.0%). LC-MS (ESI+) m/z 385.2 $[M+H]^+$; $^1H$ NMR (600 MHz, DMSO-$d_6$) δ ppm 7.39 (t, J=1.8 Hz, 1H), 7.36-7.25 (m, 4H), 6.25 (s, 2H), 6.13 (s, 1H), 4.99 (q, J=5.6, 5.0 Hz, 2H), 4.63 (t, J=5.2 Hz, 1H), 4.06 (s, 3H), 3.26 (td, J=12.2, 2.9 Hz, 1H), 2.37 (s, 2H), 1.91-1.58 (m, 7H).

Determination of Biological Activity

Abbreviations: EGTA for ethylene glycol-bis(2-aminoethylether)-N,N,N', N'-tetraacetic acid; GABA for γ-aminobutyric acid; GTPgS for guanosine 5'-O-[gamma-thio]triphosphate; and Tris for tris(hydroxymethyl)aminomethane.

Preparation of Rat Brain Membranes for Native Receptor Assays

Membranes from rat brain cortex were prepared as described in detail by Olpe et al. and stored at concentrations of 1.66 mg/mL protein at −80° C. until required. (Olpe, H.-R, et al. Eur J Pharmacol 1990; 187: 27-38).

[$^{35}$S] GTPgS Binding Assay

The composition of the assay mixtures [in a final volume of 200 μL in 96-well U-bottom plates (Greiner) was as follows: 50 mM Tris-HCl buffer, pH 7.7, 10 mM $MgCl_2$, 0.2 mM EGTA, 2 mM $CaCl_2$, 100 mM NaCl, 20 M guanosine 5'-diphosphate (Sigma), 0.3 nM [$^{35}$S]GTPgS (1250 Ci/mmol (PerkinElmer)), and the test compounds at increasing concentrations (from 10 nM up to 10 M), 10 g of rat cortical membranes, and a concentration of 1 M GABA, that has been observed in previous experiments to correspond to the $EC_{25}$, a concentration that gives 25% of the maximal response of GABA. The samples were incubated at room temperature for 60 minutes on a shaker. The incubation was stopped by rapid vacuum filtration over glass-fiber filter plates (UniFilter-96 well, GF/B membrane plates, PerkinElmer) using a 96-well plate harvester (TOMTEK© Harvester). The UniFilter plate was washed five times with ice-cold wash buffer (50 mM Tris-HCl buffer, pH 7.7, 10 mM $MgCl_2$, and 100 mM NaCl. After filtration the plate was dried for 90 minutes at 55° C. The plates were closed on the bottom with black sealing membranes, and liquid scintillation cocktail (35 μL, Betaplate Scint, PerkinElmer) was added to each well. After sealing the top of the plate, an additional incubation step of 90 minutes at room temperature followed before measuring the plate. The amount of membrane-bound [$^{35}$S]GTPgS was measured using a 96-well plate reader (Microbeta®, PerkinElmer). Nonspecific binding was measured in the presence of unlabeled 10 μM of GTPgS (Millipore) and without GABA. Basal binding was measured in the absence of 1 μM GABA, and maximal binding was measured in the presence of GABA using 1 mM GABA concentrations.

Data analysis. The concentration-response curves of compounds of the present disclosure in the presence of $EC_{25}$ of GABA-B receptor agonist were generated using the GraphPad Prism® program (GraphPad Software, San Diego, Calif.). Data was normalized using basal binding as 0% and maximal binding as 100%. The curves were fitted by non-linear regression allowing determination of $EC_{50}$ values from sigmoidal dose-response curves. Each curve was performed using triplicate sample per date point and 10 concentrations.

| Example | GTPgS Binding $EC_{50}$ (μM) |
|---|---|
| 1-1 | 1.4 |
| 1-2 | 1.66 |
| 1-3 | 2.55 |
| 1-4 | 2.89 |
| 1-5 | 5.93 |
| 1-6 | 0.974 |
| 1-7 | 1.23 |
| 1-8 | 1.3 |
| 1-9 | 2.57 |
| 1-10 | >10 |
| 1-11 | >10 |
| 1-12 | 3.97 |
| 1-13 | >10 |
| 1-14 | 1.03 |
| 1-15 | 1.18 |
| 1-16 | >10 |
| 1-17 | >10 |
| 1-18 | 2.69 |
| 1-19 | 10 |
| 1-20 | 2.15 |
| 1-21 | 1.38 |
| 2-1 | 0.118 |
| 2-2 | 0.435 |
| 2-3 | 0.508 |
| 2-4 | 0.128 |
| 2-5 | 0.146 |
| 2-6 | 0.242 |
| 2-7 | 0.185 |
| 2-8 | 0.071 |
| 2-9 | 0.604 |
| 2-10 | 0.152 |
| 2-11 | 0.057 |
| 2-12 | 2.82 |
| 2-13 | 0.446 |
| 2-14 | 0.165 |
| 2-15 | 3.93 |
| 2-16 | 0.586 |
| 2-17 | 2.18 |
| 2-18 | 0.499 |
| 2-19 | 1.31 |
| 2-20 | 0.093 |
| 2-21 | 0.394 |
| 2-22 | 0.07 |
| 2-23 | 2.73 |
| 3-1 | 0.008 |
| 3-2 | 0.014 |
| 4-1 | 0.005 |
| 4-2 | 0.009 |
| 5-1 | 0.003 |
| 5-2 | 0.007 |
| 6-1 | 1.82 |
| 7-1 | 1.08 |
| 8-1 | >10 |
| 8-2 | 0.087 |
| 8-3 | 0.42 |
| 8-4 | 0.827 |
| 8-5 | 0.365 |
| 8-6 | 0.509 |
| 8-7 | 2 |
| 8-8 | 0.746 |

-continued

| Example | GTPgS Binding $EC_{50}$ (μM) |
|---|---|
| 8-9 | 0.344 |
| 8-10 | >10 |
| 8-11 | 0.378 |
| 8-12 | 0.37 |
| 8-13 | 2.55 |
| 8-14 | 0.593 |
| 8-15 | 0.57 |
| 8-16 | 2.18 |
| 8-17 | 0.76 |
| 8-18 | 0.746 |
| 8-19 | 0.274 |
| 8-20 | 0.5 |
| 8-21 | 0.561 |
| 8-22 | 0.771 |
| 9-1 | 1.54 |
| 9-2 | 1.6 |
| 9-3 | 2.02 |
| 9-4 | 0.628 |
| 9-5 | 1.66 |
| 9-6 | 0.798 |
| 9-7 | 1.32 |
| 9-8 | 9.3 |
| 9-9 | >10 |
| 9-10 | >10 |
| 9-11 | >10 |
| 10-1 | >10 |
| 11-1 | 3.51 |
| 12-1 | 5.67 |

It is understood that the foregoing detailed description and accompanying examples are merely illustrative and are not to be taken as limitations upon the scope of the invention, which is defined solely by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

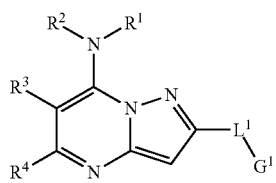

or a pharmaceutically acceptable salt or isotopically labeled form thereof, wherein:

$R^1$ is selected from the group consisting of $C_1$-$C_6$alkyl, $C_3$-$C_6$cycloalkyl and $C_3$-$C_6$cycloalkyl$C_1$-$C_6$alkyl, wherein the $C_1$-$C_6$alkyl and the $C_1$-$C_6$alkyl of $C_3$-$C_6$cycloalkyl$C_1$-$C_6$alkyl are unsubstituted or substituted with one or more substituents $R^{1a}$ independently selected from the group consisting of $C_1$-$C_6$alkoxy, $C_1$-$C_6$alkylcarbonylamino, $C_1$-$C_6$alkylsulfonylamino, amido, carboxy, cyano, halogen, hydroxy, and oxo; and the $C_3$-$C_6$cycloalkyl and the $C_3$-$C_6$cycloalkyl of $C_3$-$C_6$cycloalkyl$C_1$-$C_6$alkyl are unsubstituted or substituted with one or more substituents $R^{1b}$ independently selected from the group consisting of $C_1$-$C_6$alkoxy, $C_1$-$C_6$alkyl, amido, $C_1$-$C_6$alkylcarbonylamino, $C_1$-$C_6$alkylsulfonylamino, carboxy, cyano, halogen, halo$C_1$-$C_6$alkyl, hydroxy, hydroxy$C_1$-$C_6$alkyl, and oxo;

$R^2$ is selected from the group consisting of hydrogen, $C_1$-$C_6$alkyl, and halo$C_1$-$C_6$alkyl; or $R^1$, $R^2$ and the nitrogen to which they are attached form a saturated 4-7-membered N-bound heterocycle, which in addition to the nitrogen atom may have one further heteroatom selected from O, S and N as a ring member, wherein:

each such 4-7-membered heterocycle is unsubstituted or substituted with one or more identical or different substituents $R^{1c}$, where $R^{1c}$ is selected from the group consisting of $C_1$-$C_6$alkoxy, $C_1$-$C_6$alkyl, $C_1$-$C_6$alkylcarbonylamino, $C_1$-$C_6$alkylsulfonylamino, amido, carboxy, cyano, halogen, halo$C_1$-$C_6$alkyl, amino, hydroxy, hydroxy$C_1$-$C_6$alkyl, oxo, spirocyclic bound $C_3$-$C_6$cycloalkyl; and spirocyclic bound saturated 4-6-membered heterocycle; wherein each spirocyclic bound $C_3$-$C_6$cycloalkyl and spirocyclic bound 4-6-membered heterocycle is unsubstituted or substituted with one or more substituents independently selected from the group consisting of $C_1$-$C_6$alkyl, cyano, halogen, halo$C_1$-$C_6$alkyl, hydroxy, and hydroxy$C_1$-$C_6$alkyl;

$R^3$ is hydrogen;

$R^4$ is $C_1$-$C_6$alkyl;

$L^1$ is $(CR^5R^6)_m$, wherein m is 1 and $R^5$ and $R^6$, are, at each occurrence, independently selected from the group consisting of hydrogen and $C_1$-$C_6$alkyl;

and $G^1$ is selected from the group consisting of $C_5$-$C_{10}$cycloalkyl, 5-6-membered heteroaryl, and phenyl; wherein each $C_5$-$C_{10}$cycloalkyl, 5-6-membered heteroaryl, and phenyl is unsubstituted or substituted with one or more identical or different substituents $R^G$, where $R^G$ is selected from the group consisting of $C_1$-$C_6$alkyl, cyano, halo$C_1$-$C_6$alkyl, halogen, $C_1$-$C_6$alkoxy and halo$C_1$-$C_6$alkoxy.

2. The compound or pharmaceutically acceptable salt of claim 1 wherein $R^5$ is hydrogen and $R^6$ is $C_1$-$C_6$alkyl.

3. The compound or pharmaceutically acceptable salt of claim 1, wherein $G^1$ is selected from the group consisting of 5-6-membered heteroaryl and phenyl; wherein the 5-6-membered heteroaryl and phenyl are unsubstituted or carry 1, 2, 3 or 4 radicals $R^G$.

4. The compound or pharmaceutically acceptable salt of claim 1, wherein $G^1$ is selected from the group consisting of phenyl, 3-chlorophenyl, 4-chlorophenyl, 4-(trifluoromethyl)phenyl, pyridine-2-yl and 5-chloropyridin-2-yl.

5. The compound or pharmaceutically acceptable salt of claim 1, wherein:

$R^1$ is selected from the group consisting of $C_1$-$C_6$alkyl, $C_3$-$C_6$cycloalkyl and $C_3$-$C_6$cycloalkyl$C_1$-$C_6$alkyl, wherein the $C_1$-$C_6$alkyl and the $C_1$-$C_6$alkyl of $C_3$-$C_6$cycloalkyl$C_1$-$C_6$alkyl are unsubstituted or substituted with one or more substituents $R^{1a}$; and the $C_3$-$C_6$cycloalkyl, the $C_3$-$C_6$cycloalkyl of $C_3$-$C_6$cycloalkyl$C_1$-$C_6$alkyl, 4-7-membered heterocycle are unsubstituted or substituted with one or more substituents $R^{1b}$; and $R^2$ is selected from the group consisting of hydrogen, $C_1$-$C_6$alkyl, and halo$C_1$-$C_6$alkyl.

6. The compound or pharmaceutically acceptable salt of claim 5, wherein:

$R^1$ is $C_1$-$C_6$alkyl, wherein the $C_1$-$C_6$alkyl is unsubstituted or substituted with one or more halogen atoms; and $R^2$ is hydrogen.

7. The compound or pharmaceutically acceptable salt of claim 5, wherein:

$R^1$ is selected from the group consisting of $C_3$-$C_6$cycloalkyl and $C_3$-$C_6$cycloalkyl$C_1$-$C_6$alkyl, wherein the $C_1$-$C_6$alkyl of $C_3$-$C_6$cycloalkyl$C_1$-$C_6$alkyl is unsubstituted or substituted with one or more substituents $R^{1a}$, and the $C_3$-$C_6$cycloalkyl and the $C_3$-$C_6$cycloalkyl of $C_3$-$C_6$cycloalkyl$C_1$-$C_6$alkyl are unsubstituted or substituted with one or more substituents $R^{1b}$; and $R^2$ is selected from the group consisting of hydrogen, $C_1$-$C_6$alkyl, and halo$C_1$-$C_6$alkyl.

8. The compound or pharmaceutically acceptable salt of claim 1, wherein:

$R^1$, $R^2$ and the nitrogen to which they are attached form a 4-7-membered heterocycle selected from the group consisting of azetidinyl, pyrrolidinyl, piperidinyl, piperazinyl, morpholinyl, thiomorpholinyl, and azepanyl wherein azetidinyl, pyrrolidinyl, piperidinyl, piperazinyl, morpholinyl, thiomorpholinyl, and azepanyl are unsubstituted or carry 1, 2, 3 or 4 identical or different radicals $R^{1c}$.

9. The compound or pharmaceutically acceptable salt of claim 8, wherein:

$R^1$, $R^2$ and the nitrogen to which they are attached form a 4-5-membered heterocycle selected from the group consisting of azetidinyl and pyrrolidinyl, wherein azetidinyl and pyrrolidinyl are unsubstituted or carry 1, 2, 3 or 4 identical or different radicals $R^{1c}$.

10. The compound or pharmaceutically acceptable salt of claim 8, wherein:

$R^1$, $R^2$ and the nitrogen to which they are attached form a 6-7-membered heterocycle selected from the group consisting of piperidinyl, piperazinyl, and azepanyl wherein piperidinyl, piperazinyl, and azepanyl are unsubstituted or carry 1, 2, 3 or 4 identical or different radicals $R^{1c}$.

11. The compound or pharmaceutically acceptable salt of claim 1, wherein the moiety $NR^1R^2$ is selected from the group consisting of azetidin-1-yl, 3-ethyl-2-carboxylazetidin-1-yl, pyrroldin-1-yl, 3,3-difluoropyrrolidin-1-yl, 3-(acetylamino)pyrrolidin-1-yl, 3-(methylsulfonylamino)pyrrolidin-1-yl, 3-aminocarbonylpyrrolidin-1-yl, piperidin-1-yl, 3-fluoropiperidin-1-yl, 4-fluoropiperidin-1-yl, 2-(2-hydroxyethyl)piperidin-1-yl, 2-ethylpiperidin-1-yl, 2-(hydroxymethyl)piperidin-1-yl, 3-(hydroxymethyl)piperidin-1-yl, 2-oxopiperidin-1-yl, 3-(methylsulfonylamino)piperidin-1-yl, 2-(2-hydroxyethyl)-3-oxopiperazin-1-yl, 3,3-difluorpiperidin-1-yl, 3-hydroxypiperidin-1-yl, 4-hydroxy-3,3-difluoropiperidin-1-yl, 2,2,2-trifluoroethylamino, tert-butylamino, 1-(trifluoromethyl)-ethylamino, 1-methylcyclopropylamino, 1-(trifluoromethyl)cyclopropylamino, 3-fluorocyclobutylamino, 3,3-difluorocyclobutylamino, 3-hydroxycyclobutylamino, (3,3-difluorocyclobutyl)methylamino, 2-oxa-6-azaspiro[3.4]oct-6-yl, 2-oxa-7- azaspiro-[3.5]non-7-yl, 7-oxa-2-azaspiro[3.5]non-2-yl and 3-hydroxy-7-azaspiro[3.4]oct-7-yl.

12. A compound, selected from the group consisting of:
2-{1-[2-(4-chlorobenzyl)-5-methylpyrazolo[1,5-a]pyrimidin-7-yl]piperidin-2-yl}ethanol;
{1-[2-(4-chlorobenzyl)-5-methylpyrazolo[1,5-a]pyrimidin-7-yl]piperidin-2-yl}methanol;
2-(4-chlorobenzyl)-5-methyl-N-(1-methylcyclopropyl)pyrazolo[1,5-a]pyrimidin-7-amine;
2-(4-chlorobenzyl)-7-(3,3-difluoropiperidin-1-yl)-5-methylpyrazolo[1,5-a]pyrimidine;
1-[2-(4-chlorobenzyl)-5-methylpyrazolo[1,5-a]pyrimidin-7-yl]-3,3-difluoropiperidin-4-ol;
(3S)-1-[2-(4-chlorobenzyl)-5-methylpyrazolo[1,5-a]pyrimidin-7-yl]piperidin-3-ol;
(3R)-1-[2-(4-chlorobenzyl)-5-methylpyrazolo[1,5-a]pyrimidin-7-yl]piperidin-3-ol;
{(3S)-1-[2-(4-chlorobenzyl)-5-methylpyrazolo[1,5-a]pyrimidin-7-yl]piperidin-3-yl}methanol;
2-(4-chlorobenzyl)-5-methyl-7-(piperidin-1-yl)pyrazolo[1,5-a]pyrimidine;
1-[2-(4-chlorobenzyl)-5-methylpyrazolo[1,5-a]pyrimidin-7-yl]piperidin-2-one;
N-{(3R)-1-[2-(4-chlorobenzyl)-5-methylpyrazolo[1,5-a]pyrimidin-7-yl]pyrrolidin-3-yl}acetamide;
2-(4-chlorobenzyl)-5-methyl-7-(pyrrolidin-1-yl)pyrazolo[1,5-a]pyrimidine;
7-(azetidin-1-yl)-2-(4-chlorobenzyl)-5-methylpyrazolo[1,5-a]pyrimidine;
N-tert-butyl-2-(4-chlorobenzyl)-5-methylpyrazolo[1,5-a]pyrimidin-7-amine;
2-(4-chlorobenzyl)-5-methyl-N-[1-(trifluoromethyl)cyclopropyl]pyrazolo[1,5-a]pyrimidin-7-amine;
2-(4-chlorobenzyl)-5-methyl-N-(2,2,2-trifluoroethyl)pyrazolo[1,5-a]pyrimidin-7-amine;
N-{(3S)-1-[2-(4-chlorobenzyl)-5-methylpyrazolo[1,5-a]pyrimidin-7-yl]pyrrolidin-3-yl}acetamide;
2-(4-chlorobenzyl)-5-methyl-N-[(2S)-1,1,1-trifluoropropan-2-yl]pyrazolo[1,5-a]pyrimidin-7-amine;
1-[2-(4-chlorobenzyl)-5-methylpyrazolo[1,5-a]pyrimidin-7-yl]piperidine-3-carboxamide;
2-(4-chlorobenzyl)-5-methyl-N-[(2R)-1,1,1-trifluoropropan-2-yl]pyrazolo[1,5-a]pyrimidin-7-amine;
{(3R)-1-[2-(4-chlorobenzyl)-5-methylpyrazolo[1,5-a]pyrimidin-7-yl]piperidin-3-yl}methanol;
2-(1-{2-[1-(4-chlorophenyl)ethyl]-5-methylpyrazolo[1,5-a]pyrimidin-7-yl}piperidin-2-yl)ethanol;
2-[1-(4-chlorophenyl)ethyl]-5-methyl-N-(1-methylcyclopropyl)pyrazolo[1,5-a]pyrimidin-7-amine;
2-[1-(4-chlorophenyl)ethyl]-7-(3,3-difluoropyrrolidin-1-yl)-5-methylpyrazolo[1,5-a]pyrimidine;
2-[1-(4-chlorophenyl)ethyl]-7-(4-fluoropiperidin-1-yl)-5-methylpyrazolo[1,5-a]pyrimidine;
(1-{2-[1-(4-chlorophenyl)ethyl]-5-methylpyrazolo[1,5-a]pyrimidin-7-yl}piperidin-2-yl)methanol;
2-[1-(4-chlorophenyl)ethyl]-7-(3-fluoropiperidin-1-yl)-5-methylpyrazolo[1,5-a]pyrimidine;
2-[1-(4-chlorophenyl)ethyl]-7-(3,3-difluoropiperidin-1-yl)-5-methylpyrazolo[1,5-a]pyrimidine;
N-tert-butyl-2-[1-(4-chlorophenyl)ethyl]-5-methylpyrazolo[1,5-a]pyrimidin-7-amine;
2-[1-(4-chlorophenyl)ethyl]-5-methyl-7-(2-oxa-7-azaspiro[3.5]non-7-yl)pyrazolo[1,5-a]pyrimidine;
(3S)-1-{2-[1-(4-chlorophenyl)ethyl]-5-methylpyrazolo[1,5-a]pyrimidin-7-yl}piperidin-3-ol;
(3R)-1-{2-[1-(4-chlorophenyl)ethyl]-5-methylpyrazolo[1,5-a]pyrimidin-7-yl}piperidin-3-ol;
7-(azetidin-1-yl)-2-[1-(4-chlorophenyl)ethyl]-5-methylpyrazolo[1,5-a]pyrimidine;
2-[1-(4-chlorophenyl)ethyl]-5-methyl-7-(7-oxa-2-azaspiro[3.5]non-2-yl)pyrazolo[1,5-a]pyrimidine;
2-[1-(4-chlorophenyl)ethyl]-N-(3-fluorocyclobutyl)-5-methylpyrazolo[1,5-a]pyrimidin-7-amine;
(2R,3R)-1-{2-[1-(4-chlorophenyl)ethyl]-5-methylpyrazolo[1,5-a]pyrimidin-7-yl}-3-ethylazetidine-2-carboxylic acid;
2-[1-(4-chlorophenyl)ethyl]-N-[(3,3-difluorocyclobutyl)methyl]-5-methylpyrazolo[1,5-a]pyrimidin-7-amine;
N-[(3S)-1-{2-[1-(4-chlorophenyl)ethyl]-5-methylpyrazolo[1,5-a]pyrimidin-7-yl}pyrrolidin-3-yl]acetamide;
cis-3-({2-[1-(4-chlorophenyl)ethyl]-5-methylpyrazolo[1,5-a]pyrimidin-7-yl}amino)cyclobutanol;
trans-3-({2-[1-(4-chlorophenyl)ethyl]-5-methylpyrazolo[1,5-a]pyrimidin-7-yl}amino)cyclobutanol;
6-{2-[1-(4-chlorophenyl)ethyl]-5-methylpyrazolo[1,5-a]pyrimidin-7-yl}-6-azaspiro[3.4]octan-1-ol;
2-[1-(4-chlorophenyl)ethyl]-N-(3,3-difluorocyclobutyl)-5-methylpyrazolo[1,5-a]pyrimidin-7-amine;
2-[1-(4-chlorophenyl)ethyl]-7-[(2R)-2-ethylpiperidin-1-yl]-5-methylpyrazolo[1,5-a]pyrimidine;
N-[(3R)-1-{2-[1-(4-chlorophenyl)ethyl]-5-methylpyrazolo[1,5-a]pyrimidin-7-yl}pyrrolidin-3-yl]acetamide;
2-(1-{2-[1-(4-chlorophenyl)propyl]-5-methylpyrazolo[1,5-a]pyrimidin-7-yl}piperidin-2-yl)ethanol;
2-[1-(4-chlorophenyl)propyl]-7-(3,3-difluoropiperidin-1-yl)-5-methylpyrazolo[1,5-a]pyrimidine;
2-(1-{2-[1-(4-chlorophenyl)-2-methylpropyl]-5-methylpyrazolo[1,5-a]pyrimidin-7-yl}piperidin-2-yl)ethanol;
2-[1-(4-chlorophenyl)-2-methylpropyl]-7-(3,3-difluoropiperidin-1-yl)-5-methylpyrazolo[1,5-a]pyrimidine;
2-(1-{2-[1-(4-chlorophenyl)butyl]-5-methylpyrazolo[1,5-a]pyrimidin-7-yl}piperidin-2-yl)ethanol;
2-[1-(4-chlorophenyl)butyl]-7-(3,3-difluoropiperidin-1-yl)-5-methylpyrazolo[1,5-a]pyrimidine;
2-(1-{5-methyl-2-[3-(trifluoromethyl)benzyl]pyrazolo[1,5-a]pyrimidin-7-yl}piperidin-2-yl)ethanol;
2-{1-[5-methyl-2-(tricyclo[3.3.1.1$^{3,7}$]dec-1-ylmethyl)pyrazolo[1,5-a]pyrimidin-7-yl]piperidin-2-yl}ethanol;
(2S)-1-(5-methyl-2-{1-[4-(trifluoromethyl)phenyl]ethyl}pyrazolo[1,5-a]pyrimidin-7-yl)azetidine-2-carboxamide;
2-[1-(5-methyl-2-{1-[4-(trifluoromethyl)phenyl]ethyl}pyrazolo[1,5-a]pyrimidin-7-yl)piperidin-2-yl]ethanol;
5-methyl-7-(2-oxa-6-azaspiro[3.4]oct-6-yl)-2-{1-[4-(trifluoromethyl)phenyl]ethyl}pyrazolo[1,5-a]pyrimidine;
5-methyl-7-(7-oxa-2-azaspiro[3.5]non-2-yl)-2-{1-[4-(trifluoromethyl)phenyl]ethyl}pyrazolo[1,5-a]pyrimidine;
(3R)-1-(5-methyl-2-{1-[4-(trifluoromethyl)phenyl]ethyl}pyrazolo[1,5-a]pyrimidin-7-yl)piperidin-3-ol;
N-(3-fluorocyclobutyl)-5-methyl-2-{1-[4-(trifluoromethyl)phenyl]ethyl}pyrazolo[1,5-a]pyrimidin-7-amine;
N-[(3S)-1-(5-methyl-2-{1-[4-(trifluoromethyl)phenyl]ethyl}pyrazolo[1,5-a]pyrimidin-7-yl)pyrrolidin-3-yl]acetamide;
5-methyl-N-(1-methylcyclopropyl)-2-{1-[4-(trifluoromethyl)phenyl]ethyl}pyrazolo[1,5-a]pyrimidin-7-amine;
[1-(5-methyl-2-{1-[4-(trifluoromethyl)phenyl]ethyl}pyrazolo[1,5-a]pyrimidin-7-yl)piperidin-2-yl]methanol;
(2S)-1-(5-methyl-2-{1-[4-(trifluoromethyl)phenyl]ethyl}pyrazolo[1,5-a]pyrimidin-7-yl)azetidine-2-carboxylic acid;

7-(4-fluoropiperidin-1-yl)-5-methyl-2-{1-[4-(trifluoromethyl)phenyl]ethyl}pyrazolo[1,5-a]pyrimidine;

7-(3-fluoropiperidin-1-yl)-5-methyl-2-{1-[4-(trifluoromethyl)phenyl]ethyl}pyrazolo[1,5-a]pyrimidine;

3-(2-hydroxyethyl)-4-(5-methyl-2-{1-[4-(trifluoromethyl)phenyl]ethyl}pyrazolo[1,5-a]pyrimidin-7-yl)piperazin-2-one;

N-[(3,3-difluorocyclobutyl)methyl]-5-methyl-2-{1-[4-(trifluoromethyl)phenyl]ethyl}pyrazolo[1,5-a]pyrimidin-7-amine;

7-(3,3-difluoropyrrolidin-1-yl)-5-methyl-2-{1-[4-(trifluoromethyl)phenyl]ethyl}pyrazolo[1,5-a]pyrimidine;

N-[(3R)-1-(5-methyl-2-{1-[4-(trifluoromethyl)phenyl]ethyl}pyrazolo[1,5-a]pyrimidin-7-yl)pyrrolidin-3-yl]acetamide;

7-(3,3-difluoropiperidin-1-yl)-5-methyl-2-{1-[4-(trifluoromethyl)phenyl]ethyl}pyrazolo[1,5-a]pyrimidine;

1-(5-methyl-2-{1-[4-(trifluoromethyl)phenyl]ethyl}pyrazolo[1,5-a]pyrimidin-7-yl)piperidin-2-one;

N-tert-butyl-5-methyl-2-{1-[4-(trifluoromethyl)phenyl]ethyl}pyrazolo[1,5-a]pyrimidin-7-amine;

N-(3,3-difluorocyclobutyl)-5-methyl-2-{1-[4-(trifluoromethyl)phenyl]ethyl}pyrazolo[1,5-a]pyrimidin-7-amine;

5-methyl-7-(2-oxa-7-azaspiro[3.5]non-7-yl)-2-{1-[4-(trifluoromethyl)phenyl]ethyl}pyrazolo[1,5-a]pyrimidine;

1-(5-methyl-2-{1-[4-(trifluoromethyl)phenyl]ethyl}pyrazolo[1,5-a]pyrimidin-7-yl)pyrrolidine-3-carboxamide;

(1-{2-[1-(5-chloropyridin-2-yl)ethyl]-5-methylpyrazolo[1,5-a]pyrimidin-7-yl}piperidin-3-yl)methanol;

2-[1-(5-chloropyridin-2-yl)ethyl]-N-(3,3-difluorocyclobutyl)-5-methylpyrazolo[1,5-a]pyrimidin-7-amine;

(3S)-1-{2-[1-(5-chloropyridin-2-yl)ethyl]-5-methylpyrazolo[1,5-a]pyrimidin-7-yl}piperidin-3-ol;

2-[1-(5-chloropyridin-2-yl)ethyl]-7-(3,3-difluoropiperidin-1-yl)-5-methylpyrazolo[1,5-a]pyrimidine;

2-[1-(5-chloropyridin-2-yl)ethyl]-7-(3,3-difluoropyrrolidin-1-yl)-5-methylpyrazolo[1,5-a]pyrimidine;

N-tert-butyl-2-[1-(5-chloropyridin-2-yl)ethyl]-5-methylpyrazolo[1,5-a]pyrimidin-7-amine;

2-[1-(5-chloropyridin-2-yl)ethyl]-5-methyl-N-(1-methylcyclopropyl)pyrazolo[1,5-a]pyrimidin-7-amine;

2-[1-(5-chloropyridin-2-yl)ethyl]-N-(3-fluorocyclobutyl)-5-methylpyrazolo[1,5-a]pyrimidin-7-amine;

2-[1-(5-chloropyridin-2-yl)ethyl]-5-methyl-7-(7-oxa-2-azaspiro[3.5]non-2-yl)pyrazolo[1,5-a]pyrimidine;

N-[(3R)-1-{2-[1-(5-chloropyridin-2-yl)ethyl]-5-methylpyrazolo[1,5-a]pyrimidin-7-yl}pyrrolidin-3-yl]acetamide;

N-[(3S)-1-{2-[1-(5-chloropyridin-2-yl)ethyl]-5-methylpyrazolo[1,5-a]pyrimidin-7-yl}pyrrolidin-3-yl]acetamide;

N-{(3R)-1-[2-(4-chlorobenzyl)-5-methylpyrazolo[1,5-a]pyrimidin-7-yl]pyrrolidin-3-yl}methanesulfonamide;

N-{(3S)-1-[2-(4-chlorobenzyl)-5-methylpyrazolo[1,5-a]pyrimidin-7-yl]piperidin-3-yl}methanesulfonamide; and 2-{1-[2-(3-chlorobenzyl)-5-methylpyrazolo[1,5-a]pyrimidin-7-yl]piperidin-2-yl}ethanol, or a pharmaceutically acceptable salt thereof.

13. A pharmaceutical composition comprising a therapeutically effective amount of a compound or pharmaceutically acceptable salt of claim 1 in combination with a pharmaceutically acceptable carrier.

14. The compound of pharmaceutically acceptable salt of claim 1, wherein:
$R^1$ is selected from the group consisting of $C_1$-$C_6$alkyl, $C_3$-$C_6$cycloalkyl and $C_3$-$C_6$cycloalkyl$C_1$-$C_6$alkyl; wherein the $C_1$-$C_6$alkyl and the $C_1$-$C_6$alkyl of $C_3$-$C_6$cycloalkyl$C_1$-$C_6$alkyl are unsubstituted or substituted with one or more substituents $R^{1a}$ independently selected from the group consisting of cyano and halogen; and the $C_3$-$C_6$cycloalkyl and the $C_3$-$C_6$cycloalkyl$C_1$-$C_6$alkyl are unsubstituted or substituted with one or more substituents $R^{1b}$ independently selected from the group consisting of $C_1$-$C_6$, cyano, halogen and halo$C_1$-$C_6$alkyl;

$R^2$ is hydrogen; or $R^1$, $R^2$ and the nitrogen to which they are attached from a saturated 4-6-membered N-bound heterocycle, which in addition to the nitrogen atom may have one further heteroatom selected from O and N as a ring member, wherein:

each such 4-6-membered heterocycle is unsubstituted or substituted with one or more identical or different substituents $R^{1c}$, where $R^{1c}$ is selected from the group consisting of $C_1$-$C_6$alkyl, $C_1$-$C_6$alkylcarbonylamino, $C_1$-$C_6$alkylsulfonylamino, amido, carboxy, cyano, halogen, halo$C_1$-$C_6$alkyl, hydroxy, hydroxy$C_1$-$C_6$alkyl, oxo, spirocyclic bound $C_3$-$C_6$cycloalkyl; and spirocyclic bound saturated 4-6-membered heterocycle; wherein each spirocyclic bound $C_3$-$C_6$cycloalkyl and spirocyclic bound 4-6-membered heterocycle is unsubstituted or substituted with one or more substituents independently selected from the group consisting of $C_1$-$C_6$alkyl, hydroxy, and hydroxy$C_1$-$C_6$alkyl; and $G^1$ is selected from the group consisting of $C_5$-$C_{10}$cycloalkyl, 5-6-membered heteroaryl, and phenyl; wherein each $C_5$-$C_{10}$cycloalkyl, 5-6-membered heteroaryl, and phenyl is unsubstituted or substituted with one or more identical or different substituents $R^G$, where $R^G$ is selected from the group consisting of $C_1$-$C_6$alkyl, cyano, halo$C_1$-$C_6$alkyl and halogen.

* * * * *